United States Patent
Zhang et al.

(10) Patent No.: US 9,249,084 B2
(45) Date of Patent: Feb. 2, 2016

(54) SUBSTITUTED N-PENTANAMIDE COMPOUNDS, PREPARATION METHOD AND THE USE THEREOF

(75) Inventors: Qiang Zhang, Shanghai (CN); Rongxia Zhang, Shanghai (CN); Guanghui Tian, Shanghai (CN); Jianfeng Li, Shanghai (CN); Fuqiang Zhu, Shanghai (CN); Xiangrui Jiang, Shanghai (CN); Jingshan Shen, Shanghai (CN)

(73) Assignees: Shanghai Institute of Materia Medica, Chinese Academy of Sciences, Shanghai (CN); Topharman Shanghai Co., Ltd., Shanghai (CN)

( * ) Notice: Subject to any disclaimer, the term of this patent is extended or adjusted under 35 U.S.C. 154(b) by 176 days.

(21) Appl. No.: 13/982,733

(22) PCT Filed: Jan. 31, 2012

(86) PCT No.: PCT/CN2012/070781
§ 371 (c)(1),
(2), (4) Date: Sep. 20, 2013

(87) PCT Pub. No.: WO2012/103799
PCT Pub. Date: Aug. 9, 2012

(65) Prior Publication Data
US 2014/0046074 A1 Feb. 13, 2014

(30) Foreign Application Priority Data
Jan. 31, 2011 (CN) .......................... 2011 1 0034202

(51) Int. Cl.
| | | |
|---|---|---|
| C07C 213/02 | (2006.01) |
| C07C 59/64 | (2006.01) |
| C07C 235/34 | (2006.01) |
| C07C 309/75 | (2006.01) |
| C07C 309/66 | (2006.01) |
| C07C 43/225 | (2006.01) |
| C07D 263/26 | (2006.01) |
| C07C 17/16 | (2006.01) |
| C07C 215/54 | (2006.01) |
| C07C 217/62 | (2006.01) |
| C07C 309/73 | (2006.01) |
| C07D 263/52 | (2006.01) |
| C07C 43/23 | (2006.01) |
| C07C 59/68 | (2006.01) |
| C07C 41/26 | (2006.01) |

(52) U.S. Cl.
CPC .............. *C07C 213/02* (2013.01); *C07C 17/16* (2013.01); *C07C 41/26* (2013.01); *C07C 43/225* (2013.01); *C07C 43/23* (2013.01); *C07C 59/64* (2013.01); *C07C 59/68* (2013.01); *C07C 215/54* (2013.01); *C07C 217/62* (2013.01); *C07C 235/34* (2013.01); *C07C 309/66* (2013.01); *C07C 309/73* (2013.01); *C07C 309/75* (2013.01); *C07D 263/26* (2013.01); *C07D 263/52* (2013.01)

(58) Field of Classification Search
None
See application file for complete search history.

(56) References Cited

U.S. PATENT DOCUMENTS

2009/0326271 A1 12/2009 Hell

FOREIGN PATENT DOCUMENTS

| CN | 101495445 A | 7/2009 |
| EP | 0693475 A1 | 1/1996 |
| EP | 2049464 B1 | 7/2011 |
| WO | 2011/080756 A1 | 7/2011 |
| WO | 2011080736 A1 | 7/2011 |
| WO | 2011092719 A2 | 8/2011 |
| WO | 2011/157390 A2 | 12/2011 |

OTHER PUBLICATIONS

International Search Report issued in International Application No. PCT/CN2012/070781, mailed on May 3, 2012.
Extended European Search Report issued on Jun. 24, 2014, in corresponding European Patent Application No. 12742093.
Romines, Karen R., et al., "A Facile Asymmetric Synthesis of 1, 2, 3—Substituted Indenes," The Journal of Organic Chemistry, vol. 64, No. 5, Mar. 1, 1999, pp. 1733-1737.
Terlinden, R., et al., "In vitro and in vivo characterization of tapentadol metabolites," Methods and Findings in Experimental and Clinical Pharmacology, vol. 32, No. 1, Jan. 1, 2010, pp. 31-38.

*Primary Examiner* — Kamal Saeed
(74) *Attorney, Agent, or Firm* — Ping Wang; Andrews Kurth LLP

(57) ABSTRACT

The present invention relates to a (2R,3R)-3-(3-substituted phenyl)-2-methyl n-pentanamide compounds as shown in the formula I and the preparation method thereof, wherein the substituents are as defined in the specification, the present invention further relates to a use of the above compounds for the preparation of tapentadol II or its pharmaceutically acceptable salt, and the intermediates involved in the preparation process.

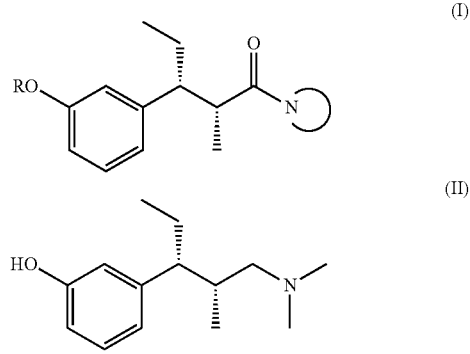

25 Claims, No Drawings

SUBSTITUTED N-PENTANAMIDE COMPOUNDS, PREPARATION METHOD AND THE USE THEREOF

FIELD OF THE INVENTION

The invention relates to the field of pharmaceutical chemistry and organic chemistry, specifically, the present invention relates to (2R,3R)-3-(3-substituted phenyl)-2-methyl-n-pentanamide compounds representing by the following structure formula (I), the preparation method thereof, and the use thereof for preparation of tapentadol (II) or its pharmaceutically acceptable salt.

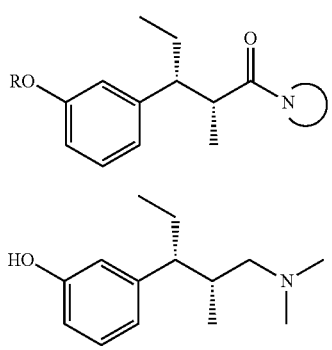

BACKGROUND OF THE INVENTION

Tapentadol is central analgesic with a dual action mechanism developed by Johnson & Johnson, since it is both the μ-type opioid receptor agonist and norepinephrine reuptake inhibitor, up to now it is the first single-molecule drug which has both above pharmacological effects. It was approved for marketing on Nov. 21, 2008 by the U.S. Food and Drug Administration, for the treatment of moderate to severe acute pain. Studies show that tapentadol is independent of metabolism activation and has no active metabolite; moreover, it has curative effect on all of the acute, inflammatory and chronic neuropathic pain models, and its effectiveness is between morphine and tramadol; in addition, the satisfactory plasma concentration can be obtained by both intravenous and oral administration of tapentadol, it is not easier to cause analgesic tolerance and physical dependence than morphine, and its clinical application shows mild side effects and well tolerance. Its chemical name is: (+)-(1R,2R)-3-(3-dimethylamino-1-ethyl-2-methylpropyl)-phenol, whose structure is represented by the following formula (II):

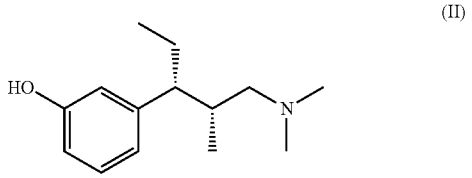 [SMILES: CC[C@@H](c1cccc(O)c1)[C@@H](C)CN(C)C]

It is recorded in European Patent No. EP693475 a method for preparing compound (II) from 3-pentanone through the Mannich reaction, Grignard reaction, crystallization to separate diastereoisomer, column chromatography to separate diastereoisomer, chloridization, elimination and demethylation reaction, the method is shown as Reaction Scheme 1:

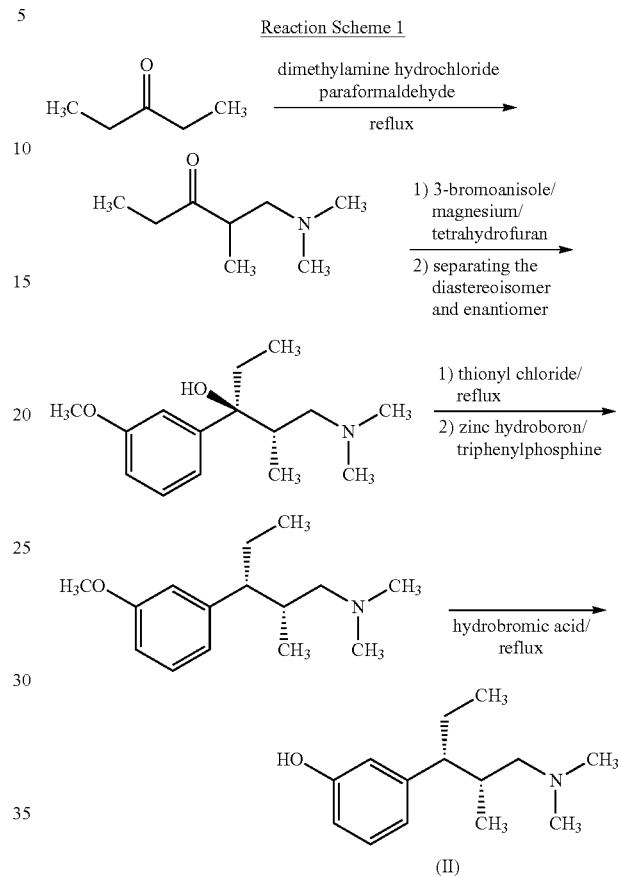

It is recorded in European Patent No. EP2049464 and U.S. Patent No. US2009326271 a method for preparing compound (II) from 3'-benzyloxyphenyl ethyl ketone through Mannich reaction, chiral separation, Grignard reaction, dehydration, and debenzylation together with stereoselective hydrogenation, the method is shown as Reaction Scheme 2:

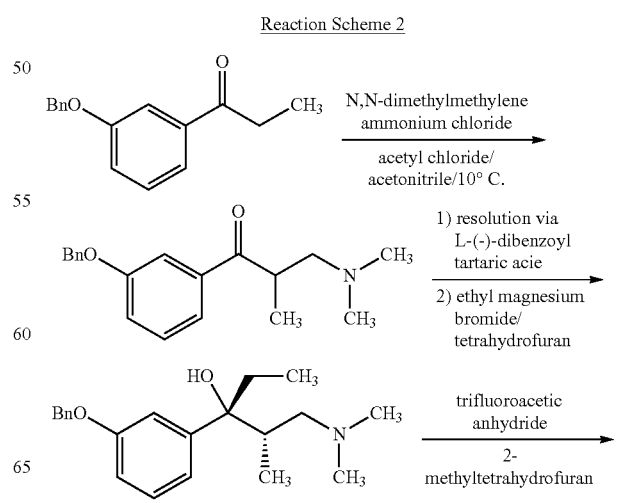

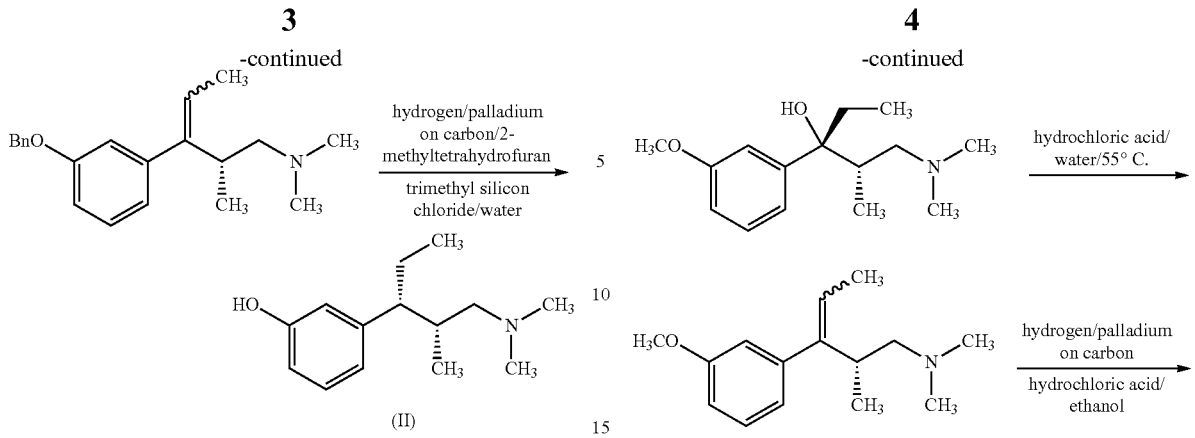

It is recorded in European Patent No. EP2046724 a method for preparing the hydrochloride of compound (II) from 3'-methoxyphenyl ethyl ketone through Mannich reaction, chiral separation, Grignard reaction, dehydration, stereoselective hydrogenation, demethylation reaction, and directly adding hydrochloric acid without separation, the method is shown as Reaction Scheme 3:

Reaction Scheme 3

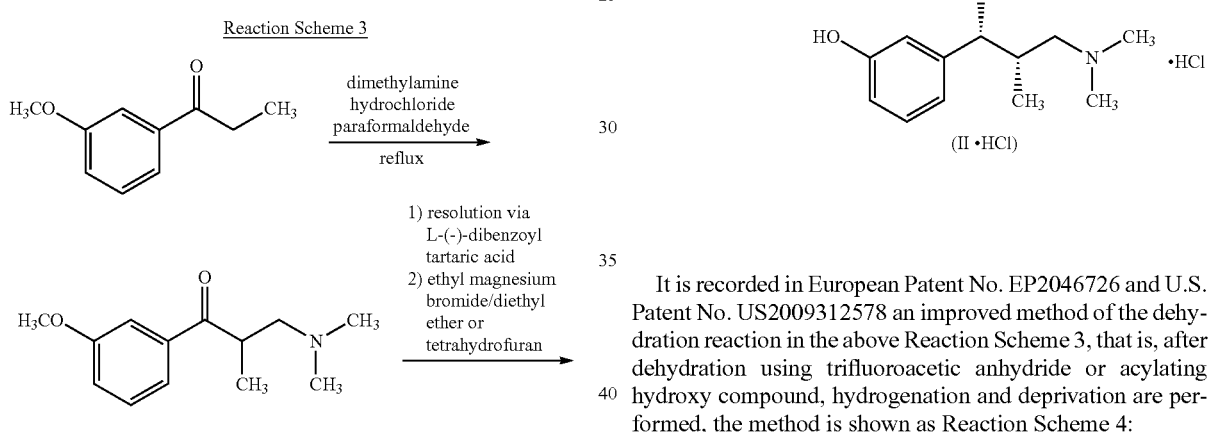

It is recorded in European Patent No. EP2046726 and U.S. Patent No. US2009312578 an improved method of the dehydration reaction in the above Reaction Scheme 3, that is, after dehydration using trifluoroacetic anhydride or acylating hydroxy compound, hydrogenation and deprivation are performed, the method is shown as Reaction Scheme 4:

Reaction Scheme 4

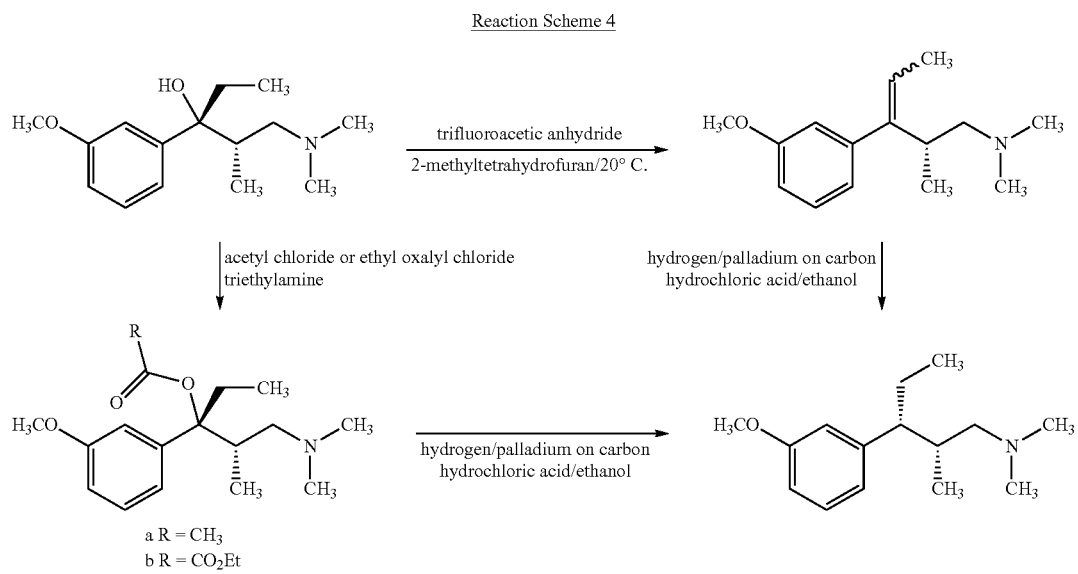

The existing synthesis methods of tapentadol adopt the column chromatography or resolution methods, which have a high cost and low yield, and are not suitable for industrial production. Therefore, it is eager to find a method which has simple process, high yield, low cost and is suitable for industrial production.

SUMMARY OF THE INVENTION

In order to overcome the disadvantages of high cost and low yield etc. of the method for preparation of tapentadol in the prior art, the present invention provides (2R,3R)-3-(3-substituted phenyl)-2-methyl n-pentanamide compounds having a structure represented by the following formula I, and the compounds of formula I may be used to synthesize tapentadol or its pharmaceutically acceptable salt economically, conveniently and with a high yield.

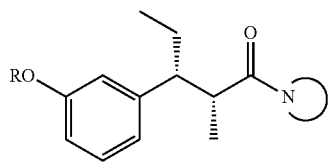

It is one object of the present invention to provide (2R,3R)-3-(3-substituted phenyl)-2-methyl n-pentanamide compounds represented by formula I.

It is another object of the present invention to provide a method for preparing (2R,3R)-3-(3-substituted phenyl)-2-methyl n-pentanamide compounds represented by formula I.

It is still another object of the present invention to provide a use of (2R,3R)-3-(3-substituted phenyl)-2-methyl n-pentanamide compounds represented by formula I for preparing tapentadol.

It is yet another object of the present invention to provide the intermediates involved in the above preparation method.

To achieve the above object, the present invention provides (2R,3R)-3-(3-substituted phenyl)-2-methyl n-pentanamide compounds represented by formula I.

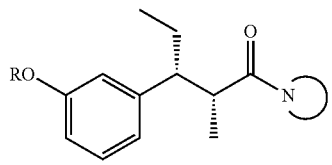

wherein, R is the protecting group of the phenolic hydroxy, R may form an ether group or an ester group with the phenolic hydroxy; R may be one selected from the group consisting of C1-C6 linear or branched alkyl group, substituted or unsubstituted aryl, substituted or unsubstituted arylalkyl, alkylsilyl, C1-C6 alkoxymethyl, C1-C6 alkyloyl, substituted or unsubstituted aryloyl; wherein the substituent may be hydroxy, halogen, C1-C6 alkyl, C1-C6 alkoxy, etc.; the aryl may be phenyl, naphthyl, etc.;

is the residue of chiral auxiliaries, which is defined as follows:

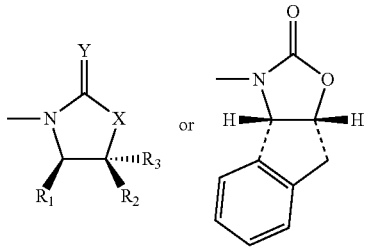

wherein, X is O, S or $NR_7$, wherein $R_7$ is hydrogen, C1-C6 branched or linear alkyl;

Y is O or S;

$R_1$ is C1-C6 alkyl, substituted or unsubstituted phenyl (Ph), substituted or unsubstituted naphthyl, substituted or unsubstituted benzyl (Bn), C1-C6 alkoxycarbonyl, wherein the substituent on phenyl, naphthyl or benzyl is 1 to 3 substituent(s) selected from hydroxy, halogen, C1-C6 alkyl and C1-C6 alkoxy;

$R_2$ and $R_3$ are each independently selected from H; C1-C6 alkyl; phenyl; phenyl substituted with 1 to 3 substituent(s) selected from hydroxy, halogen, C1-C6 alkyl and C1-C6 alkoxy.

In a preferred embodiment of the present invention, in formula I,

R may form an ether group or an ester group with the phenolic hydroxy; R may be selected from the group consisting of C1-C6 linear or branched alkyl group, substituted or unsubstituted aryl, substituted or unsubstituted arylalkyl, alkylsilyl, C1-C6 alkoxymethyl, C1-C6 alkyloyl, substituted or unsubstituted aryloyl; wherein the substituent may be hydroxy, halogen, C1-C6 alkyl, C1-C6 alkoxy, etc.; the aryl may be phenyl, naphthyl, etc.

X is O; and Y is O;

$R_1$ is C1-C6 alkyl, substituted or unsubstituted phenyl (Ph), or substituted or unsubstituted benzyl (Bn), wherein the substituent on phenyl or benzyl is 1 to 3 substituent(s) selected from hydroxy, halogen, C1-C6 alkyl and C1-C6 alkoxy;

$R_2$ and $R_3$ are each independently selected from H, C1-C6 alkyl and phenyl.

In a further preferred embodiment of the present invention, in formula I,

R is benzyl, methyl, t-butyl, triphenylmethyl, methoxymethyl, trimethylsilyl, t-butyldimethylsilyl, acetyl or benzoyl;

X is O; and Y is O;

$R_1$ is phenyl; phenyl substituted with 1 to 3 substituent(s) selected from hydroxy, halogen, C1-C6 alkyl and C1-C6 alkoxy; or benzyl;

$R_2$ and $R_3$ are each independently selected from H, C1-C6 alkyl and phenyl.

Still in a further preferred embodiment of the present invention, the compound represented by formula I is:

(1) 3-[(2R,3R)-2-methyl-1-oxo-3-[3-(phenylmethoxy)phenyl]pentyl]-4R-phenyl-2-Oxazolidinone

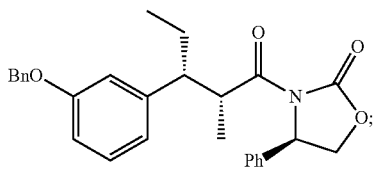 [SMILES: CC[C@@H](c1cccc(OCc2ccccc2)c1)[C@@H](C)C(=O)N1C(=O)OC[C@H]1c1ccccc1]

(2) 3-[(2R,3R)-2-methyl-1-oxo-3-[3-(phenylmethoxy)phenyl]pentyl]-4R,5 S-diphenyl-2-Oxazolidinone

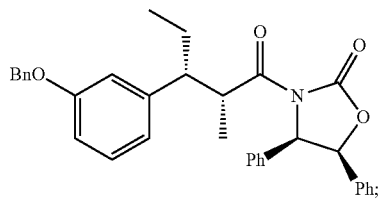 [SMILES: CC[C@@H](c1cccc(OCc2ccccc2)c1)[C@@H](C)C(=O)N1C(=O)O[C@@H](c2ccccc2)[C@H]1c1ccccc1]

(3) 3-[(2R,3R)-3-(3-methoxyphenyl)-2-methyl-1-oxopentyl]-4R,5S-di phenyl-2-Oxazolidinone

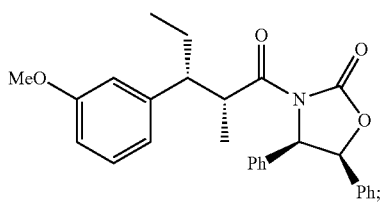

(4) 3-[(2R,3R)-3-(3-methoxyphenyl)-2-methyl-1-oxopentyl]-4R-phenyl-2-Oxazolidinone

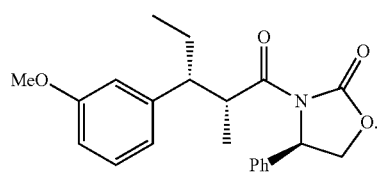 [SMILES: CC[C@@H](c1cccc(OC)c1)[C@@H](C)C(=O)N1C(=O)OC[C@H]1c1ccccc1]

The present invention provides a method for preparing (2R,3R)-3-(3-substituted phenyl)-2-methyl n-pentanamide compounds as shown in formula I, said method comprises:

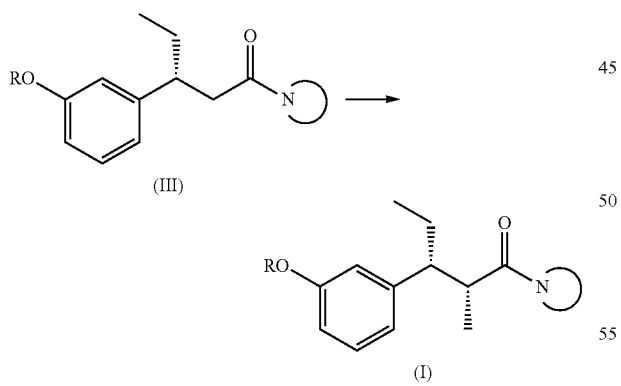

wherein, R is a protecting group of the phenolic hydroxy, R may form an ether group or an ester group with the phenolic hydroxy; R may be selected from C1-C6 linear or branched alkyl, substituted or unsubstituted aryl, substituted or unsubstituted arylalkyl, alkylsilyl, C1-C6 alkoxymethyl, C1-C6 alkyloyl, substituted or unsubstituted aryloyl; wherein, the said substituent may be hydroxyl, halogen, C1-C6 alkyl, C1-C6 alkoxy, etc.; the said aryl may be phenyl, naphthyl, etc.;

is the residue of chiral auxiliaries, which is defined as follows:

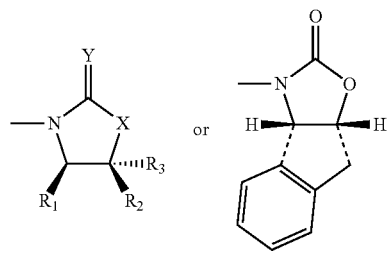

wherein, X is O, S or $NR_7$, in which $R_7$ is hydrogen, C1-C6 branched or linear alkyl; Y is O or S;

$R_1$ is C1-C6 alkyl group, substituted or unsubstituted phenyl (Ph), substituted or unsubstituted naphthyl, substituted or unsubstituted benzyl (Bn), C1-C6 alkoxycarbonyl, wherein, the substituent on phenyl, naphthyl or benzyl is 1 to 3 substituent(s) selected from hydroxy, halogen, C1-C6 alkyl and C1-C6 alkoxy;

$R_2$ and $R_3$ are each independently selected from H; C1-C6 alkyl; phenyl; phenyl substituted with 1 to 3 substituent(s) selected from hydroxy, halogen, C1-C6 alkyl and C1-C6 alkoxy.

The α-methylation reaction is conducted between a compound of formula III and hydrocarbylation reagent in the presence of strong base or Lewis acid, and a post-treatment is performed by a conventional method to give the compound I; the said hydrocarbylation reagent is any one of methyl iodide, methyl bromide, methyl chloride, methyl trifluoromethanesulfonate, methyl benzenesulfonate and methyl fluorosulfonate; the said strong base is any one of sodium hexamethyldisilylamide (NaHMDS), lithium hexamethyldisilylamide (LiHMDS), potassium hexamethyldisilylamide (KHMDS), lithium amide, sodium amide, potassium amide, lithium diisopropylamide (LDA) and n-butyl lithium; the said Lewis acid is any one of titanium tetrachloride, aluminum trichloride, ferric trichloride, zinc chloride and antimony pentafluoride.

The method for preparing (2R,3R)-3-(3-substituted phenyl)-2-methyl n-pentanamide compounds shown as formula I comprises: firstly, 3-(3-hydroxy protected phenyl) acrylic acid (IV) is reacted with a chiral auxiliary

under the activation of a carboxylic acid activating agent to obtain a compound V; the compound V is subjected to asymmetric Michael addition with ethyl magnesium halide under the condition of organic metal reagent in an inert solvent, then the resultant is post-treated by a conventional method to give Compound III; compound III and hydrocarbylation reagent are conducted the α-methylation reaction in the presence of strong base or Lewis acid, then the resultant is post-treated by a conventional method to give the compound I. The method is shown as Reaction Scheme 5:

Reaction Scheme 5

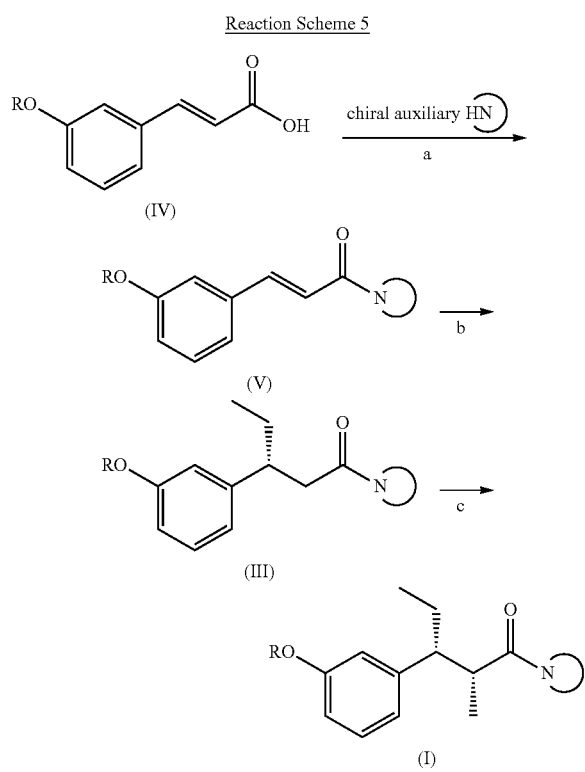

Wherein, R and

are as defined above.

The method comprises the following steps:

(1) In step a, 3-(3-hydroxy protected phenyl)acrylic acid (IV) is reacted in the presence of carboxylic acid activating agent, chiral auxiliaries

and base, and with the suitable organic solvent and suitable temperatures to form Compound V.

The carboxylic acid activating agent is any one of thionyl chloride, oxalyl chloride, pivaloyl chloride, chloroformate, carbodiimides such as dicyclohexyl carbodiimide (DCC), 4-dimethylaminopyridine (DMAP) and carbonyldiimidazole (CDI);

said base is inorganic base or organic base, and may be any one selected from sodium hydride, potassium hydride, alkyl lithium (n-butyl lithium or t-butyl lithium), lithium amide, sodium amide, potassium amide, lithium diisopropylamide (LDA), lithium hexamethyldisilylamide (LiHMDS), sodium hexamethyldisilylamide (NaHMDS), sodium methoxide, sodium ethoxide, potassium tert-butoxide, sodium hydroxide, potassium hydroxide, calcium hydroxide, triethylamine, ethylenediamine, sodium carbonate, potassium carbonate, sodium bicarbonate and potassium bicarbonate;

Said organic solvents include: hydrocarbons, such as benzene, xylene, toluene, dichloromethane, chloroform; ethers such as tetrahydrofuran, diethyl ether, dipropyl ether, 1,4-dioxane; amides such as N,N-dimethylformamide, N,N-diethylformamide, N,N-dimethylacetamide; nitriles such as acetonitrile; and the mixtures of the above solvents, wherein, the preferred solvent is tetrahydrofuran, toluene, N,N-dimethylformamide or acetonitrile;

The reaction temperature is usually in the range of −100° C. to 50° C., preferably −80° C. to 30° C.

(2) In step b, the inert solution of the compound V was slowly added to the mixed solution of Grignard reagent ethyl magnesium halide and organic metal reagent at the suitable temperature, after the reaction was complete, the resultant was post-treated by a conventional method to give the Compound III.

Said organic metal reagent is any one of cuprous bromide dimethylsulfide, cuprous bromide, cuprous chloride and cuprous iodide. Said Grignard reagent ethyl magnesium halide is any one of ethyl magnesium bromide, ethyl magnesium iodide and ethyl magnesium chloride. The amount of the Grignard reagent is 1 to 10 times (molar ratio), preferably 1 to 4 times that of the compound V. The amount of the organic metal reagent is 0.1 to 5 times (molar ratio), preferably 0.5 to 2 times that of the compound V. The reacting temperature of the above reaction may be vary in the range of a certain width, typically from −50° C. to 50° C., preferably from −40° C. to 25° C. The reaction time may vary depending on the solvent and reaction temperature, and is usually preferably 2 to 10 hours.

Said inert solvent is C1-C4 halogenated hydrocarbons, C6-C8 aromatic hydrocarbons, C2-C6 ether, C2-C6 nitrile, preferably dichloromethane, tetrahydrofuran, acetonitrile.

(3) In step c, the α-methylation reaction is conducted between a compound of formula III and hydrocarbylation reagent in the presence of strong base or Lewis acid, and the resultant is post-treated by a conventional method to give the compound I; said hydrocarbylation reagent is any one of methyl iodide, methyl bromide, methyl chloride, methyl trifluoromethanesulfonate, methyl benzenesulfonate, methyl fluorosulfonate; said strong base is any one of sodium hexamethyldisilylamide (NaHMDS), lithium hexamethyldisilylamide (LiHMDS), potassium hexamethyldisilylamide (KHMDS), lithium amide, sodium amide, potassium amide, lithium diisopropylamide (LDA), n-butyl lithium; said Lewis acid is any one of titanium tetrachloride, aluminum trichloride, ferric trichloride, zinc chloride, antimony pentafluoride.

A preferred embodiment of the present invention is as follows:

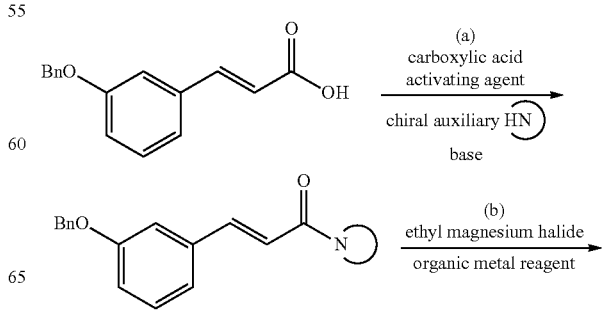

-continued

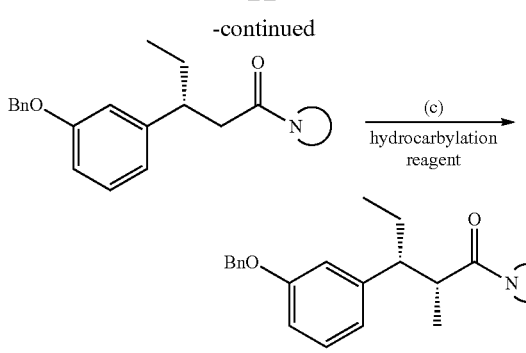

Another preferred embodiment of the present invention is as follows:

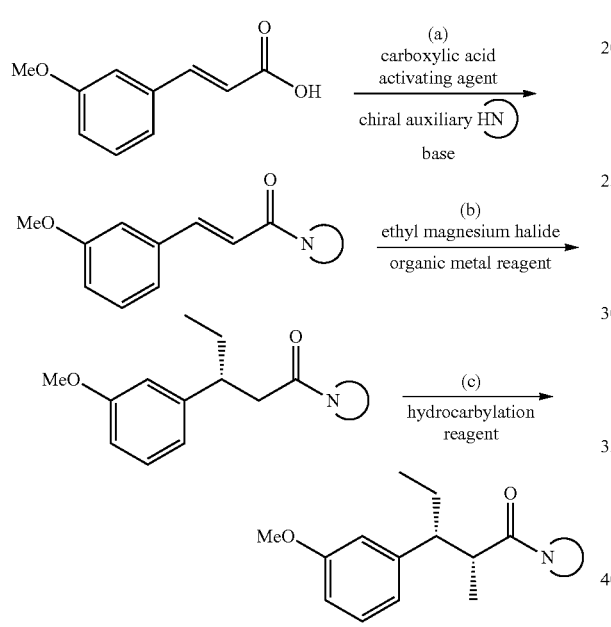

The present invention also provides another method for preparing (2R,3R)-3-(3-substituted phenyl)-2-methyl n-pentanamide compound of formula I, said method comprises: trans-pent-2-enoic acid VI is reacted with a chiral auxiliary

under the activation of a carboxylic acid activating agent to obtain a compound VII; the compound VII is subjected to an asymmetric Michael addition with 3-hydroxy protected phenyl magnesium halide under the condition of organic metal reagent in an inert solvent, then the resultant is post-treated by a conventional method to give a compound VIII; the chiral auxiliary is removed from the compound VIII to give a compound IX; then the compound IX is reacted with a chiral auxiliary

under the activation of a carboxylic acid activating agent to obtain a compound III; the compound III and hydrocarbylation reagent are conducted the α-methylation reaction in the presence of strong base or Lewis acid, then the resultant is post-treated by a conventional method to give the compound I. The method is shown as Reaction Scheme 6:

Reaction Scheme 6

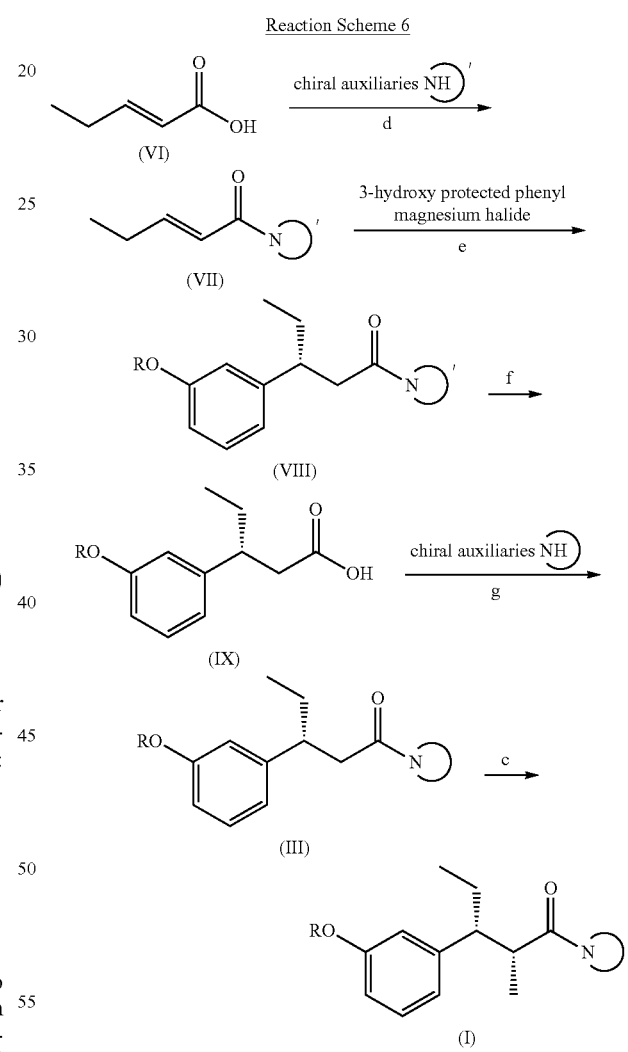

Wherein, R and are as defined above;

is the residue of chiral auxiliaries, which is defined as follows:

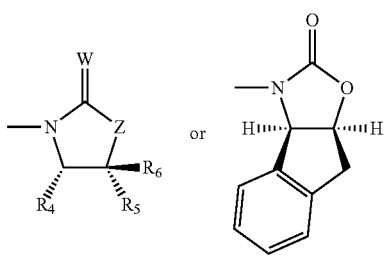

wherein, Z is O, S or $NR_8$, wherein $R_8$ is hydrogen, C1-C6 branched or linear alkyl;

W is O or S;

$R_4$ is C1-C6 alkyl, substituted or unsubstituted phenyl (Ph), substituted or unsubstituted naphthyl, substituted or unsubstituted benzyl (Bn), C1-C6 alkoxycarbonyl, wherein, the substituent on phenyl, naphthyl or benzyl group is 1 to 3 substituent(s) selected from hydroxy, halogen, C1-C6 alkyl and C1-C6 alkoxy;

$R_5$ and $R_6$ are each independently selected from H; C1-C6 alkyl; phenyl; phenyl substituted with 1 to 3 substituent(s) selected from hydroxy, halogen, C1-C6 alkyl and C1-C6 alkoxy.

The method comprises the following steps:

(1) In step d, trans-pent-2-enoic acid VI is reacted in the presence of carboxylic acid activating agent, chiral auxiliaries

and base, and with a suitable organic solvent and suitable temperature to form Compound VII.

The carboxylic acid activating agent is any one of thionyl chloride, oxalyl chloride, pivaloyl chloride, chloroformate and carbodiimides such as dicyclohexyl carbodiimide (DCC), 4-dimethylaminopyridine (DMAP) and carbonyldiimidazole (CDI);

said base may be inorganic base or organic base, and may be any one selected from sodium hydride, potassium hydride, alkyl lithium (n-butyl lithium or t-butyl lithium), lithium amide, sodium amide, potassium amide, lithium diisopropylamide (LDA), lithium hexamethyldisilylamide (LiHMDS), sodium hexamethyldisilylamide (NaHMDS), sodium methoxide, sodium ethoxide, potassium tert-butoxide, sodium hydroxide, potassium hydroxide, calcium hydroxide, triethylamine, ethylenediamine, sodium carbonate, potassium carbonate, sodium bicarbonate and potassium bicarbonate;

Said organic solvent includes: hydrocarbons, such as benzene, xylene, toluene, dichloromethane, chloroform; ethers such as tetrahydrofuran, diethyl ether, dipropyl ether, 1,4-dioxane; amides such as N,N-dimethylformamide, N,N-diethylformamide, N,N-dimethylacetamide; nitriles such as acetonitrile; and the mixtures of the above solvents, wherein, the preferred solvent is tetrahydrofuran, toluene, N,N-dimethylformamide or acetonitrile;

The reaction temperature is usually in the range of $-100°$ C. to $50°$ C., preferably $-80°$ C. to $30°$ C.

(2) In step e, the inert solution of the compound VII is slowly added to the mixed solution of Grignard reagent 3-hydroxy protected phenyl magnesium halide and organic metal reagent at a suitable temperature, after the reaction was complete, the resultant was post-treated by a conventional method to give the product VIII.

Said organic metal reagent is any one of cuprous bromide dimethylsulfide, cuprous bromide, cuprous chloride and cuprous iodide. The Grignard Reagent 3-hydroxy protected phenyl magnesium halide is any one selected from 3-hydroxy protected phenyl magnesium bromide, 3-hydroxy protected phenyl magnesium iodide and 3-hydroxy protected phenyl magnesium chloride. The amount of the Grignard reagent is 1 to 10 times (molar ratio), preferably 1 to 4 times that of the compound VII. The amount of the organic metal reagent is 0.1 to 5 times (molar ratio), preferably 0.5 to 2 times that of the compound VII. The reacting temperature of the above reaction may be vary in a certain range, typically from $-50°$ C. to $50°$ C., preferably from $-40°$ C. to $25°$ C. The reaction time may vary depending on the solvent and reaction temperature, and is usually preferably 2 to 10 hours.

Said inert solvent is C1-C4 halogenated hydrocarbon, C6-C8 aromatic hydrocarbon, C2-C6 ether, C2-C6 nitrile, preferably dichloromethane, tetrahydrofuran, acetonitrile.

(3) In step f, the chiral auxiliary residue

is removed from the compound VIII in the presence of hydrogen peroxide and an alkali metal hydroxide, said alkali metal hydroxide is any one selected from lithium hydroxide, sodium hydroxide and potassium hydroxide.

(4) In step g, the compound IX is reacted in the presence of carboxylic acid activating agent, chiral auxiliaries

and base, and with a suitable organic solvent and suitable temperature to form Compound III.

The carboxylic acid activating agent is any one of thionyl chloride, oxalyl chloride, pivaloyl chloride, chloroformate and carbodiimides such as dicyclohexyl carbodiimide (DCC), 4-dimethylaminopyridine (DMAP) and carbonyldiimidazole (CDI);

said base may be inorganic base or organic base, and may be any one selected from sodium hydride, potassium hydride, alkyl lithium (n-butyl lithium or t-butyl lithium), lithium amide, sodium amide, potassium amide, lithium diisopropylamide (LDA), lithium hexamethyldisilylamide (LiHMDS), sodium hexamethyldisilylamide (NaHMDS), sodium methoxide, sodium ethoxide, potassium tert-butoxide, sodium hydroxide, potassium hydroxide, calcium hydroxide, triethylamine, ethylenediamine, sodium carbonate, potassium carbonate, sodium bicarbonate and potassium bicarbonate;

Said organic solvent includes: hydrocarbons, such as benzene, xylene, toluene, dichloromethane, chloroform; ethers such as tetrahydrofuran, diethyl ether, dipropyl ether, 1,4-dioxane; amides such as N,N-dimethylformamide, N,N-diethylformamide, N,N-dimethylacetamide; nitriles such as acetonitrile; and the mixtures of the above solvents, wherein, the preferred solvent is tetrahydrofuran, toluene, N,N-dimethylformamide or acetonitrile;

The reaction temperature is usually in the range of −100° C. to 50° C., preferably −80° C. to 30° C.

(5) In step c, a α-methylation reaction is conducted between a compound of formula III and hydrocarbylation reagent in the presence of strong base or Lewis acid, and the resultant is post-treated by a conventional method to give the compound I;

said hydrocarbylation agent is any one of methyl iodide, methyl bromide, methyl chloride, methyl trifluoromethanesulfonate, methyl benzenesulfonate, methyl fluorosulfonate; said strong base is any one of sodium hexamethyldisilylamide (NaHMDS), lithium hexamethyldisilylamide (LiHMDS), potassium hexamethyldisilylamide (KHMDS), lithium amide, sodium amide, potassium amide, lithium diisopropylamide (LDA), n-butyl lithium; said Lewis acid is any one of titanium tetrachloride, aluminum trichloride, ferric trichloride, zinc chloride, antimony pentafluoride.

A preferred embodiment of the present invention is as follows:

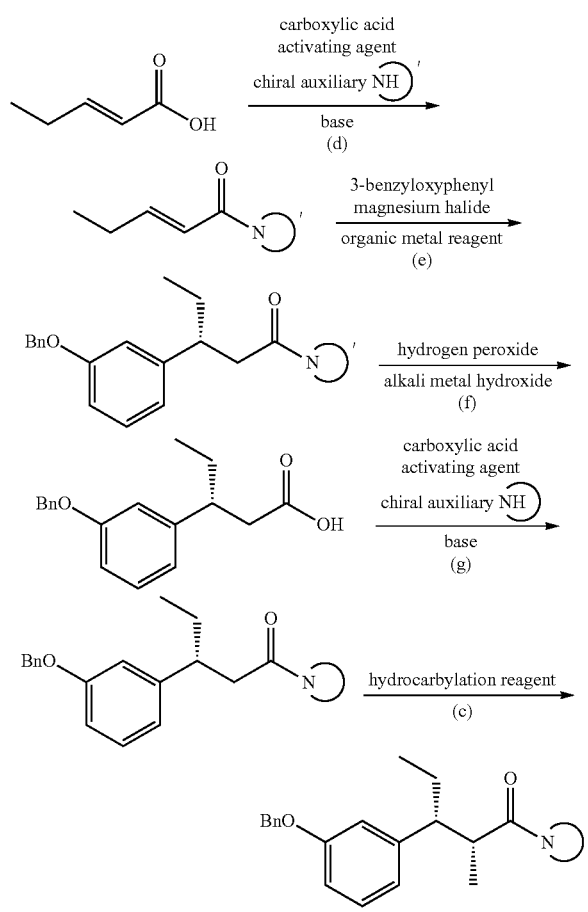

Another preferred embodiment of the present invention is as follows:

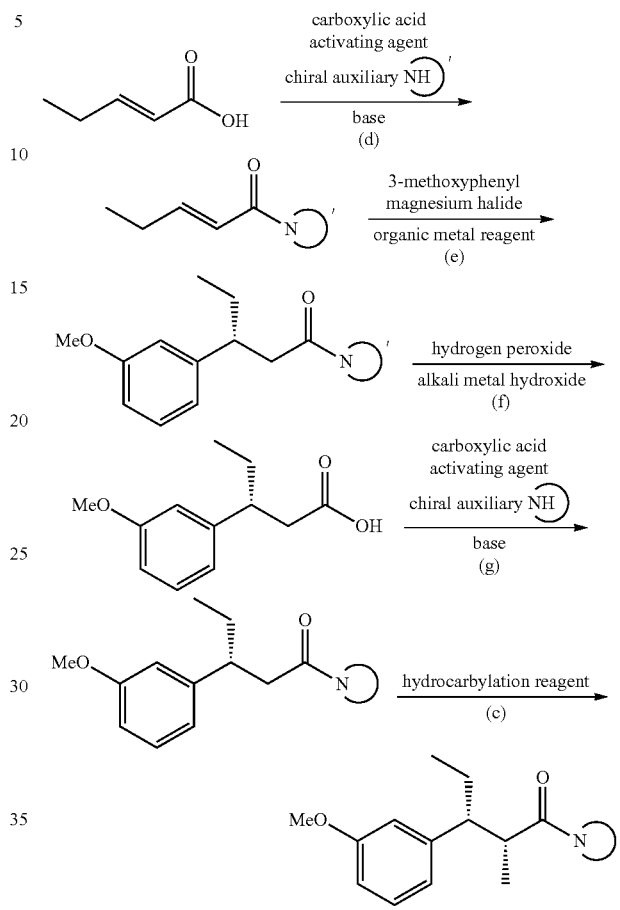

The invention also relates to a use of (2R,3R)-3-(3-substituted phenyl)-2-methyl n-pentanamide compound as shown in formula I, characterized in that, (2R,3R)-3-(3-substituted phenyl)-2-methyl n-pentanamide compound as shown in formula I can be used for preparing tapentadol or its pharmaceutically acceptable salt according to the following method.

(1) The chiral auxiliary residue

of the compounds as shown in formula I is removed to give compound X; compound X is subjected to the amidation reaction with dimethylamine or its salt under the activation of a carboxylic acid activating agent to give compound XI; compound XI is subjected to carbonyl reduction in a suitable reducing agent and a suitable solvent to give compound XII, then the protection group of the phenolic hydroxy group thereon is removed to give tapentadol II; if necessary, the tapentadol may be dissolved in a solvent, and then a suitable acid may be added therein to give a pharmaceutically acceptable salt of tapentadol; or after the protection group of the phenolic hydroxy group is removed, an appropriate acid is directly added therein without separation to give a pharmaceutically acceptable salt of tapentadol, as shown in Reaction Scheme 7:

Reaction Scheme 7:

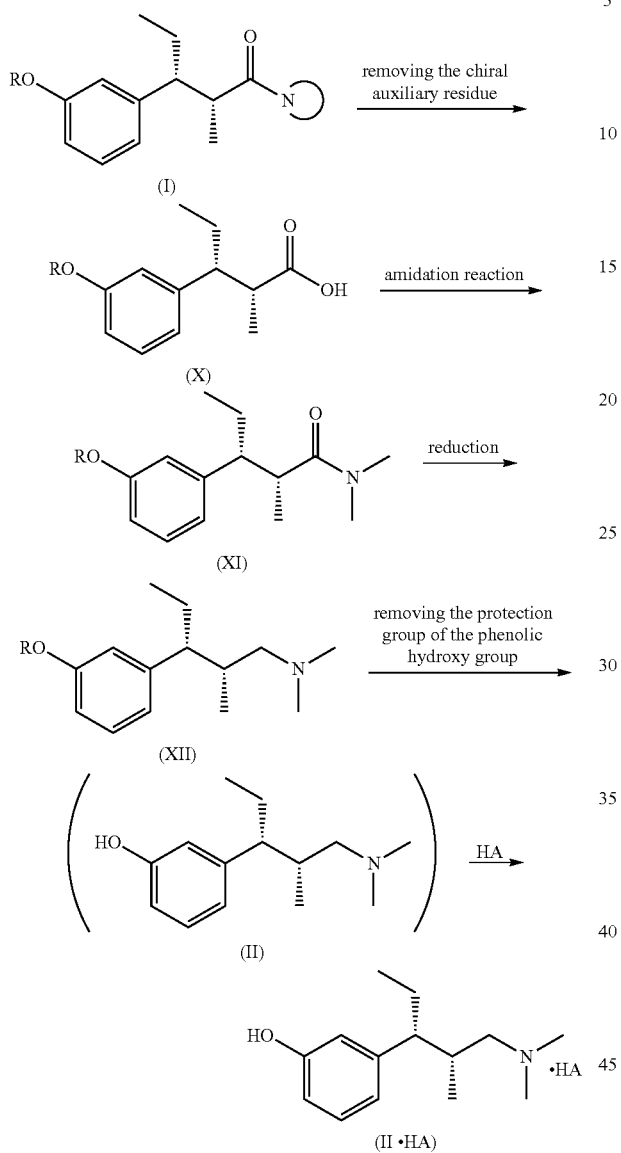

or:
(2) The chiral auxiliary residue

of the compounds as shown in formula I is removed to give compound X; compound X is subjected to the amidation reaction with dimethylamine or its salt under the activation of a carboxylic acid activating agent to give compound XI; the protection group of the phenolic hydroxy group on compound XI is removed to give compound XIII, compound XIII is reacted in a suitable reducing agent and a suitable solvent to give tapentadol II; if necessary, the tapentadol may be dissolved in a solvent, and then a suitable acid is added to give a pharmaceutically acceptable salt of tapentadol; or after the carbonyl group is reduced, an appropriate acid is directly added therein without separation to give a pharmaceutically acceptable salt of tapentadol, as shown in Reaction Scheme 8:

Reaction Scheme 8:

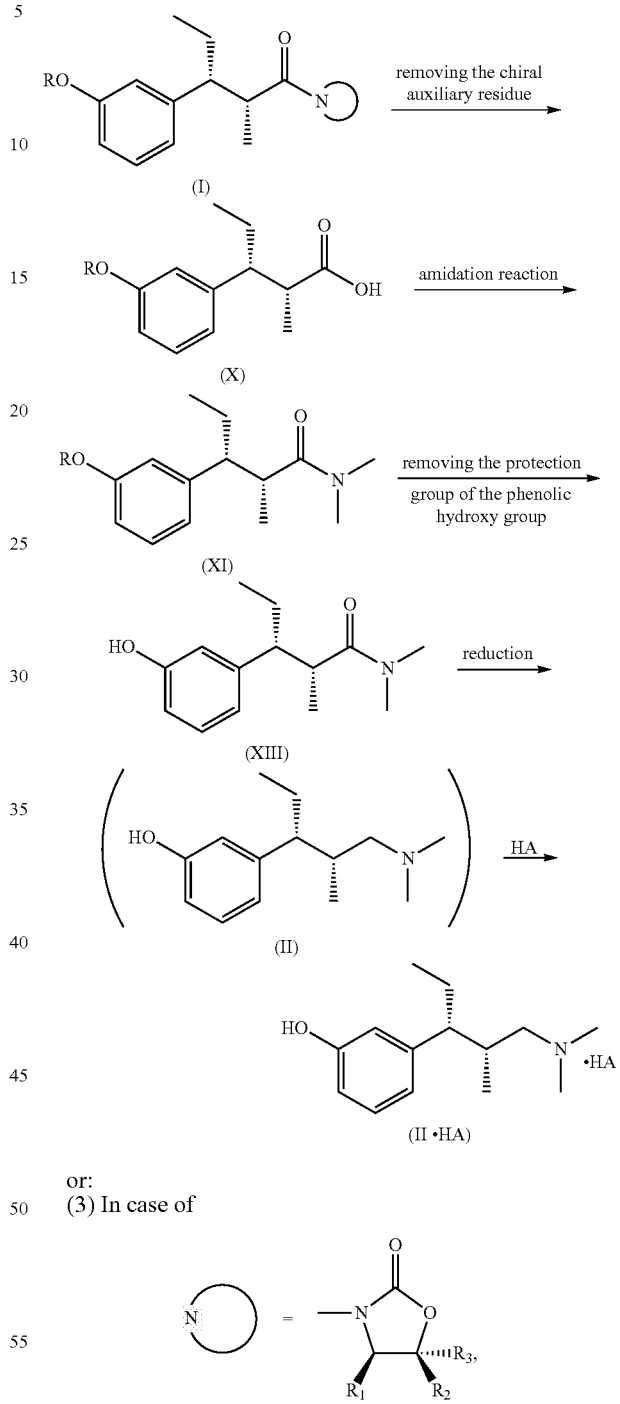

or:
(3) In case of

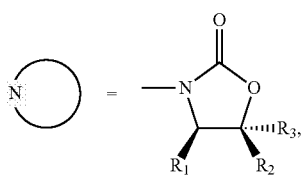

the substituents R1 to R3 is the same as those defined in the compounds of the formula I, the lactone in the chiral auxiliary residue in the compounds of formula I is hydrolyzed to give compound XIV, and carbonyl group on compound XIV IS reduced to give compound XV, then the protection group on phenolic hydroxy group and the substituents on the amino group are removed to give a primary amine compound XVI, finally it is methylated to give tapentadol; if necessary, the tapentadol may be dissolved in a solvent, and then a suitable acid is added to give a pharmaceutically acceptable salt of tapentadol; or after the methylation reaction, an appropriate acid is directly added therein without separation to give a pharmaceutically acceptable salt of tapentadol, as shown in Reaction Scheme 9:

Reaction Scheme 9:

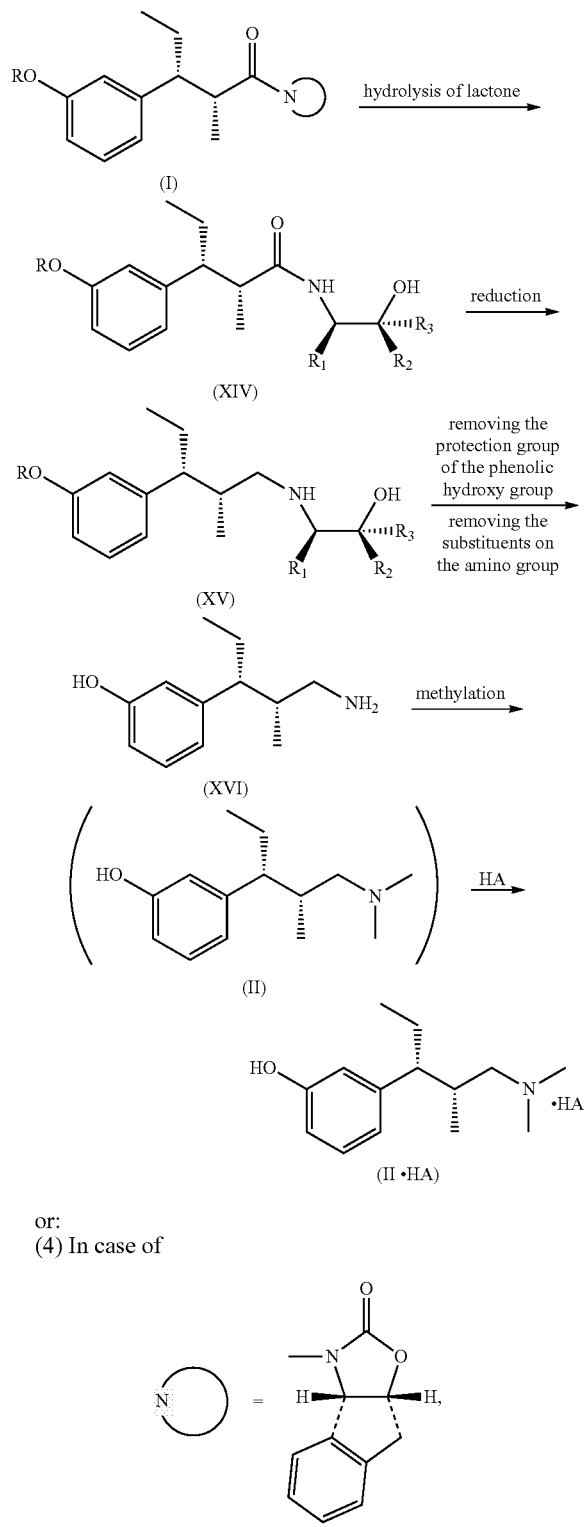

or:
(4) In case of the lactone in the chiral auxiliary residue in the compounds of formula I is hydrolyzed to give compound XVII, and carbonyl group on compound XVII is reduced to give compound XVIII, then the protection group on phenolic hydroxy group and the substituents on the amino group are removed to give a primary amine compound XVI, finally it is methylated to give tapentadol; if necessary, the tapentadol may be dissolved in a solvent, and then a suitable acid is added to give a pharmaceutically acceptable salt of tapentadol; or after the methylation reaction, an appropriate acid is directly added without separation to give a pharmaceutically acceptable salt of tapentadol, as shown in Reaction Scheme 10:

Reaction Scheme 10:

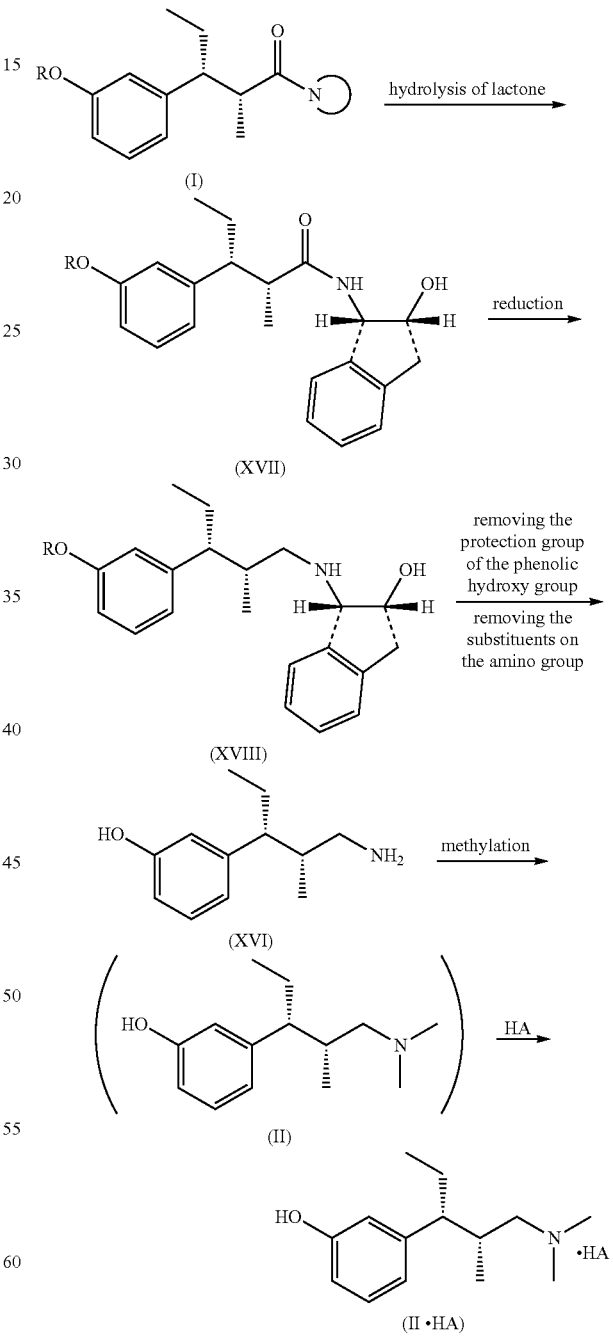

or:
(5) The compounds of formula I are reduced to give compound XIX, the hydroxy of compound XIX is converted to a leaving group LV to give compound XX, and compound XX is reacted with dimethylamine or its salt to give compound XII, then the protection group of the phenolic hydroxy group is removed to give tapentadol II; if necessary, the tapentadol may be dissolved in a solvent, and then a suitable acid is added to give a pharmaceutically acceptable salt of tapentadol; or after removing the protection group of the phenolic hydroxy group, an appropriate acid is directly added therein without separation to give a pharmaceutically acceptable salt of tapentadol, as shown in Reaction Scheme 11:

Reaction Scheme 11:

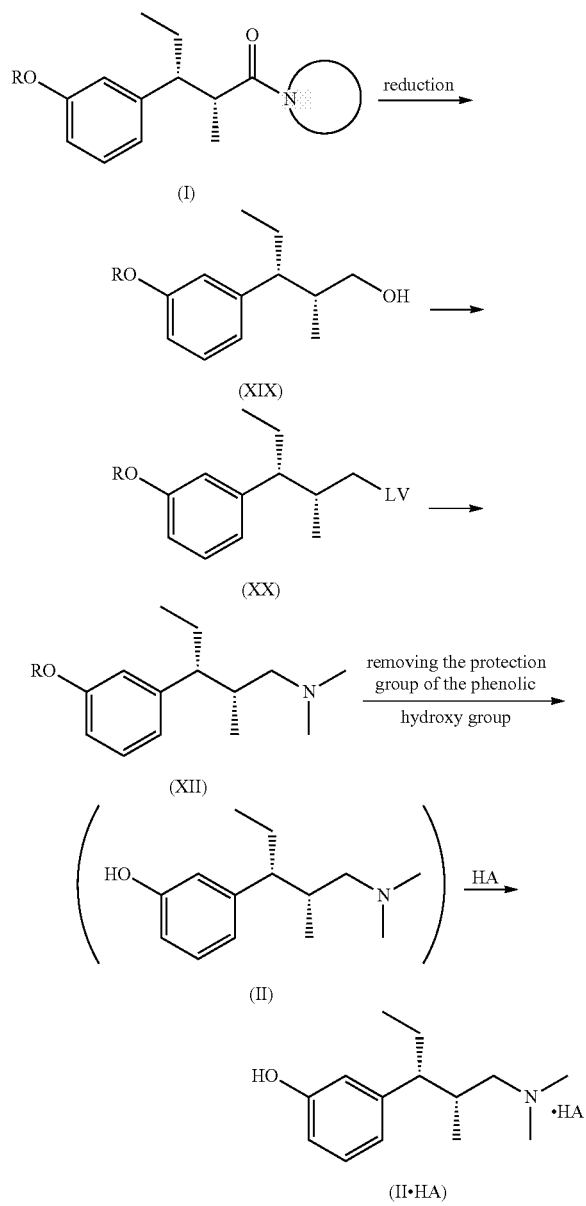

Wherein, LV represents a leaving group such as halogen, mesyl, phenylsulfonyl, substituted phenylsulfonyl (such as p-tolylsulfonyl) and the like;

In the above method of preparing the tapentadol or its pharmaceutically acceptable salt, the condition of removing the chiral auxiliary residue may be in the presence of hydrogen peroxide and an alkali metal hydroxide. Said alkali metal hydroxide is any one of lithium hydroxide, sodium hydroxide and potassium hydroxide. The condition of amidation reaction may be: compound X is reacted with dimethylamine or its salt under the action of a carboxylic acid activating agent to give compound XI. The used carboxylic acid activating agent is any one of thionyl chloride, oxalyl chloride, pivaloyl chloride, chloroformate, carbodiimides such as dicyclohexyl carbodiimide (DCC), 4-dimethylaminopyridine (DMAP) and carbonyldiimidazole (CDI); said reduction conditions may be: the reducing agent is any one of lithium aluminum tetrahydride, sodium borohydride/cobaltic chloride, boron trifluoride diethyl ether and zinc chloride; the solvent is diethyl ether, tetrahydrofuran, methanol and the like; said reaction of removing the protection group of phenolic hydroxy group is conducted as the conventional methods depending on the protection groups. For example: when R is benzyl or substituted benzyl, it may be removed in hydrochloric acid, the concentration range of the hydrochloric acid is selected from 5% to 36%; or it may be removed in the presence of palladium on carbon, formic acid and ammonium formate; alternatively, it may be removed by hydrogenation in an organic solvent in the presence of a metal catalyst, and the metal catalyst may be palladium on carbon, Raney nickel or platinum dioxide; and when R is methyl, it may be removed with hydrobromic acid or boron tribromide. The hydrolysis of lactone is under the alkaline condition, the base may be selected from an inorganic or organic base, for example, the inorganic base may be lithium hydroxide, potassium hydroxide, sodium hydroxide, etc.; the organic base may be sodium methoxide, sodium ethoxide, etc.; substituents on the amino group may be removed by hydrogenation in an organic solvent and in the presence of a metal catalyst, the metal catalyst may be palladium on carbon, Raney nickel or platinum dioxide; said methylation reaction may be conducted in the presence of formaldehyde and formic acid; the reaction conditions of converting the hydroxy of the compound XIX to a leaving group is as the conventional methods depending on the protection groups. For example, when the LV is halogen, the reaction is conducted using the corresponding halogenated reagent, such as thionyl chloride, hydrobromic acid, etc.; when the LV is a sulfonyl group, the reaction is conducted using the corresponding sulfonyl chloride under alkaline conditions; the reaction of said compound XX with dimethylamine or its salt is carried out under alkaline conditions. The acid radical of said pharmaceutically acceptable salt of tapentadol may be from inorganic or organic acid, it is characterized in that, the inorganic acid is one of hydrochloric acid, nitric acid, phosphoric acid, sulfuric acid, hydrobromic acid and hydroiodic acid; the organic acid is one of formic acid, acetic acid, propionic acid, butyric acid, malic acid, tartaric acid, amino acid, methanesulfonic acid, benzenesulfonic acid, p-toluenesulfonic acid, naphthalenesulfonic acid, camphorsulfonic acid, taurine, fumaric acid, maleic acid, citric acid, succinic acid, cholic acid and deoxycholic acid.

A preferred embodiment of the present invention is as follows:

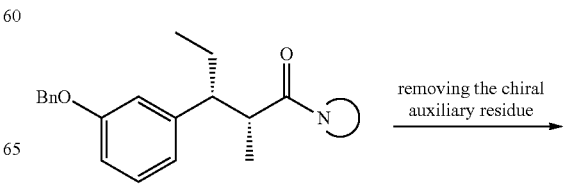

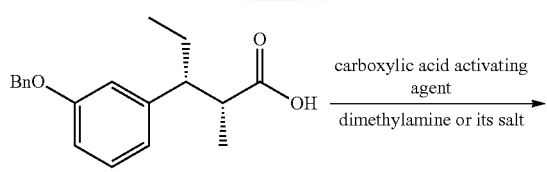
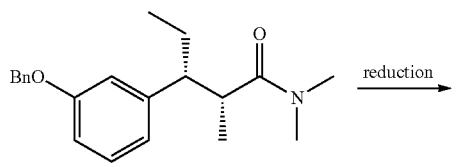
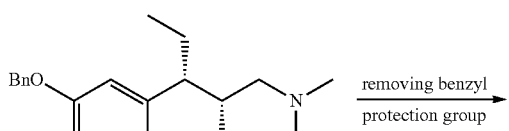
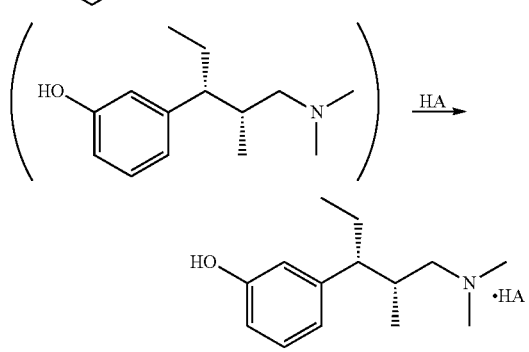
Another preferred embodiment of the present invention is as follows:
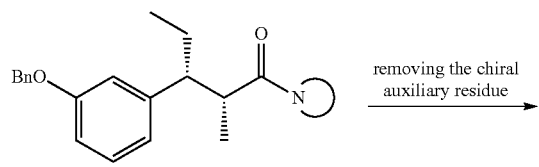
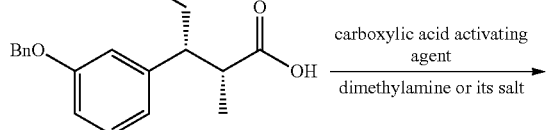
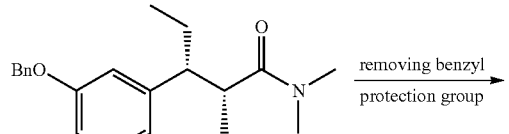
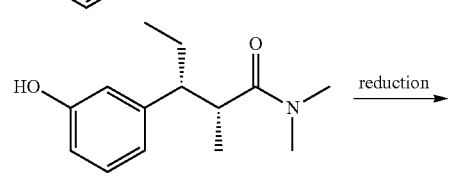
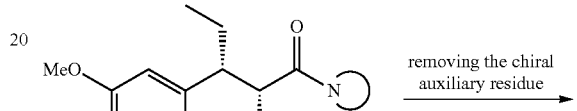
Another preferred embodiment of the present invention is as follows:
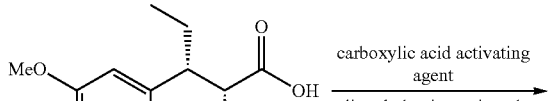
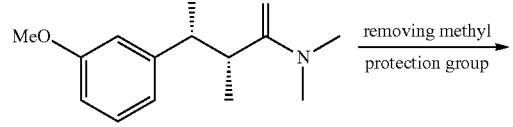
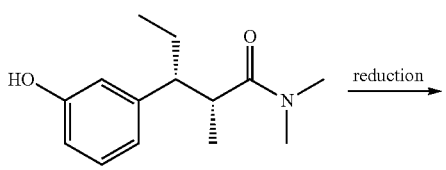
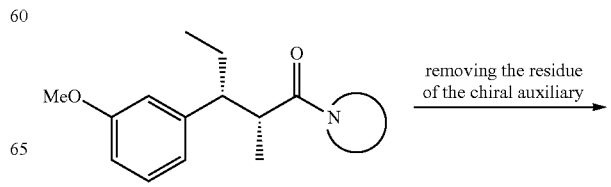
Another preferred embodiments of the present invention is as follows:

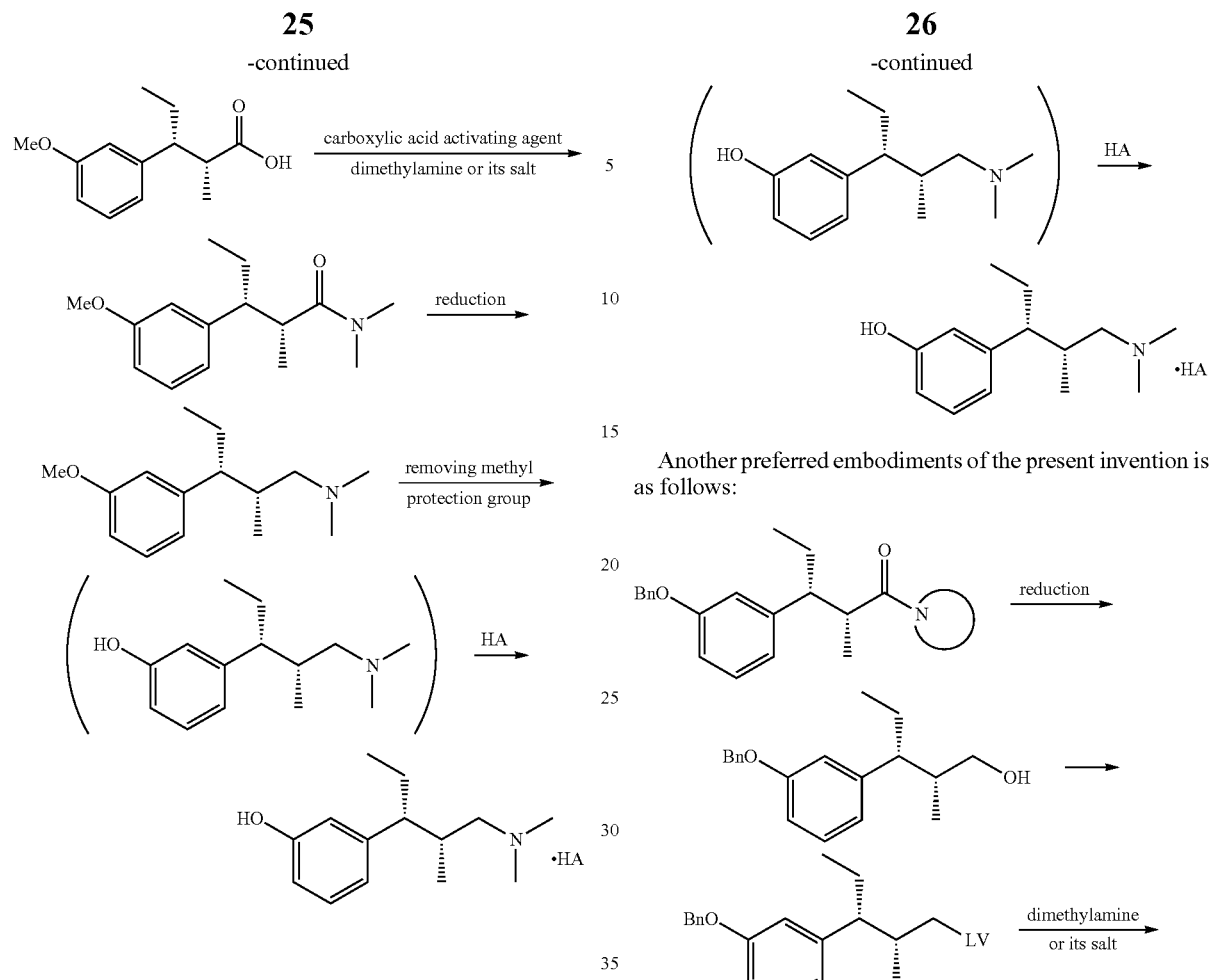
Another preferred embodiment of the present invention is as follows:
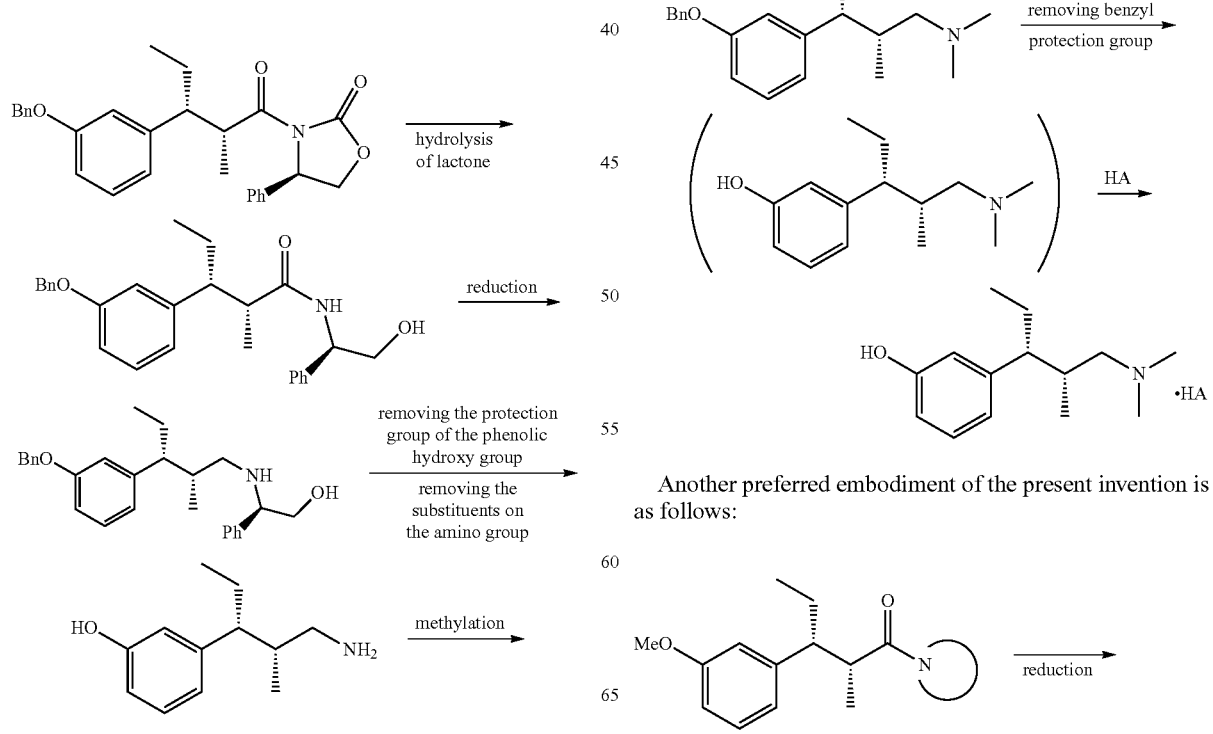
Another preferred embodiments of the present invention is as follows:
Another preferred embodiment of the present invention is as follows:

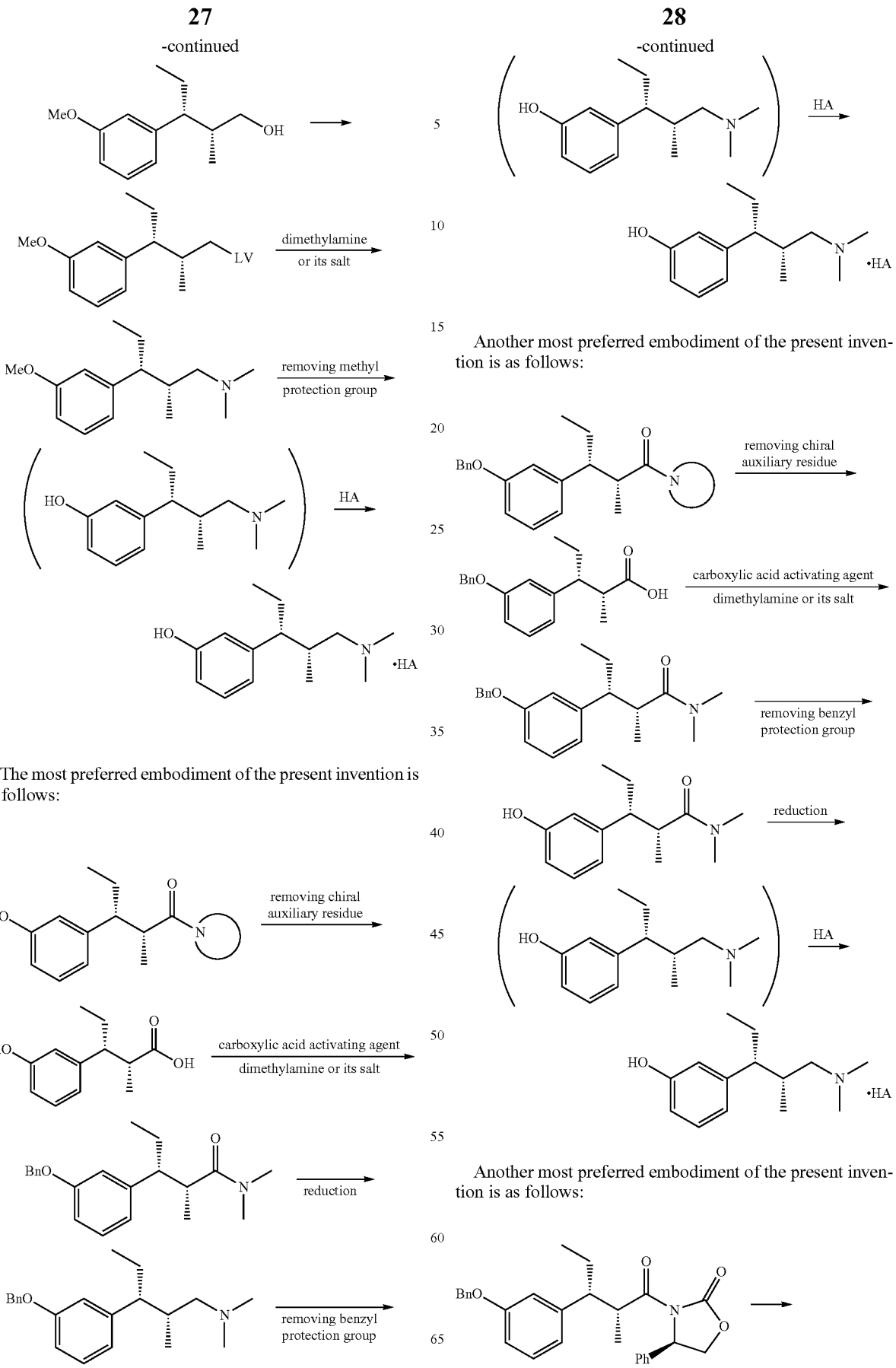
The most preferred embodiment of the present invention is as follows:
Another most preferred embodiment of the present invention is as follows:
Another most preferred embodiment of the present invention is as follows:

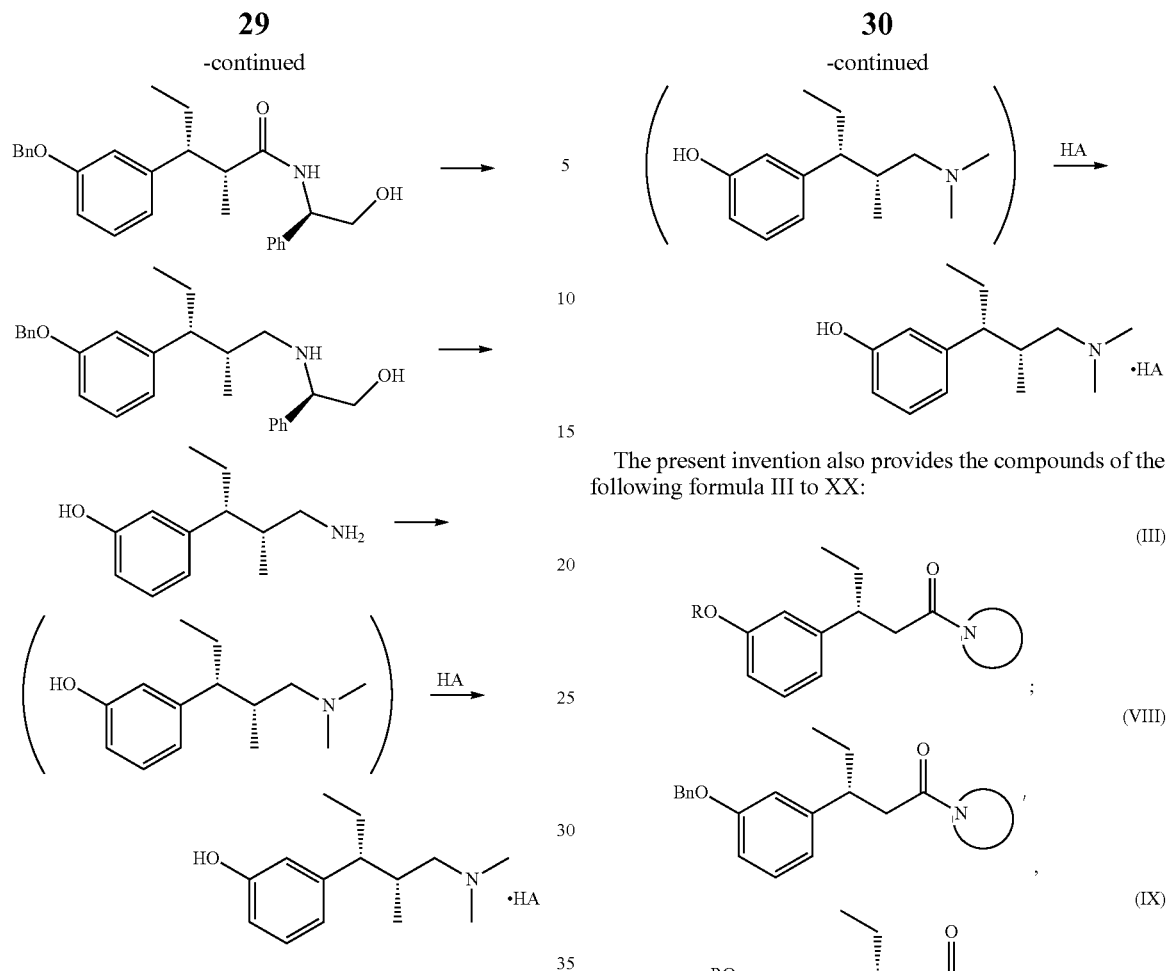
Another most preferred embodiment of the present invention is as follows:
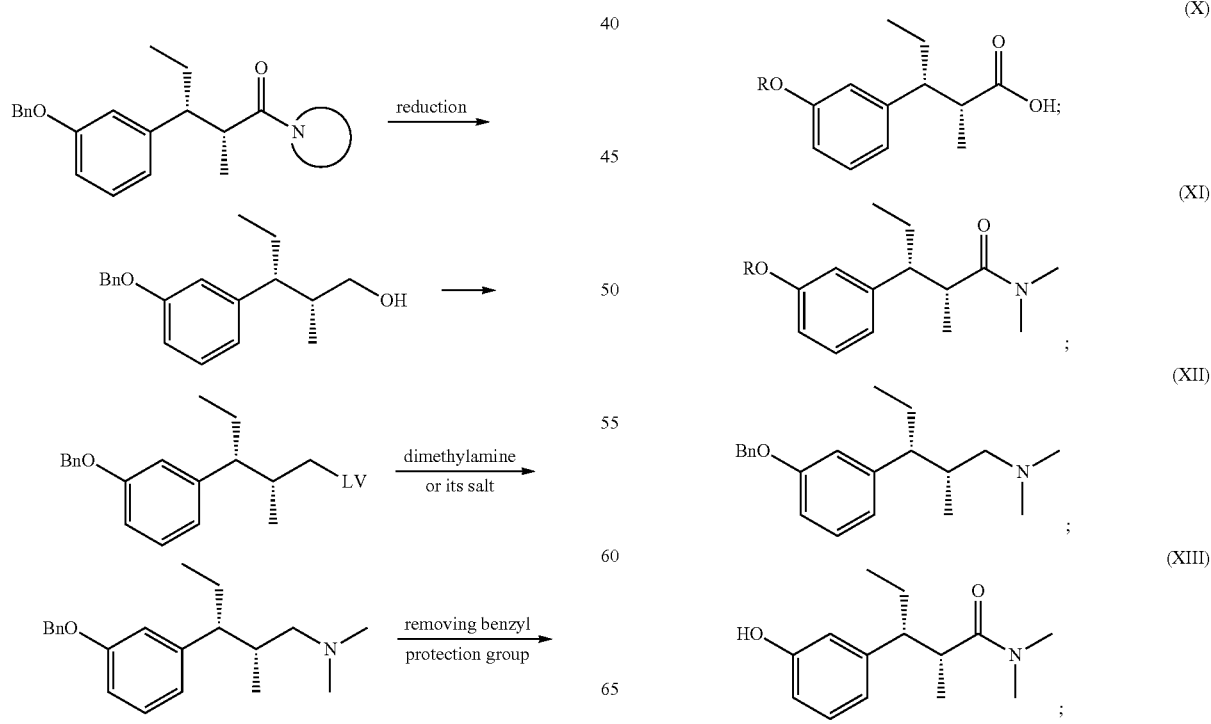
The present invention also provides the compounds of the following formula III to XX:

-continued

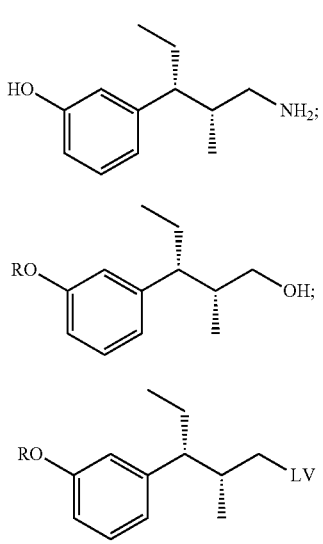

(XVI)

(XIX)

(XX)

wherein, R is the protecting group of the phenolic hydroxy, R can form an ether group or an ester group with the phenolic hydroxy; R may be selected from C1-C6 linear or branched alkyl, substituted or unsubstituted aryl, substituted or unsubstituted arylalkyl, alkylsilyl, C1-C6 alkoxymethyl, C1-C6 alkyloyl, substituted or unsubstituted aryloyl; wherein, said substituents may be hydroxyl, halogen, C1-C6 alkyl, C1-C6 alkoxy etc.; said aryl may be phenyl, naphthyl etc.;

LV represents a leaving group such as halogen, mesyl, phenylsulfonyl, substituted phenylsulfonyl and the like;

is the chiral auxiliary residue, which is defined as follows:

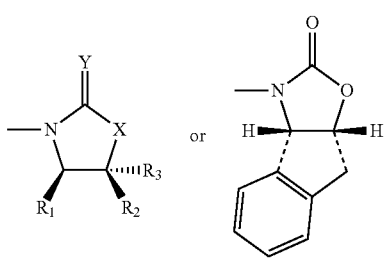

wherein, X is O, S or $NR_7$, wherein $R_7$ is hydrogen, C1-C6 branched or linear alkyl; Y is O or S;

$R_1$ is C1-C6 alkyl group, substituted or unsubstituted phenyl (Ph), substituted or unsubstituted naphthyl, substituted or unsubstituted benzyl (Bn), C1-C6 alkoxycarbonyl, wherein, the substituent on phenyl, naphthyl or benzyl group is 1 to 3 substituent(s) selected from C1-C6 alkyl and hydroxy;

$R_2$ and $R_3$ are each independently selected from H, C1-C6 alkyl and phenyl;

is chiral auxiliary residue, which is defined as follows:

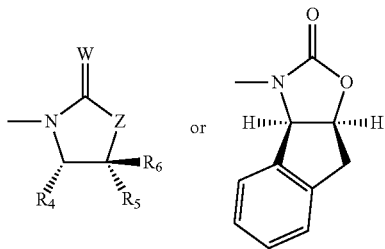

wherein, Z is O, S or $NR_8$, wherein $R_8$ is hydrogen, C1-C6 branched or linear alkyl; W is O or S;

$R_4$ is C1-C6 alkyl group, substituted or unsubstituted phenyl (Ph), substituted or unsubstituted naphthyl, substituted or unsubstituted benzyl (Bn), C1-C6 alkoxycarbonyl, wherein the substituent on phenyl, naphthyl or benzyl group is 1 to 3 substituent(s) selected from hydroxy, halogen, C1-C6 alkyl and C1-C6 alkoxy;

$R_5$ and $R_6$ are each independently selected from H; C1-C6 alkyl; phenyl; phenyl substituted with 1 to 3 substituent(s) selected from hydroxy, halogen, C1-C6 alkyl and C1-C6 alkoxy.

In the preferred compound of the present invention, R is benzyl, methyl, t-butyl, triphenylmethyl, methoxymethyl, trimethylsilyl, t-butyldimethylsilyl, acetyl or benzoyl;

LV is bromine, iodine, chlorine, mesyl, phenylsulfonyl, substituted phenylsulfonyl and the like;

X is O; and Y is O;

$R_1$ is C1-C6 alkyl group, substituted or unsubstituted phenyl (Ph), substituted or unsubstituted benzyl (Bn), wherein the substituent on phenyl or benzyl group is 1 to 3 substituent(s) selected from hydroxy, halogen, C1-C6 alkyl and C1-C6 alkoxy;

$R_2$ and $R_3$ are each independently selected from H, C1-C6 alkyl and phenyl;

W is O; Z is O;

$R_4$ is C1-C6 alkyl group, substituted or unsubstituted phenyl (Ph), substituted or unsubstituted benzyl (Bn), wherein the substituent on phenyl or benzyl group is 1 to 3 substituent(s) selected from hydroxy, halogen, C1-C6 alkyl and C1-C6 alkoxy;

$R_5$ and $R_6$ are each independently selected from H, C1-C6 alkyl and phenyl.

In a further preferred compound of the present invention, R is benzyl or methyl;

LV is bromine, iodine, chlorine, mesyl, p-tolylsulfonyl and the like;

X is O; and Y is O;

$R_1$ is phenyl; phenyl substituted with 1 to 3 substituent(s) selected from hydroxy, halogen, C1-C6 alkyl and C1-C6 alkoxy; or benzyl; $R_2$ and $R_3$ are each independently selected from H, C1-C6 alkyl and phenyl;

W is O; Z is O;

$R_4$ is phenyl; phenyl substituted with 1 to 3 substituent(s) selected from hydroxy, halogen, C1-C6 alkyl and C1-C6 alkoxy; or benzyl;

$R_5$ and $R_6$ are each independently selected from H, C1-C6 alkyl and phenyl.

More preferably, the compounds of the present invention are as follows:

(1) 3-[(3R)-1-oxo-3-[3-(phenylmethoxy)phenyl]pentyl]-4R-phenyl-2-Oxazolidinone

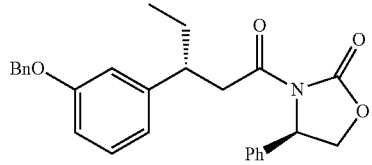 [SMILES: CC[C@H](CC(=O)N1C(=O)OC[C@H]1c1ccccc1)c1cccc(OCc2ccccc2)c1]

(2) 3-[(3R)-1-oxo-3-[3-(phenylmethoxy)phenyl]pentyl]-4R,5S-diphenyl-2-Oxazolidinone

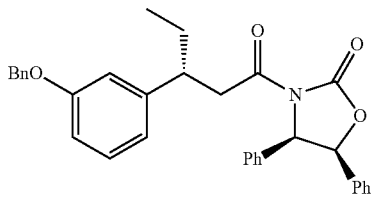 [SMILES: CC[C@H](CC(=O)N1C(=O)O[C@@H](c2ccccc2)[C@H]1c1ccccc1)c1cccc(OCc2ccccc2)c1]

(3) 3-[(3R)-3-(3-methoxyphenyl)-1-oxopentyl]-4R-phenyl-2-Oxazolidinone

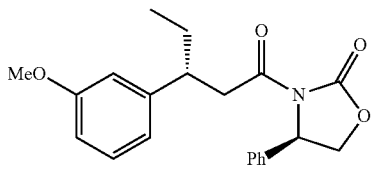 [SMILES: CC[C@H](CC(=O)N1C(=O)OC[C@H]1c1ccccc1)c1cccc(OC)c1]

(4) 3-[(3R)-3-(3-methoxyphenyl)-1-oxopentyl]-4R,5S-diphenyl-2-Oxazolidinone

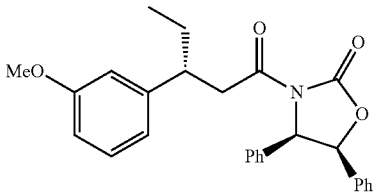 [SMILES: CC[C@H](CC(=O)N1C(=O)O[C@@H](c2ccccc2)[C@H]1c1ccccc1)c1cccc(OC)c1]

(5) 3-[(3R)-1-oxo-3-[3-(phenylmethoxy)phenyl]pentyl]-4S-phenyl-2-Oxazolidinone

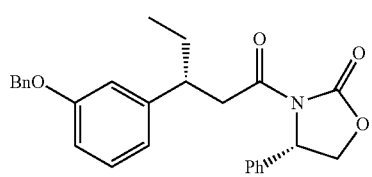 [SMILES: CC[C@H](CC(=O)N1C(=O)OC[C@@H]1c1ccccc1)c1cccc(OCc2ccccc2)c1]

(6) 3-[(3R)-1-oxo-3-[3-(phenylmethoxy)phenyl]pentyl]-4S,5R-diphenyl-2-Oxazolidinone

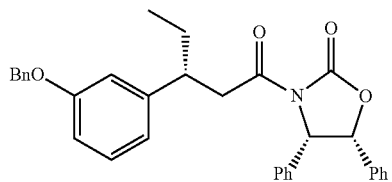 [SMILES: CC[C@H](CC(=O)N1C(=O)O[C@H](c2ccccc2)[C@@H]1c1ccccc1)c1cccc(OCc2ccccc2)c1]

(7) (βR)-ethyl-3-(phenylmethoxy)benzenepropanoic acid

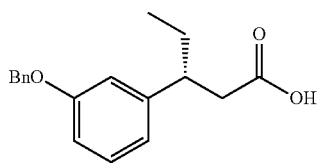 [SMILES: CC[C@H](CC(=O)O)c1cccc(OCc2ccccc2)c1]

(8) (βR)-ethyl-3-methoxybenzenepropanoic acid

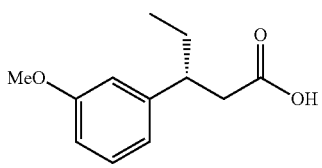

(9) (αR,βR)-β-ethyl-α-methyl-3-(phenylmethoxy)benzenepropanoic acid

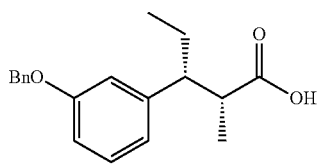 [SMILES: CC[C@@H](c1cccc(OCc2ccccc2)c1)[C@@H](C)C(=O)O]

(10) (αR,βR)-β-ethyl-3-methoxy-α-methylbenzenepropanoic acid

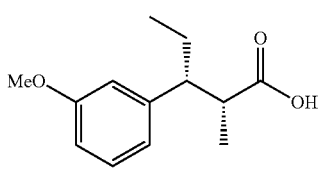 [SMILES: CC[C@@H](c1cccc(OC)c1)[C@@H](C)C(=O)O]

(11) (αR,βR)-β-ethyl-N,N,α-trimethyl-3-(phenylmethoxy)benzenepropanamide

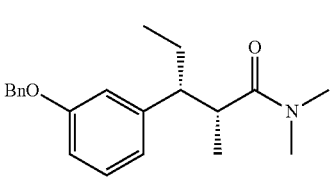

(12) (αR,βR)-β-ethyl-3-methoxy-N,N,α-trimethyl benzenepropanamide

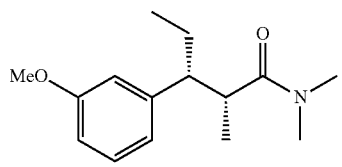 [SMILES: CC[C@@H](c1cccc(OC)c1)[C@@H](C)C(=O)N(C)C]

(13) (αR,βR)-β-ethyl-3-hydroxy-N,N,α-trimethylbenzenepropanamide

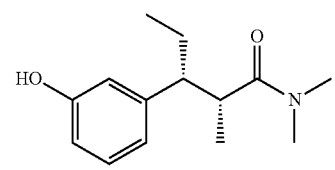 [SMILES: CC[C@@H](c1cccc(O)c1)[C@@H](C)C(=O)N(C)C]

(14) (βR,γR)-γ-ethyl-N,N,β-trimethyl-3-(phenylmethoxy)benzenepropanamine

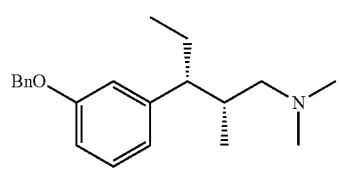 [SMILES: CC[C@@H](c1cccc(OCc2ccccc2)c1)[C@@H](C)CN(C)C]

(15) 3-[(1R,2R)-3-amino-1-ethyl-2-methylpropyl]phenol

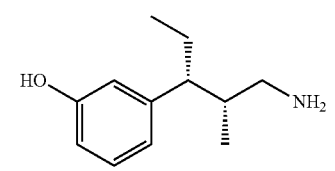

(16) (βR,γR)-γ-ethyl-β-methyl-3-(phenylmethoxy)benzenepropanol

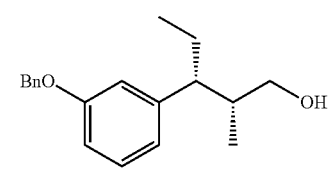

(17) (βR,γR)-γ-ethyl-3-methoxy-β-methylbenzenepropanol

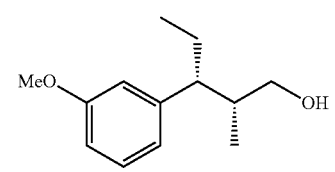

(18) (βR,γR)-γ-ethyl-β-methyl-3-(phenylmethoxy)benzenepropanol 1-methanesulfonate

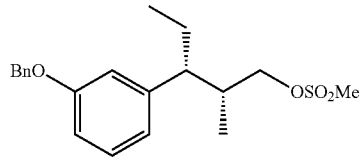

(19) (βR,γR)-γ-ethyl-3-methoxy-β-methylbenzenepropanol 1-methanesulfonate

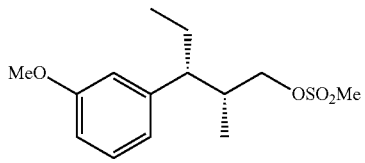

(20) (βR,γR)-γ-ethyl-β-methyl-3-(phenylmethoxy)benzenepropanol 1-(4-methylbenzenesulfonate)

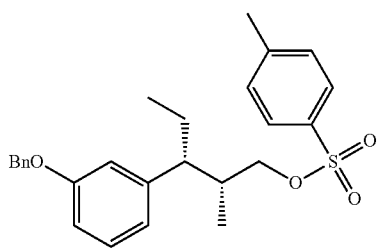 [SMILES: CC[C@@H](c1cccc(OCc2ccccc2)c1)[C@@H](C)COS(=O)(=O)c1ccc(C)cc1]

(21) 1-[(1R,2R)-3-chloro-1-ethyl-2-methylpropyl]-3-(phenylmethoxy)benzene

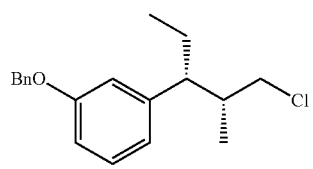 [SMILES: CC[C@@H](c1cccc(OCc2ccccc2)c1)[C@@H](C)CCl]

(22) 1-[(1R,2R)-3-bromo-1-ethyl-2-methylpropyl]-3-(phenylmethoxy)benzene

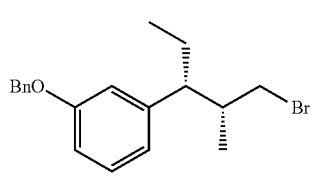 [SMILES: CC[C@@H](c1cccc(OCc2ccccc2)c1)[C@@H](C)CBr]

According to present invention, the new chiral centers is introduced via the stereoselective alkylation in a asymmetric Michael addition reaction controlled by chiral auxiliaries, to form a product which is easily purified by crystallization. The resulting intermediate and the final product have a high optical purity, and chiral auxiliaries have the characteristic of easy to be removed, configuration retention, and easier to recycle and use. The present method has the advantages of good reactivity, high stereo selectivity, high yield, simple operation, cheap and easy-to-get reagents, recyclable chiral auxiliaries etc., and it can be economically and conveniently used to realize industrial production of tapentadol or the pharmaceutically acceptable salt thereof.

DESCRIPTION OF THE PREFERRED EMBODIMENTS

Now the present invention is further described with reference to the following Examples, however, the Examples are not intended for any limitation of the invention.

Example 1

(R,E)-3-(3-(3-benzyloxy)phenyl)acryloyl)-4-phenyl oxazolidin-2-one

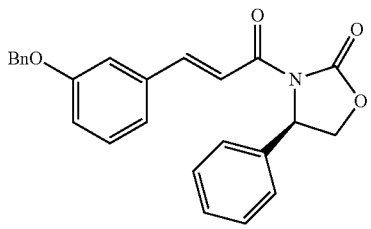 [SMILES: O=C(/C=C/c1cccc(OCc2ccccc2)c1)N1C(=O)OC[C@H]1c1ccccc1]

m-benzyloxy cinnamic acid (9.0 g, 35.4 mmol) was dissolved in thionyl chloride (25 ml) and refluxed for 1 hour, and the mixture was concentrated to remove thionyl chloride for further use. 4R-phenyl-2-oxazolidinone (5.6 g, 34.4 mmol) was placed in a three-necked flask, after it was purged with nitrogen, tetrahydrofuran (25 ml) was added and when it was cooled to −78° C., n-butyl lithium (1.6M, 22 ml, 35.4 mmol) was added dropwise, and the reaction was carried out for 30 minutes. Then the solution (35 ml) of m-benzyloxy cinnamoyl chloride in tetrahydrofuran as prepared above was added dropwise and the reaction was continued for 30 minutes. After that, it was slowly raised to 0° C., the reaction was continued for 2 hours, then it was quenched with saturated ammonium chloride solution. The resulted mixture was then concentrated to remove tetrahydrofuran and extracted with ethyl acetate for three times, then the organic phases were combined, washed with saturated brine, dried over anhydrous sodium sulfate, concentrated and recrystallized with petroleum ether and ethyl acetate to give a white solid 14 g, yield: 93%. $^1$HNMR (300 MHz, CDCl$_3$): δ 7.9 (1H, d, J=15.5), 7.7 (1H, d, J=15.3), 7.3-7.5 (11H, m), 7.2 (2H, m), 7.0 (1H, dd, J=2.3, 8.6), 5.6 (1H, dd, J=4.0, 9.0), 5.1 (2H, s), 4.8 (1H, t, J=8.9, 17.7), 4.3 (1H, dd, J=3.9, 8.8). ESI-MS: 422.2 (M+Na).

Example 2

3-[(3R)-1-oxo-3-[3-(phenylmethoxy)phenyl]pentyl]-4R-phenyl-2-Oxazolidinone

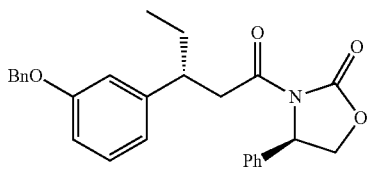 [SMILES: CC[C@H](CC(=O)N1C(=O)OC[C@H]1c1ccccc1)c1cccc(OCc2ccccc2)c1]

Cuprous bromide dimethyl sulfide complex (7.7 g, 37.5 mmol) was placed in a three-necked flask, after it was purged with nitrogen, tetrahydrofuran (25 ml) was added therein. When it was cooled to −40° C., ethyl magnesium bromide (2.5M, 30 ml, 75 mmol) was added dropwise, the reaction was carried out with stirring for 10 minutes, and the reaction solution became yellow; boron trifluoride diethyl ether (4.8 ml, 37.5 mmol) was added dropwise and the reaction was continued for 10 minutes; then the solution of the product of Example 1 (10 g, 25 mmol) in tetrahydrofuran was added dropwise, after the addition was complete, it was warmed to −15° C., and then gradually warmed to room temperature, the reaction was continued for 2 hours and quenched with saturated ammonium chloride solution, then the resulted mixture was concentrated to remove tetrahydrofuran. The reaction solution was diluted with ethyl acetate, filtered to remove insoluble material and separated, then the aqueous phase was extracted twice with ethyl acetate, the organic phases were combined and washed with 1N ammonia twice, then washed with water and saturated brine, dried over anhydrous sodium sulfate, concentrated and recrystallized with petroleum ether and ethyl acetate to obtain the target 9 g, yield: 85%, d.r.=99:1.

$^1$HNMR (300 MHz, CDCl$_3$): δ 7.3-7.5 (8H, m), 7.1-7.2 (3H, m), 6.7-6.9 (3H, m), 5.2 (1H, dd, J=3.7, 8.6), 5.1 (2H, s), 4.5 (1H, t, J=8.9, 17.1), 4.2 (1H, dd, J=3.5, 8.6), 3.5 (1H, dd, J=8.9, 16.4), 3.2 (1H, d, J=5.6), 3.1 (1H, m), 1.5-1.7 (2H, m), 0.9 (3H, t, J=7.3, 14.7). ESI-MS: 430.5 (M+H).

Example 3

3-[(2R,3R)-2-methyl-1-oxo-3-[3-(phenylmethoxy)phenyl]pentyl]-4R-phenyl-2-Oxazolidinone

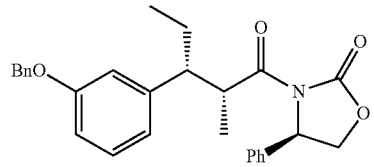 [SMILES: CC[C@@H](c1cccc(OCc2ccccc2)c1)[C@@H](C)C(=O)N1C(=O)OC[C@H]1c1ccccc1]

The product of Example 2 (8.6 g, 20 mmol) was placed in a double-necked flask, after it was purged with nitrogen, it was cooled to −78° C., then tetrahydrofuran (25 ml) was added. The solution of sodium hexamethyldisilylamide (NaHMDS) in tetrahydrofuran (2M, 10 ml, 20 mmol) was slowly added dropwise, and the reaction was carried out at −78° C. for 30 min; methyl iodide (2.5 ml, 40 mmol) was added, and the reaction was continued at −78° C. for 30 min, then it was slowly warmed to −50° C., and the reaction was continued for 1 hour and quenched with saturated ammonium chloride solution. Then the resulted mixture was concentrated to remove tetrahydrofuran and extracted with ethyl acetate for three times. The organic phases were combined, washed with saturated brine, dried over anhydrous sodium sulfate, concentrated and recrystallized with petroleum ether and ethyl acetate to give a white solid 7.5 g, yield: 85%, d.r.=99.9:0.1. $^1$HNMR (300 MHz, CDCl$_3$): δ 7.2-7.5 (11H, m), 6.7-6.9 (3H, m), 5.1 (2H, s), 4.8 (1H, dd, J=3.5, 7.5), 4.2-4.3 (1H, m), 3.9-4.0 (2H, m), 2.6 (1H, dt, J=3.7, 10.3), 1.8-2.0 (1H, m), 1.4-1.6 (1H, m), 1.2 (3H, d, J=7.2), 0.9 (3H, t, J=7.4, 14.7). ESI-MS: 444.4 (M+H).

Example 4

(αR,βR)-β-ethyl-α-methyl-3-(phenylmethoxy)benzenepropanoic acid

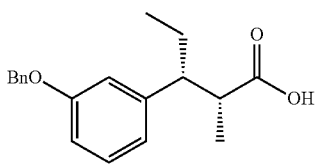

The product of Example 3 (6.6 g, 15 mmol) was dissolved in tetrahydrofuran/water (v/v=4/1), in an ice-water bath, hydrogen peroxide (30%, 1.9 ml, 60 mmol) and lithium hydroxide (574 mg, 24 mmol) aqueous solution were added dropwise in sequence, then it was slowly warmed to room temperature and the reaction was continued for 4 hours. Sodium sulfite aqueous solution (2.5M, 24 ml) was added dropwise to the reaction solution which was stirred for 10 minutes, concentrated to remove tetrahydrofuran, extracted with dichloromethane for three times, washed with water and saturated brine, dried over anhydrous sodium sulfate, concentrated and recovered to give 4R-phenyl oxazolidin-2-one 2.3 g. The pH of the aqueous phase was adjusted to appropriate 2 with 1N hydrochloric acid, and extracted with dichloromethane for three times, then the organic phases were combined, washed with saturated sodium bicarbonate solution and saturated brine, dried over anhydrous sodium sulfate, concentrated and recrystallized with petroleum ether and ethyl acetate to give a white solid 3.8 g, yield: 91%. $^1$HNMR (300 MHz, CDCl$_3$): δ 7.3-7.5 (5H, m), 7.2 (1H, t, J=7.6, 15.3), 6.7-6.9 (3H, m), 5.0 (2H, s), 2.8 (1H, m), 2.7 (1H, m), 1.7-1.8 (1H, m), 1.5-1.6 (1H, m), 1.1 (3H, d, 6.8), 0.9 (3H, t, J=7.3, 14.5). ESI-MS: 297.0 (M−H).

Example 5

(αR,βR)-β-ethyl-N,N,α-trimethyl-3-(phenylmethoxy)benzenepropanamide

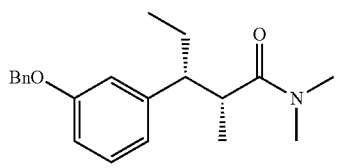

The product of Example 4 (3 g, 10 mmol) was dissolved in dichloromethane (10 ml), oxalyl chloride (2.6 ml, 30 mmol) was added dropwise, and it was reacted at room temperature for 1 hr, then the reaction solution was concentrated to give a pale yellow oil which was further dissolved in dichloromethane. And then the resulted solution was added dropwise to an ice-water bath cooled solution of dimethylamine hydrochloride (1.6 g, 20 mmol) and triethylamine (4.3 ml, 30 mmol) in dichloromethane, then the mixture was slowly warmed to room temperature to react for 1 hour. The pH thereof was adjusted to about 7 with 1N hydrochloric acid, then it was extracted with dichloromethane. The organic phases were combined, washed with saturated sodium bicarbonate solution and saturated brine, dried over anhydrous sodium sulfate, concentrated and recrystallized with petroleum ether and ethyl acetate to give a white solid 3.1 g, yield: 95%. $^1$HNMR (300 MHz, CDCl$_3$): δ 7.3-7.5 (5H, m), 7.2 (1H, m), 6.7-6.8 (3H, m), 5.0 (2H, s), 2.8-2.9 (1H, m), 2.7-2.8 (1H, m), 2.6 (3H, s), 2.5 (3H, s), 1.8-1.9 (1H, m), 1.4-1.6 (1H, m), 1.1 (3H, d, J=6.2), 0.8 (3H, t, J=6.8, 14.1). ESI-MS: 326.4 (M+H).

Example 6

(βR,γR)-γ-ethyl-N,N,β-trimethyl-3-(phenylmethoxy)benzenepropanamine

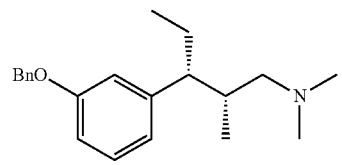

Lithium aluminum tetrahydride (730 mg, 20 mmol) was suspended in tetrahydrofuran (10 ml), then it was cooled in an ice-water bath and the solution of product of Example 5 (3 g, 9.2 mmol) in tetrahydrofuran (10 ml) was added dropwise. The reaction was carried out for 2 hours and quenched by adding 10% NaOH aqueous solution, Then the reaction solution was extracted with ethyl acetate for three times, and the organic phases were combined, washed with saturated brine, dried over anhydrous sodium sulfate and concentrated to give a pale yellow oil 2.7 g, yield: 93%. $^1$HNMR (300 MHz, CDCl$_3$): δ 7.3-7.5 (5H, m), 7.2 (1H, t, J=7.6, 15.1), 6.8 (1H, d, J=8.5), 6.7 (2H, m), 5.0 (2H, s), 2.2-2.3 (2H, m), 2.2 (3H, s), 2.1 (3H, s), 1.8-1.9 (1H, m), 1.7-1.8 (1H, m), 1.5-1.6 (1H, m), 1.4-1.5 (1H, m), 1.0 (3H, d, J=6.2), 0.8 (3H, t, J=7.4, 14.7). ESI-MS: 312.3 (M+H).

Example 7

3-((1R,2R)-3-(dimethylamino)-1-ethyl-2-methylpropyl) phenol hydrochloride

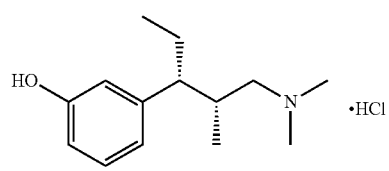 [SMILES: CC[C@@H](c1cccc(O)c1)[C@@H](C)CN(C)C ; Cl]

The product of Example 6 (2.5 g, 8 mmol) was dissolved in methanol, 5% Pd—C (250 mg) was added, and it was purged with hydrogen for three times, then the reaction was carried out with stirring at room temperature for 1 hr. The reaction solution was filtered to remove Pd—C, the residue was washed with methanol for 3 times, then the organic phases are combined and concentrated to 2 ml. After that, the concentrated hydrochloric acid (670 ml, 8 mmol) was added dropwise, then the resulted solution was concentrated and recrystallized with isopropanol and ethyl acetate to give the target 1.9 g, yield: 90%. [α]$_D$=+ 24.3° (c=1.10, CH$_3$OH). $^1$HNMR (300 MHz, CD$_3$OD): δ 7.2 (1H, t, J=7.9, 15.6), 6.6-6.8 (3H, m), 2.8-2.9 (2H, m), 2.7-2.8 (6H, br s), 2.2-2.3 (1H, m), 2.1-2.2 (1H, m), 1.8-1.9 (1H, m), 1.5-1.6 (1H, m), 1.2 (3H, d, J=6.7), 0.8 (3H, t, J=7.4, 14.4). ESI-MS: 222.4 (M+H).

Example 8

(4R,5S)-3-(((E)-3-(3-(benzyloxy)phenyl)acryloyl)-4,5-diphenyl oxazolidin-2-one

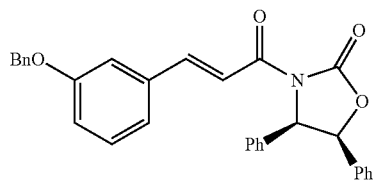 [SMILES: O=C(/C=C/c1cccc(OCc2ccccc2)c1)N1C(=O)O[C@@H](c2ccccc2)[C@H]1c1ccccc1]

The (4R,5S)-diphenyl oxazolidin-2-one (4.8 g, 20 mmol) was put in a double-necked flask, after purged with nitrogen, tetrahydrofuran was added and it was cooled to −78° C., then n-butyl lithium (2.5M, 8 ml, 20 mmol) was added dropwise, and the reaction was carried out for 30 minutes. After that, a solution of m-benzyloxy cinnamoyl chloride (6.0 g, 22 mmol) in tetrahydrofuran was added dropwise, the reaction was continued for 30 minutes, then it was slowly raised to 0° C., the reaction was continued for 2 hours, then quenched with saturated ammonium chloride solution. The reaction solution was concentrated to remove tetrahydrofuran and washed with ethyl acetate 3 times, then the organic phases were combined, washed with saturated sodium bicarbonate aqueous solution twice and saturated brine once, dried over anhydrous sodium sulfate, concentrated and recrystallized with petroleum ether and ethyl acetate to give a white solid 8.6 g, yield: 90%. $^1$HNMR (300 MHz, CDCl$_3$): δ 8.0 (1H, d, J=15.5), 7.8 (1H, d, J=15.6), 7.3-7.5 (6H, m), 7.2-7.3 (2H, m), 7.1-7.2 (6H, m), 7.0-7.1 (3H, m), 6.9-7.0 (2H, m), 6.0 (1H, d, J=7.4), 5.8 (1H, d, J=7.3), 5.1 (2H, s). ESI-MS: 476.4 (M+H).

Example 9

3-[(3R)-1-oxo-3-[3-(phenylmethoxy)phenyl]pentyl]-4R,5S-diphenyl-2-Oxazolidinone

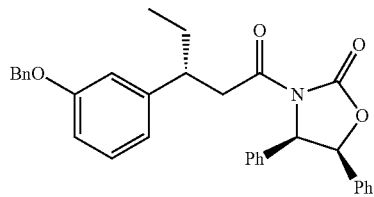 [SMILES: CC[C@H](CC(=O)N1C(=O)O[C@@H](c2ccccc2)[C@H]1c1ccccc1)c1cccc(OCc2ccccc2)c1]

Cuprous bromide dimethyl sulfide complex (5.5 g, 26.8 mmol) was placed in a three-necked flask, after purged with nitrogen, tetrahydrofuran was added and it was cooled to −40° C., then ethyl magnesium bromide (2.5M, 21.5 ml) was added dropwise, the reaction was carried out with stirring for 10 minutes. After that, the boron trifluoride diethyl ether (3.4 ml, 26.8 mmol) was added dropwise, and the reaction was continued for 10 minutes; then the solution of the product of Example 8 (8.0 g, 17.9 mmol) in tetrahydrofuran was added dropwise, after the addition was complete, it was warmed to −15° C., and then gradually warmed to room temperature. The reaction was continued for 2 hours and quenched with saturated ammonium chloride solution. The reaction solution was then concentrated to remove tetrahydrofuran, then the resultant was diluted with ethyl acetate, filtered to remove insoluble material and extracted with ethyl acetate twice, then the organic phases were combined, washed with 1N ammonia twice, then washed with water and saturated brine, dried over anhydrous sodium sulfate, concentrated and recrystallized with petroleum ether and ethyl acetate to obtain a white solid 7.6 g, yield: 84%, d.r.=99:1. $^1$HNMR (300 MHz, CDCl$_3$): δ 7.3-7.5 (5H, m), 7.2 (1H, t, J=7.9, 15.7), 7.0-7.1 (6H, m), 6.9-7.0 (3H, m), 6.8-6.9 (4H, m), 5.7 (1H, d, J=8.1), 5.5 (1H, d, J=8.2), 5.0 (2H, s), 3.6 (1H, dd, J=7.4, 14.9), 3.2 (1H, dd, J=9.6, 16.9), 3.0-3.1 (1H, m), 1.6-1.8 (2H, m), 0.8 (3H, t, J=7.3, 14.6). ESI-MS: 506.4 (M+H).

Example 10

3-[(2R,3R)-2-methyl-1-oxo-3-[3-(phenylmethoxy)phenyl]pentyl]-4R,5S-diphenyl-2-Oxazolidinone

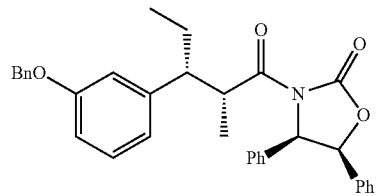 [SMILES: CC[C@@H](c1cccc(OCc2ccccc2)c1)[C@@H](C)C(=O)N1C(=O)O[C@@H](c2ccccc2)[C@H]1c1ccccc1]

The product of Example 9 (7.5 g, 14.9 mmol) was placed in a double-necked flask, after it was purged with nitrogen and cooled to −78° C., tetrahydrofuran was added, and the solution of sodium hexamethyldisilylamide (NaHMDS) in tetrahydrofuran (2M, 7.5 ml, 15 mmol) was slowly added dropwise, and the reaction was kept at −78° C. for 30 min; after methyl iodide (1.9 ml, 30 mmol) was added, the reaction was continued at −78° C. for 30 min, then it was slowly warmed to −20° C., and the reaction was continued for 2 hour, then quenched with saturated ammonium chloride solution, and then the mixture was concentrated to remove tetrahydrofuran and extracted with ethyl acetate for three times, the organic phases were combined, washed with saturated brine, dried over anhydrous sodium sulfate, concentrated, and recrystallized with petroleum ether and ethyl acetate to give a white solid 7.0 g, yield: 90%, d.r.=99.9:0.1. $^1$HNMR (300 MHz, CDCl$_3$): δ 7.4-7.5 (2H, m), 7.2-7.4 (4H, m), 7.0-7.1 (6H, m), 6.8-6.9 (3H, m), 6.8 (2H, m), 6.7 (2H, m), 5.2 (1H, d, J=8.2), 5.1 (2H, s), 5.0 (1H, d, J=7.8), 4.2-4.3 (1H, m), 2.6-2.7 (1H, dt, J=3.1, 13.0), 1.9-2.0 (1H, m), 1.5-1.7 (1H, m), 1.3 (3H, d, J=6.6), 0.8 (3H, t, J=7.5, 14.8). ESI-MS: 542.2 (M+Na).

Example 11

(R,E)-3-(3-(3-methoxy)phenyl)acryloyl)-4-phenyl oxazolidin-2-one

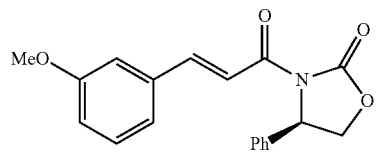 [SMILES: COc1cccc(/C=C/C(=O)N2C(=O)OC[C@H]2c2ccccc2)c1]

The 4R-phenyl-2-oxazolidinone (5.6 g, 34.4 mmol) was placed in a three-necked flask, after it was purged with nitrogen, tetrahydrofuran was added and it was cooled to −78° C., then n-butyl lithium (1.6M, 22 ml, 35.4 mmol) was added dropwise, and the reaction was carried out for 30 minutes. After a solution of m-methoxy cinnamoyl chloride (10.3 g, 37.8 mmol) in tetrahydrofuran was added dropwise, the reaction was continued for 30 minutes, then it was slowly raised to 0° C., the reaction was continued for 2 hours and quenched with saturated ammonium chloride solution. The mixture was concentrated to remove tetrahydrofuran and extracted with ethyl acetate 3 times, then the organic phases were combined, washed with saturated brine, dried over anhydrous sodium sulfate, concentrated, and recrystallized with petroleum ether and ethyl acetate to give a white solid 10.3 g, yield: 92%. $^1$HNMR (300 MHz, CDCl$_3$): δ 8.0 (1H, d, J=15.3), 7.8 (1H, d, J=15.7), 7.2-7.4 (6H, m), 7.1-7.2 (2H, m), 7.0 (1H, d, J=8.6), 5.6 (1H, dd, J=4.0, 9.0), 4.8 (1H, t, J=8.8, 17.5), 4.3 (1H, dd, J=4.0, 8.8), 3.8 (3H, s). ESI-MS: 346.3 (M+Na).

Example 12

3-[(3R)-3-(3-methoxyphenyl)-1-oxopentyl]-4R-phenyl-2-Oxazolidinone

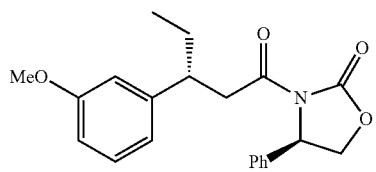 [SMILES: CC[C@H](CC(=O)N1C(=O)OC[C@H]1c1ccccc1)c1cccc(OC)c1]

Cuprous bromide dimethyl sulfide complex (7.7 g, 37.5 mmol) was placed in a three-necked flask, and it was purged with nitrogen, then tetrahydrofuran was added and it was cooled to −40° C. After ethyl magnesium bromide (2.5M, 30 ml, 75 mmol) was added dropwise, the reaction was carried out with stirring for 10 minutes, and the reaction solution turned yellow; the boron trifluoride diethyl ether (4.8 ml, 37.5 mmol) was added dropwise, and the reaction was continued for 10 minutes; the solution of the product of Example 11 (8 g, 25 mmol) in tetrahydrofuran was added dropwise, after the addition was complete, it was warmed to −15° C., and then gradually warmed to room temperature, after the reaction was continued for 2 hours, it was quenched with saturated ammonium chloride solution, and the reaction solution was concentrated to remove tetrahydrofuran, then diluted with ethyl acetate, filtered to remove insoluble material and separated, after the aqueous phase was extracted twice with ethyl acetate, the organic phases were combined, washed with 1N ammonia twice, washed with water and saturated brine, dried over anhydrous sodium sulfate, concentrated, and recrystallized with petroleum ether and ethyl acetate to obtain the target 7.4 g, yield: 84%, d.r.=99:1. $^1$HNMR (300 MHz, CDCl$_3$): δ 7.2-7.4 (6H, m), 7.1-7.2 (2H, m), 7.0 (1H, d, J=8.6), 5.3 (1H, dd, J=4.0, 9.0), 4.5 (1H, t, J=8.8, 17.5), 4.2 (1H, dd, J=4.0, 8.8), 3.8 (3H, s), 3.5 (1H, dd, J=8.9, 16.3), 3.2 (1H, d, J=5.6), 3.1 (1H, m), 1.6-1.7 (2H, m), 0.9 (3H, t, J=7.3, 14.7). ESI-MS: 354.5 (M+H).

Example 13

3-[(2R,3R)-3-(3-methoxyphenyl)-2-methyl-1-oxopentyl]-4R-phenyl-2-Oxazolidinone

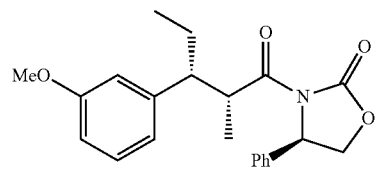

The product of Example 12 (7.1 g, 20 mmol) was placed in a double-necked flask, after it was purged with nitrogen and cooled to −78° C., tetrahydrofuran was added, and the solution of sodium hexamethyldisilylamide (NaHMDS) in tetrahydrofuran (2M, 10 ml, 20 mmol) was slowly added dropwise, and the reaction was kept at −78° C. for 30 min; methyl iodide (2.5 ml, 40 mmol) was added, and the reaction was continued at −78° C. for 30 min, then it was slowly warmed to −50° C., and the reaction was continued for 1 hour, then quenched with saturated ammonium chloride solution. After the reaction solution was concentrated to remove tetrahydrofuran and extracted with ethyl acetate for three times, the organic phases were combined, washed with saturated brine, dried over anhydrous sodium sulfate concentrated, and recrystallized with petroleum ether and ethyl acetate to give a white solid 5.9 g, yield: 81%, d.r.=99.9:0.1. $^1$HNMR (300 MHz, CDCl$_3$): δ 7.2-7.4 (6H, m), 7.1-7.2 (2H, m), 7.0 (1H, d, J=8.4), 4.9 (1H, dd, J=3.5, 7.6), 4.2-4.3 (1H, m), 3.9-4.0 (2H, m), 3.8 (3H, s), 2.7 (1H, dt, J=3.7, 10.4), 1.8-1.9 (1H, m), 1.4-1.6 (1H, m), 1.2 (3H, d, J=7.2), 0.8 (3H, t, J=7.5, 14.7). ESI-MS: 368.4 (M+H).

Example 14

(αR,βR)-β-ethyl-3-methoxy-α-methylbenzenepropanoic acid

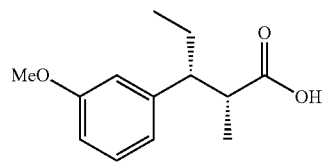

The product of Example 13 (5.5 g, 15 mmol) was dissolved in tetrahydrofuran/water (v/v=4/1), when it was cooled in an ice bath, 30% hydrogen peroxide (1.9 ml, 60 mmol) and lithium hydroxide (574 mg, 24 mmol) aqueous solution was added dropwise in sequence, then it was slowly warmed to room temperature and the reaction was continued for 4 hours. Sodium sulfite aqueous solution (2.5M, 24 ml) was added dropwise to the reaction liquid, which was stirred for 10 minutes and concentrated to remove tetrahydrofuran, then extracted with dichloromethane for three times, washed with water and saturated brine, dried over anhydrous sodium sulfate, concentrated, and recovered to give 4R-phenyl oxazolidin-2-one 2.3 g. The pH of the aqueous phase was adjusted to appropriate 2 with 1N hydrochloric acid, then extracted with dichloromethane for three times, and then the organic phases were combined, washed with saturated sodium bicarbonate solution and saturated brine, dried over anhydrous sodium sulfate concentrated, and recrystallized with petroleum ether and ethyl acetate to give a white solid 3.0 g, yield: 90%. ¹HNMR (300 MHz, CDCl₃): δ 7.2 (1H, t, J=7.9, 15.6), 6.6-6.8 (3H, m), 3.7 (3H, s), 2.7 (1H, m), 2.6 (1H, m), 1.7-1.8 (1H, m), 1.5-1.6 (1H, m), 1.1 (3H, d, 6.7), 0.8 (3H, t, J=7.4, 14.7). ESI-MS: 221.0 (M−H).

Example 15

(αR,βR)-β-ethyl-3-methoxy-N,N,α-trimethylbenzenepropanamide

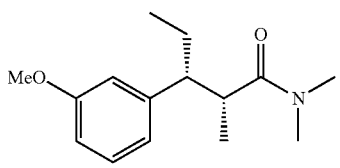 [SMILES: CC[C@@H](c1cccc(OC)c1)[C@@H](C)C(=O)N(C)C]

The product of Example 14 (2.2 g, 10 mmol) was dissolved in dichloromethane (10 ml), oxalyl chloride (2.6 ml, 30 mmol) was added dropwise, and the reaction was carried out at room temperature for 1 hr, then the reaction solution was concentrated to give a pale yellow oil which was thereafter dissolved in dichloromethane, and then the resulted solution was added dropwise to an ice bath cooled solution of dimethylamine hydrochloride (1.6 g, 20 mmol) and triethylamine (4.3 ml, 30 mmol) in dichloromethane. Then it was slowly warmed to room temperature to make the reaction carry out for 1 hour. The pH was adjusted to about 7 with 1N hydrochloric acid, then the reaction solution was extracted with dichloromethane, and the organic phases were combined, washed with saturated sodium bicarbonate solution and saturated brine, dried over anhydrous sodium sulfate concentrated, and recrystallized with petroleum ether and ethyl acetate to give a white solid 2.3 g, yield: 92%. ¹HNMR (300 MHz, CDCl₃): δ 7.2 (1H, t, J=7.9, 15.6), 6.6-6.8 (3H, m), 3.7 (3H, s), 2.8-2.9 (1H, m), 2.7-2.8 (1H, m), 2.6 (3H, s), 2.5 (3H, s), 1.7-1.8 (1H, m), 1.4-1.6 (1H, m), 1.1 (3H, d, J=6.2), 0.8 (3H, t, J=6.8, 14.3). ESI-MS: 250.4 (M+H).

Example 16

(βR,γR)-γ-ethyl-N,N,β-trimethyl-3-methoxybenzenepropanamine

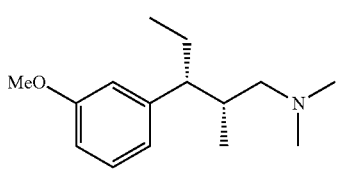 [SMILES: CC[C@@H](c1cccc(OC)c1)[C@@H](C)CN(C)C]

Lithium aluminum tetrahydride (730 mg, 20 mmol) was suspended in tetrahydrofuran (10 ml), after the mixture was cooled in an ice-water bath, the solution of product of Example 15 (2.2 g, 9.0 mmol) in tetrahydrofuran (10 ml) was added dropwise, then the reaction was carried out for 2 hours, and quenched by adding 10% NaOH aqueous solution, after the reaction solution was extracted with ethyl acetate for three times, the organic phases were combined, washed with saturated brine, dried over anhydrous sodium sulfate and concentrated to give a pale yellow oil 1.9 g, yield: 90%. ¹HNMR (300 MHz, CDCl₃): δ 7.2 (1H, t, J=7.9, 15.6), 6.6-6.8 (3H, m), 3.7 (3H, s), 2.2-2.3 (2H, m), 2.2 (3H, s), 2.1 (3H, s), 1.8-1.9 (1H, m), 1.7-1.8 (1H, m), 1.5-1.6 (1H, m), 1.4-1.5 (1H, m), 1.0 (3H, d, J=6.3), 0.8 (3H, t, J=7.4, 14.5). ESI-MS: 236.3 (M+H).

Example 17

3-((1R,2R)-3-(dimethylamino)-1-ethyl-2-methylpropyl)-phenol hydrochloride

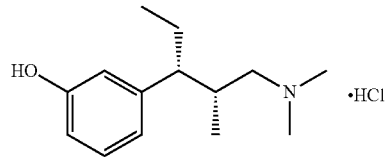 [SMILES: CC[C@@H](c1cccc(O)c1)[C@@H](C)CN(C)C ; Cl]

The product of Example 16 (1.9 g, 8 mmol) was dissolved in dichloromethane, the mixture was cooled in an ice-water bath, and a solution of boron tribromide (1.9 ml, 20 mmol) in dichloromethane was slowly added dropwise, then it was gradually raised to room temperature to make it react for 15 hrs. After it was cooled in an ice-water bath, methanol was slowly added dropwise to quench the reaction, and the organic phase was washed with water and saturated brine, dried over anhydrous sodium sulfate, and concentrated to 2 mL, then the concentrated hydrochloric acid (670 Ml, 8 mmol) was added dropwise, and the mixture was concentrated and recrystallized with isopropanol and ethyl acetate to obtain the target 1.8 g, yield: 90%. [α]_D=+24.3° (c=1.10, CH₃OH). ¹HNMR (300 MHz, CD₃OD): δ 7.2 (1H, t, J=7.9, 15.6), 6.6-6.8 (3H, m), 2.8-2.9 (2H, m), 2.7-2.8 (6H, br s), 2.2-2.3 (1H, m), 2.1-2.2 (1H, m), 1.8-1.9 (1H, m), 1.5-1.6 (1H, m), 1.2 (3H, d, J=6.7), 0.8 (3H, t, J=7.4, 14.4). ESI-MS: 222.4 (M+H).

Example 18

(4R,5S)-3-(((E)-3-(3-(methoxy)phenyl)acryloyl)-4,5-diphenyl oxazolidin-2-one

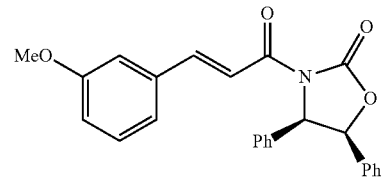 [SMILES: COc1cccc(/C=C/C(=O)N2C(=O)O[C@@H](c3ccccc3)[C@H]2c2ccccc2)c1]

The (4R,5S)-diphenyl oxazolidin-2-one (4.8 g, 20 mmol) was placed in a double-necked flask, after it was purged with nitrogen, tetrahydrofuran was added and the mixture was cooled to −78° C., then n-butyl lithium (2.5M, 8 ml, 20 mmol) was added dropwise, and the reaction was carried out for 30 minutes. Then a solution of m-methoxy cinnamoyl chloride (4.3 g, 22 mmol) in tetrahydrofuran was added dropwise, the reaction was continued for 30 minutes, then it was slowly raised to 0° C., and the reaction was continued for 2 hours, then quenched with saturated ammonium chloride solution. After that, the reaction solution was concentrated to remove tetrahydrofuran and washed with ethyl acetate 3 times, then the organic phases were combined, washed with saturated sodium bicarbonate aqueous solution twice and saturated brine once, dried over anhydrous sodium sulfate concentrated, and recrystallized with petroleum ether and ethyl acetate to give a white solid 7.3 g, yield: 92%. ¹HNMR (300 MHz, CDCl₃): δ 8.0 (1H, d, J=15.8), 7.8 (1H, d, J=15.8), 7.3-7.4 (1H, m), 7.2-7.3 (1H, m), 7.1-7.2 (7H, m), 6.8-7.0 (5H, m), 6.0 (1H, d, J=7.6), 5.8 (1H, d, J=7.7), 3.8 (3H, s). ESI-MS: 400.4 (M+H).

Example 19

3-[(3R)-3-(3-methoxyphenyl)-1-oxopentyl]-4R,5S-diphenyl-2-Oxazolidin one

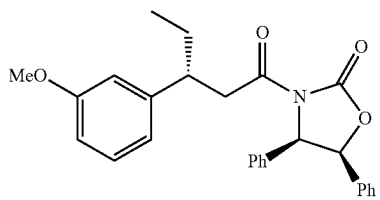 [SMILES: CC[C@H](CC(=O)N1C(=O)O[C@@H](c2ccccc2)[C@H]1c1ccccc1)c1cccc(OC)c1]

Cuprous bromide dimethyl sulfide complex (5.5 g, 26.8 mmol) was placed in a three-necked flask, after it was purged with nitrogen, tetrahydrofuran was added and the mixture was cooled to −40° C., then ethyl magnesium bromide (2.5M, 21.5 ml) was added dropwise, and the reaction was carried out with stirring for 10 minutes. After the boron trifluoride diethyl ether (3.4 ml, 26.8 mmol) was added dropwise, the reaction was continued for 10 minutes. The solution of the product of Example 18 (7.1 g, 17.9 mmol) in tetrahydrofuran was added dropwise, after the addition was complete, it was warmed to −15° C., and then gradually warmed to room temperature, then the reaction was continued for 2 hours and quenched with saturated ammonium chloride solution. The reaction solution was concentrated to remove tetrahydrofuran, then diluted with ethyl acetate and filtered to remove insoluble material. The filtration was then extracted with ethyl acetate twice, and the organic phases were combined, washed with 1N ammonia twice, then washed with water and saturated brine, dried over anhydrous sodium sulfate, concentrated and recrystallized with petroleum ether and ethyl acetate to obtain a white solid 6.2 g, yield: 81%, d.r.=99:1. ¹HNMR (300 MHz, CDCl₃): δ 7.2 (1H, m), 7.0-7.2 (6H, m), 6.9-7.0 (2H, m), 6.8-6.9 (5H, m), 5.7 (1H, d, J=8.1), 5.5 (1H, d, J=7.8), 3.8 (3H, s), 3.6 (1H, dd, J=9.2, 16.4), 3.2 (1H, dd, J=5.5, 16.8), 3.0-3.1 (1H, m), 1.6-1.8 (2H, m), 0.8 (3H, t, J=7.4, 14.9). ESI-MS: 430.4 (M+H).

Example 20

3-[(2R,3R)-3-(3-methoxyphenyl)-2-methyl-1-oxopentyl]-4R,5S-diphenyl-2-Oxazolidinone

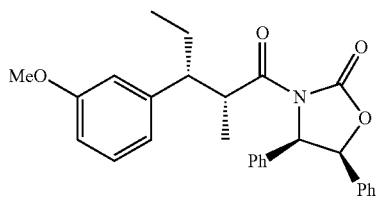 [SMILES: CC[C@@H](c1cccc(OC)c1)[C@@H](C)C(=O)N1C(=O)O[C@@H](c2ccccc2)[C@H]1c1ccccc1]

The product of Example 19 (6.2 g, 14.5 mmol) was placed in a double-necked flask, and it was purged with nitrogen and cooled to −78° C., then tetrahydrofuran was added, and the solution of sodium hexamethyldisilylamide in tetrahydrofuran (2M, 7.5 ml, 15 mmol) was slowly added dropwise, and then the reaction was kept at −78° C. for 30 min; after that, methyl iodide (1.9 ml, 30 mmol) was added, and the reaction was continued at −78° C. for 30 min, then it was slowly warmed to −20° C., and the reaction was continued for 2 hour, and then quenched with saturated ammonium chloride solution. The reaction solution was then concentrated to remove tetrahydrofuran and extracted with ethyl acetate for three times, then the organic phases were combined, washed with saturated brine, dried over anhydrous sodium sulfate, concentrated, and recrystallized with petroleum ether and ethyl acetate to give a white solid 5.7 g, yield: 89%, d.r.=99.9:0.1. ¹HNMR (300 MHz, CDCl₃): δ 7.2 (1H, m), 7.0-7.2 (6H, m), 6.9-7.0 (2H, m), 6.8-6.9 (5H, m), 5.5 (1H, d, J=8.1), 5.3 (1H, d, J=7.8), 4.0-4.1 (1H, m), 3.8 (3H, s), 2.6-2.7 (1H, dt, J=3.1, 13.0), 1.9-2.0 (1H, m), 1.5-1.7 (1H, m), 1.3 (3H, d, J=6.6), 0.8 (3H, t, J=7.5, 14.8). ESI-MS: 444.5 (M+H).

Example 21

(S,E)-3-(pent-2-enoyl)-4-phenyl oxazolidin-2-one

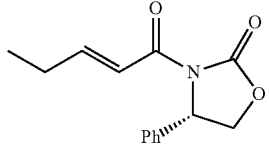 [SMILES: CC/C=C/C(=O)N1C(=O)OC[C@@H]1c1ccccc1]

The 4S-phenyl-2-oxazolidinone (5.6 g, 34.4 mmol) was placed in a three-necked flask, after it was purged with nitrogen, tetrahydrofuran was added and it was cooled to −78° C., then n-butyl lithium (1.6M, 22 ml, 35.4 mmol) was added dropwise, and the reaction was carried out for 30 minutes. After that, a solution of 2-pentenoyl chloride (4.2 g, 35.5 mmol) in tetrahydrofuran was added dropwise, and the reaction was continued for 30 minutes, then it was slowly raised to 0° C., the reaction was continued for 2 hours and quenched with saturated ammonium chloride solution. The reaction solution was then concentrated to remove tetrahydrofuran and extracted with ethyl acetate 3 times, then the organic phases were combined, washed with saturated brine, dried over anhydrous sodium sulfate, concentrated, and recrystallized with petroleum ether and ethyl acetate to give a white solid 8 g, yield: 95%. ¹HNMR (300 MHz, CDCl₃): δ 7.3-7.4 (5H, m), 7.1-7.2 (1H, m), 6.9-7.1 (1H, m), 5.5 (1H, dd, J=4.2, 19.0), 4.8 (1H, t, J=9.6, 18.7), 4.2 (1H, dd, J=3.7, 18.9), 2.2 (2H, m), 1.0 (3H, t, J=7.4, 14.9). ESI-MS: 246.4 (M+H).

Example 22

3-[(3R)-1-oxo-3-[3-(phenylmethoxy)phenyl]pentyl]-4S-phenyl-2-Oxazolidinone

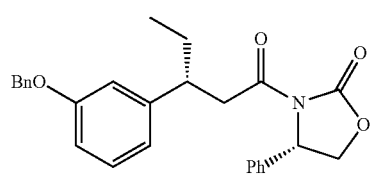 [SMILES: CC[C@H](CC(=O)N1C(=O)OC[C@@H]1c1ccccc1)c1cccc(OCc2ccccc2)c1]

Cuprous bromide dimethyl sulfide complex (10.0 g, 48.9 mmol) was placed in a three-necked flask, after it was purged with nitrogen, tetrahydrofuran was added and it was cooled to -40° C., then 3-benzyloxy phenyl magnesium bromide (2.5M, 39 ml, 97.8 mmol) was added dropwise, the reaction was carried out with stirring for 10 minutes, and the reaction solution turned yellow; after that, the boron trifluoride diethyl ether (6.2 ml, 48.9 mmol) was added dropwise and the reaction was continued for 10 minutes; then the solution of the product of Example 21 (8 g, 32.6 mmol) in tetrahydrofuran was added dropwise, after the addition was complete, it was warmed to −15° C., and then gradually warmed to room temperature. After that, the reaction was continued for 2 hours, then quenched with saturated ammonium chloride solution. The reaction solution was concentrated to remove tetrahydrofuran, diluted with ethyl acetate, filtered to remove insoluble material, and separated, then the aqueous phase was extracted twice with ethyl acetate, and the organic phases were combined, washed with 1N ammonia twice, then washed with water and saturated brine, dried over anhydrous sodium sulfate, concentrated, and recrystallized with petroleum ether and ethyl acetate to obtain the target 12 g, yield: 86%, d.r.=99:1. $^1$HNMR (300 MHz, CDCl$_3$): δ 7.3-7.5 (8H, m), 7.1-7.2 (3H, m), 6.7-6.9 (3H, m), 5.1 (1H, dd, J=3.7, 8.6), 5.0 (2H, s), 4.6 (1H, t, J=8.9, 17.1), 4.1 (1H, dd, J=3.5, 8.6), 3.6 (1H, dd, J=8.9, 16.3), 3.2 (1H, d, J=5.6), 3.1 (1H, m), 1.5-1.7 (2H, m), 0.8 (3H, t, J=7.3, 14.9). ESI-MS: 430.5 (M+H).

Example 23

(βR)-ethyl-3-(phenylmethoxy)benzenepropanoic acid

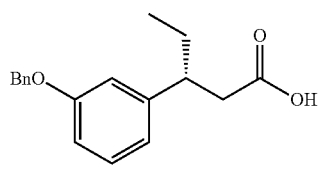

The product of Example 22 (11 g, 25.6 mmol) was dissolved in tetrahydrofuran/water (v/v=4/1) in an ice-water bath, 30% hydrogen peroxide (3.2 ml, 100 mmol) and lithium hydroxide (1.0 g, 43.5 mmol) aqueous solution were added dropwise in sequence, then it was slowly warmed to room temperature and the reaction was continued for 4 hours. After that, sodium sulfite aqueous solution (2.5M, 40 ml) was added dropwise to the reaction liquid, the reaction was carried out with stirring for 10 minutes, the reaction solution was concentrated to remove tetrahydrofuran, then extracted with dichloromethane for 3 times, washed with water and saturated brine, dried over anhydrous sodium sulfate, concentrated, and recovered to give 4S-phenyl oxazolidin-2-one 3.9 g. The pH of the aqueous phase was adjusted to appropriate 2 with 1N hydrochloric acid, then extracted with dichloromethane for three times, after that, the organic phases were combined, washed with saturated sodium bicarbonate solution and saturated brine, dried over anhydrous sodium sulfate, concentrated, and recrystallized with petroleum ether and ethyl acetate to give a white solid 6.7 g, yield: 92%. $^1$HNMR (300 MHz, CDCl$_3$): δ 7.3-7.5 (5H, m), 7.2 (1H, t, J=7.6, 15.2), 6.8-6.9 (3H, m), 5.0 (2H, s), 3.0 (1H, m), 2.6-2.7 (2H, m), 1.7-1.8 (1H, m), 1.6-1.7 (1H, m), 0.8 (3H, t, J=7.3, 14.7). ESI-MS: 283.1 (M−H).

Example 24

3-[(3R)-1-oxo-3-[3-(phenylmethoxy)phenyl]pentyl]-4R-phenyl-2-Oxazolidinone

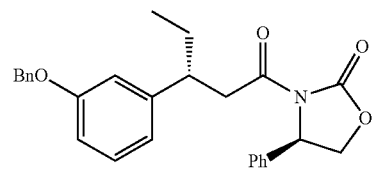 [SMILES: CC[C@H](CC(=O)N1C(=O)OC[C@H]1c1ccccc1)c1cccc(OCc2ccccc2)c1]

The 4R-phenyl-2-oxazolidinone (3.5 g, 21.4 mmol) was placed in a three-necked flask, after it was purged with nitrogen, tetrahydrofuran was added and it was cooled to −78° C., then n-butyl lithium (1.6M, 13.8 ml, 22 mmol) was added dropwise, and the reaction was carried out for 30 minutes. After that, a solution of (R)-3-(3-(benzyloxy)phenyl)pentanoyl chloride (7.1 g, 23.6 mmol) in tetrahydrofuran was added dropwise, the reaction was continued for 30 minutes, then it was slowly raised to 0° C., the reaction was continued for 2 hours, and then quenched with saturated ammonium chloride solution. The reaction solution was then concentrated to remove tetrahydrofuran and extracted with ethyl acetate 3 times, then the organic phases were combined, washed with saturated brine, dried over anhydrous sodium sulfate, concentrated, and recrystallized with petroleum ether and ethyl acetate to give a white solid 8.6 g, yield: 85%. $^1$HNMR (CDCl$_3$): δ 7.3-7.5 (8H, m), 7.1-7.2 (3H, m), 6.7-6.9 (3H, m), 5.2 (1H, dd, J=3.7, 8.6), 5.1 (2H, s), 4.5 (1H, t, J=8.9, 17.1), 4.2 (1H, dd, J=3.5, 8.6), 3.5 (1H, dd, J=8.9, 16.4), 3.2 (1H, d, J=5.6), 3.1 (1H, m), 1.5-1.7 (2H, m), 0.9 (3H, t, J=7.3, 14.7). ESI-MS: 430.5 (M+H).

Example 25

3-[(2R,3R)-2-methyl-1-oxo-3-[3-(phenylmethoxy)phenyl]pentyl]-4R-phenyl-2-Oxazolidinone

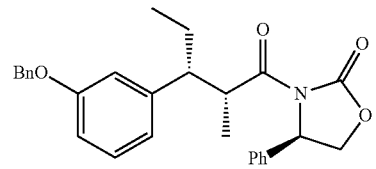 [SMILES: CC[C@@H](c1cccc(OCc2ccccc2)c1)[C@@H](C)C(=O)N1C(=O)OC[C@H]1c1ccccc1]

The product of Example 24 (8.6 g, 20 mmol) was placed in a double-necked flask, and it was purged with nitrogen and cooled to −78° C., then tetrahydrofuran was added, and the solution of sodium hexamethyldisilylamide (NaHMDS) in tetrahydrofuran (2M, 10 ml, 20 mmol) was slowly added dropwise, and the reaction was kept at −78° C. for 30 min; after that, methyl iodide (2.5 ml, 40 mmol) was added, and the reaction was continued at −78° C. for 30 min, then it was slowly warmed to −50° C., and the reaction was continued for 1 hour, and then quenched with saturated ammonium chloride solution. The reaction solution was then concentrated to remove tetrahydrofuran and extracted with ethyl acetate for three times, then the organic phases were combined, washed with saturated brine, dried over anhydrous sodium sulfate, concentrated, and recrystallized with petroleum ether and ethyl acetate to give a white solid 7.5 g, yield: 85%, d.r.=99.9: 0.1. ¹HNMR (300 MHz, CDCl₃): δ 7.2-7.5 (11H, m), 6.7-6.9 (3H, m), 5.1 (2H, s), 4.8 (1H, dd, J=3.5, 7.5), 4.2-4.3 (1H, m), 3.9-4.0 (2H, m), 2.6 (1H, dt, J=3.7, 10.3), 1.8-2.0 (1H, m), 1.4-1.6 (1H, m), 1.2 (3H, d, J=7.2), 0.9 (3H, t, J=7.4, 14.7). ESI-MS: 444.4 (M+H).

Example 26

(αR,βR)-β-ethyl-3-hydroxy-N,N,α-trimethylbenzenepropanamide

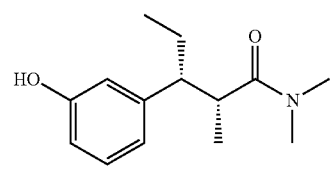 [SMILES: CC[C@@H](c1cccc(O)c1)[C@@H](C)C(=O)N(C)C]

The product of Example 5 (3.0 g, 9 mmol) was dissolved in methanol, 5% Pd—C (300 mg) was added therein, after it was purged with hydrogen for three times, the reaction was carried out with stirring at room temperature for 1 hr. Then the reaction solution was filtered to remove Pd—C, the residue was washed with methanol for 3 times, and the organic phases are combined and concentrated to give the target 2.0 g, yield: 95%. ¹HNMR (300 MHz, CDCl₃): δ 7.2 (1H, m), 6.7-6.8 (3H, m), 2.8-2.9 (1H, m), 2.7-2.8 (1H, m), 2.6 (3H, s), 2.5 (3H, s), 1.8-1.9 (1H, m), 1.4-1.6 (1H, m), 1.1 (3H, d, J=6.2), 0.8 (3H, t, J=6.8, 14.1). ESI-MS: 236.4 (M+H).

Example 27

3-((1R,2R)-3-(dimethylamino)-1-ethyl-2-methylpropyl)-phenol hydrochloride

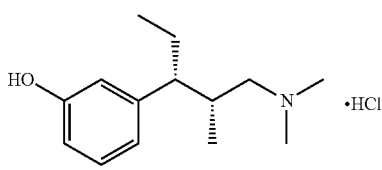 [SMILES: CC[C@@H](c1cccc(O)c1)[C@@H](C)CN(C)C ; Cl]

Lithium aluminum tetrahydride (730 mg, 20 mmol) was suspended in tetrahydrofuran (10 ml), and it was cooled in an ice-water bath, then the solution of product of Example 26 (2 g, 8.5 mmol) in tetrahydrofuran (10 ml) was added dropwise, the reaction was carried out for 2 hours and then quenched by adding 10% NaOH aqueous solution. The reaction solution was then extracted with ethyl acetate for three times, and the organic phases were combined, washed with saturated brine, dried over anhydrous sodium sulfate and concentrated to 2 mL, then the concentrated hydrochloric acid (710 μl, 8.5 mmol) was added dropwise therein, and the resulted solution was concentrated and recrystallized with isopropanol-ethyl acetate to obtain the target 1.97 g, yield: 90%. [α]_D=+24.3° (c=1.10, CH₃OH). ¹HNMR (300 MHz, CD₃OD): δ 7.2 (1H, t, J=7.9, 15.6), 6.6-6.8 (3H, m), 2.8-2.9 (2H, m), 2.7-2.8 (6H, br s), 2.2-2.3 (1H, m), 2.1-2.2 (1H, m), 1.8-1.9 (1H, m), 1.5-1.6 (1H, m), 1.2 (3H, d, J=6.7), 0.8 (3H, t, J=7.4, 14.4). ESI-MS: 222.4 (M+H).

Example 28

(2R,3R)-3-(3-(benzyloxy)phenyl-N—((R)-2-hydroxy-1-phenylethyl)-2-methyl pentanamide

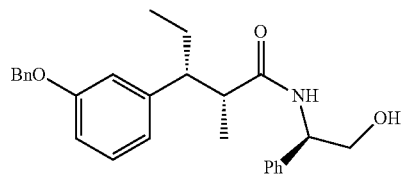 [SMILES: CC[C@@H](c1cccc(OCc2ccccc2)c1)[C@@H](C)C(=O)N[C@@H](CO)c1ccccc1]

The product of Example 3 (6.6 g, 15 mmol) was dissolved in tetrahydrofuran/water (v/v=4/1), and it was cooled in an ice-water bath, then the lithium hydroxide (574 mg, 24 mmol) aqueous solution was added dropwise, the mixture was slowly warmed to room temperature, and the reaction was continued for 6 hours. After that, the reaction solution was concentrated to remove tetrahydrofuran, extracted with dichloromethane 3 times, washed with water and saturated brine, dried over anhydrous sodium sulfate, concentrated, and then separated through silica gel column chromatography to obtain target 5.0 g, yield: 80%. ¹HNMR (300 MHz, CDCl₃): δ 7.2-7.5 (11H, m), 6.8-6.9 (3H, m), 5.6 (1H, d, J=6.9), 5.1 (2H, s), 4.8 (1H, m), 3.4 (1H, dd, J=5.4, 11.4), 3.3 (1H, dd, J=3.7, 11.5), 2.7 (1H, dt, J=3.5, 11.0), 1.8-2.0 (1H, m), 1.4-1.5 (1H, m), 1.2 (3H, d, J=6.5), 0.7 (3H, t, J=7.3, 14.6). ESI-MS: 418.3 (M+H).

Example 29

(R)-2-((2R,3R)-3-(3-(benzyloxy)phenyl)-2-methyl pentylamine)-2-phenylethanol

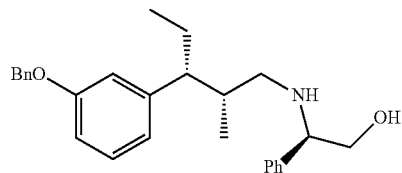 [SMILES: CC[C@@H](c1cccc(OCc2ccccc2)c1)[C@@H](C)CN[C@@H](CO)c1ccccc1]

The product of Example 28 (5.0 g, 12 mmol) was dissolved in tetrahydrofuran, lithium aluminum tetrahydride (2.3 g, 60 mmol) was added, and the reaction was conducted under reflux for 8 hours, then it was cooled in ice-water bath, and water was added dropwise to quench the reaction. After that, 10% sodium hydroxide aqueous solution was added therein, the reaction solution was filtered, and the filtrate was extracted with ethyl acetate three times, then the organic phases were combined, washed with saturated brine, dried over anhydrous sodium sulfate, concentrated, and then separated through silica gel column chromatography to give the target 4.3 g, yield: 90%. ¹HNMR (300 MHz, CD₃Cl): δ 7.3-7.5 (8H, m), 7.1-7.2 (3H, m), 6.8 (1H, m), 6.6 (2H, m), 5.0 (2H, s), 3.6-3.8 (3H, m), 2.4 (1H, dd, J=3.8, 12.0), 2.3 (1H, d, J=8.1), 2.2 (1H, m), 1.9-2.0 (1H, m), 1.7-1.8 (1H, m), 1.4-1.5 (1H, m), 1.1 (3H, d, J=6.9), 0.8 (3H, t, J=7.4, 14.5). ESI-MS: 404.4 (M+H).

Example 30

3-[(1R,2R)-3-amino-1-ethyl-2-methylpropyl]phenol

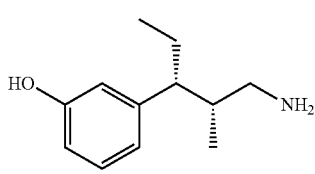

The product of Example 29 (4.0 g, 10 mmol) was dissolved in methanol, 10% Pd—C (400 mg) was added therein, after it was purged with hydrogen three times, the reaction was carried out with stirring at room temperature for 12 hours. Then the reaction solution was filtered, the residue was washed with methanol three times, and the filtrate was concentrated to give the target 1.74 g, yield: 90%. $^1$HNMR (300 MHz, CD$_3$OD): δ 7.2 (1H, t, J=7.9, 15.6), 6.6-6.8 (3H, m), 2.8-2.9 (2H, m), 2.2-2.3 (1H, m), 2.1-2.2 (1H, m), 1.8-1.9 (1H, m), 1.5-1.6 (1H, m), 1.2 (3H, d, J=6.7), 0.8 (3H, t, J=7.4, 14.4). ESI-MS: 194.4 (M+H).

Example 31

3-((1R,2R)-3-(dimethylamino)-1-ethyl-2-methylpropyl)-phenol hydrochloride

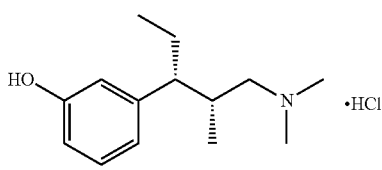 [SMILES: CC[C@@H](c1cccc(O)c1)[C@@H](C)CN(C)C ; Cl]

The product of Example 30 (1.7 g, 9 mmol) was dissolved in a formaldehyde aqueous solution, 98% formic acid (1.6 ml, 45 mmol) was added thereto, and the reaction was conducted at 80° C. for 2 hours, then the reaction solution was poured into ice-water, after that, the pH was adjusted to 8 with 10% sodium hydroxide solution, and the solution was extracted with dichloromethane three times, then the organic phases were combined, washed with water and saturated brine, dried over anhydrous sodium sulfate and concentrated to obtain an oil. The oil was dissolved in methanol, the mixture was cooled in an ice-water bath, 12N hydrochloric acid (0.7 ml, 8.4 mmol) was added and it was stirred for 10 minutes, then the ethyl acetate was added to recrystallize to obtain the target 1.4 g, yield: 60%. [α]$_D$=+24.3° (c=1.10, CH$_3$OH). $^1$HNMR (300 MHz, CD$_3$OD): δ 7.2 (1H, t, J=7.9, 15.6), 6.6-6.8 (3H, m), 2.8-2.9 (2H, m), 2.7-2.8 (6H, brs), 2.2-2.3 (1H, m), 2.1-2.2 (1H, m), 1.8-1.9 (1H, m), 1.5-1.6 (1H, m), 1.2 (3H, d, J=6.7), 0.8 (3H, t, J=7.4, 14.4). ESI-MS: 222.4 (M+H).

Example 32

(βR,γR)-γ-ethyl-β-methyl-3-(phenylmethoxy)benzenepropanol

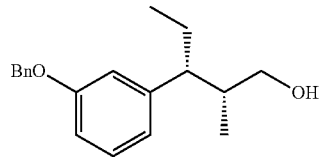 [SMILES: CC[C@@H](c1cccc(OCc2ccccc2)c1)[C@@H](C)CO]

The product of Example 3 (4.5 g, 10 mmol) was dissolved in tetrahydrofuran, lithium aluminum tetrahydride (760 mg, 20 mmol) was added, and the mixture was stirred at room temperature for 3 hours, then water was added to quench the reaction. After that, 10% sodium hydroxide solution was added, the resulted solution was filtered, and the filtrate was extracted with ethyl acetate three times, then the organic phases were combined, washed with saturated brine, dried over anhydrous sodium sulfate, concentrated, and then separated through silica gel column chromatography to give the target 2.6 g, yield: 90%. $^1$HNMR (300 MHz, CDCl$_3$): δ 7.3-7.5 (5H, m), 7.2 (1H, t, J=7.6, 15.3), 6.7-6.9 (3H, m), 5.0 (2H, s), 3.3-3.5 (2H, m), 2.8 (1H, m), 2.7 (1H, m), 1.7-1.8 (1H, m), 1.5-1.6 (1H, m), 1.1 (3H, d, 6.8), 0.9 (3H, t, J=7.3, 14.5). ESI-MS: 285.2 (M−H).

Example 33

(βR,γR)-γ-ethyl-β-methyl-3-(phenylmethoxy)benzenepropanol, 1-methanesulfonate

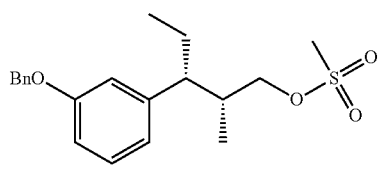 [SMILES: CC[C@@H](c1cccc(OCc2ccccc2)c1)[C@@H](C)COS(C)(=O)=O]

The product of Example 32 (2.6 g, 9 mmol) was dissolved in dichloromethane, triethylamine (1.9 ml, 13.5 mmol) was added therein, then it was cooled in ice-water bath, and methanesulfonyl chloride (0.77 ml, 10 mmol) was slowly added dropwise, after the addition was complete, the reaction was continued for 1 hour, and then quenched by adding water. The reaction solution was separated, the aqueous phase was extracted with dichloromethane three times, and the organic phases were combined, washed with saturated brine, dried over anhydrous sodium sulfate, and concentrated to give the target compound 3.0 g, yield: 91%. $^1$HNMR (300 MHz, CDCl$_3$): δ 7.3-7.5 (5H, m), 7.2 (1H, t, J=7.6, 15.3), 6.7-6.9 (3H, m), 5.0 (2H, s), 3.4 (1H, m), 3.5 (1H, m), 3.1 (3H, s), 2.8 (1H, m), 2.7 (1H, m), 1.7-1.8 (1H, m), 1.5-1.6 (1H, m), 1.1 (3H, d, 6.8), 0.9 (3H, t, J=7.3, 14.5). ESI-MS: 363.5 (M−H).

Example 34

(βR,γR)-γ-ethyl-N,N,β-trimethyl-3-(phenylmethoxy)benzenepropanamine

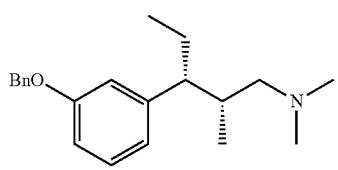 [SMILES: CC[C@@H](c1cccc(OCc2ccccc2)c1)[C@@H](C)CN(C)C]

The product of Example 33 (2.9 g, 8 mmol) was dissolved in dichloromethane, triethylamine (4.6 ml, 2 mmol) and dimethylamine hydrochloride (1.3 g, 16 mmol) were added therein, the reaction was conducted at room temperature for 8 hours, and the water was add to separate the liquid, then the aqueous phase was extracted with dichloromethane twice, and the organic phases were combined, washed with saturated brine, dried over anhydrous sodium sulfate, concentrated, and then separated through silica gel column chromatography to give target 2.2 g, yield: 90%. $^1$HNMR (300 MHz, CDCl$_3$): δ 7.3-7.5 (5H, m), 7.2 (1H, t, J=7.6, 15.1), 6.8 (1H, d, J=8.5), 6.7 (2H, m), 5.0 (2H, s), 2.2-2.3 (2H, m), 2.2 (3H, s), 2.1 (3H, s), 1.8-1.9 (1H, m), 1.7-1.8 (1H, m), 1.5-1.6 (1H, m), 1.4-1.5 (1H, m), 1.0 (3H, d, J=6.2), 0.8 (3H, t, J=7.4, 14.7). ESI-MS: 312.3 (M+H).

Example 35

(R,E)-3-(3-(3-benzyloxy)phenyl)acryloyl)-4-phenyl oxazolidin-2-one

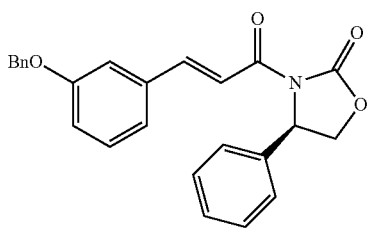 [SMILES: O=C(/C=C/c1cccc(OCc2ccccc2)c1)N1C(=O)OC[C@H]1c1ccccc1]

The m-benzyloxy cinnamic acid (90 g, 354 mmol) was dissolved in dichloromethane (25 ml), oxalyl chloride (45 ml) was added therein and it was reacted at room temperature for 5 hours, then the reaction solution was concentrated to remove the solvent and oxalyl chloride for further use; 4(R)-phenyl-2-oxazolidinone (57 g, 350 mmol) was dissolved in dichloromethane, the mixture was cooled to 0° C., and 4-dimethylamino pyridine (4.3 g, 35 mmol) and triethylamine (76 mL, 525 mmol) was added, then the solution of m-benzyloxy cinnamic acid in dichloromethane was added. After that, the reaction was continued for 8 hours and quenched with saturated ammonium chloride solution, then the reaction solution was separated, the dichloromethane layer was washed with water and saturated brine, dried over anhydrous sodium sulfate, concentrated and recrystallized with petroleum ether and ethyl acetate to give a white solid 144 g, yield: 95%. The HNMR spectrum data is the same as that in Example 1.

Example 36

3-[(3R)-1-oxo-3-[3-(phenylmethoxy)phenyl]pentyl]-4R-phenyl-2-Oxazolidinone

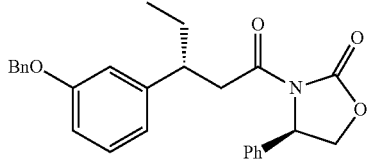 [SMILES: CC[C@H](CC(=O)N1C(=O)OC[C@H]1c1ccccc1)c1cccc(OCc2ccccc2)c1]

Cuprous bromide (7 g, 48.9 mmol) was placed in a three-necked flask, after it was purged with nitrogen, tetrahydrofuran was added and it was cooled to −20° C., the solution of ethyl magnesium bromide in tetrahydrofuran (2.5M, 39 ml, 97.8 mmol) was added dropwise, the reaction was carried out with stirring for 10 minutes, and the reaction solution turned yellow; after that, boron trifluoride diethyl etherate (6.2 ml, 48.9 mmol) was added dropwise, and the reaction was continued for 10 minutes; then the solution of the product of Example 35 (13 g, 32.6 mmol) in tetrahydrofuran was added dropwise, after the addition was complete, the temperature was raised to −5° C., then the reaction was continued for 2 hours and quenched with saturated ammonium chloride solution. Then the reaction solution was concentrated to remove tetrahydrofuran, diluted with ethyl acetate, filtered to remove insoluble material and separated, the aqueous phase was re-extracted with ethyl acetate twice, the organic phases were combined, washed with 1N ammonia twice, washed with water and saturated brine, dried over anhydrous sodium sulfate, concentrated and recrystallized with petroleum ether and ethyl acetate to give the target 12 g, yield: 85%, d.r.=98:1. The HNMR spectrum data is the same as that in Example 2.

Example 37

3-[(2R,3R)-2-methyl-1-oxo-3-[3-(phenylmethoxy)phenyl]pentyl]-4R-phenyl-2-Oxazolidinone

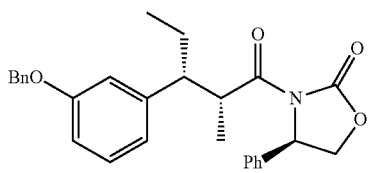

The product of Example 36 (8.58 g, 20 mmol) was placed in a double-necked flask, then it was purged with nitrogen and cooled to −20° C., after that, tetrahydrofuran was added, the solution of sodium hexamethyldisilylamide (NaHMDS) in tetrahydrofuran (2M, 10 ml, 20 mmol) was slowly added dropwise, and the reaction was kept at −20° C. for 30 min; and then the solution of bromomethane in tetrahydrofuran (2.5M, 16 mL, 40 mmol) was added, the reaction was continued at −20° C. for 30 min, after it was slowly warmed to 0° C., the reaction was continued for 1 hour and quenched with saturated ammonium chloride solution. The reaction solution was concentrated to remove tetrahydrofuran and extracted with ethyl acetate for three times, then the organic phases were combined, washed with saturated brine, dried over anhydrous sodium sulfate, concentrated and recrystallized with petroleum ether and ethyl acetate to give a white solid 7.5 g, Yield: 85%, d.r.=99.9:0.1. The HNMR spectrum data is the same as that in Example 3.

Example 38

(βR,γR)-γ-ethyl-N,N,β-trimethyl-3-(phenylmethoxy)benzenepropanamine

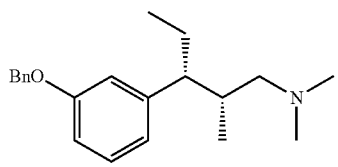 [SMILES: CC[C@@H](c1cccc(OCc2ccccc2)c1)[C@@H](C)CN(C)C]

Lithium aluminum tetrahydride (730 mg, 20 mmol) was suspended in tetrahydrofuran (10 ml), the product of Example 5 (3.2 g, 10 mmol) was dissolved in toluene, cooled in an ice-water bath, the solution of red aluminum in toluene (9 mL, 30 mmol) was added dropwise, the reaction was carried out for 2 hours and then quenched by adding 10% NaOH aqueous solution. After the reaction solution was separated, the organic phase was washed with saturated brine, dried over anhydrous sodium sulfate, and concentrated to give a pale yellow oil 2.8 g, yield: 90%. The HNMR spectrum data is the same as that in Example 6.

Example 39

3-((1R,2R)-3-(dimethylamino)-1-ethyl-2-methylpropyl)-phenol hydrochloride

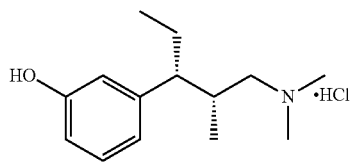 [SMILES: CC[C@@H](c1cccc(O)c1)[C@@H](C)CN(C)C ; Cl]

20 mL of water and 20 mL of concentrated hydrochloric acid were added to the product of Example 38 (2.5 g, 8 mmol), then it was reacted at 80° C. for 17 hours, after that, the reaction solution was concentrated and recrystallized with isopropanol and isopropyl ether to give the target 1.9 g, yield: 90%. The HNMR spectrum data is the same as that in Example 7.

Example 40

(βR,γR)-γ-ethyl-β-methyl-3-(phenylmethoxy)benzenepropanol, 1-(4-methylbenzenesulfonate)

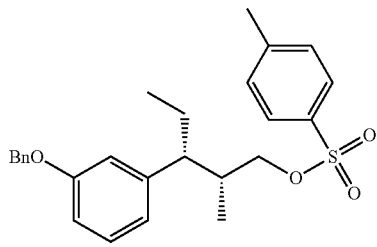 [SMILES: CC[C@@H](c1cccc(OCc2ccccc2)c1)[C@@H](C)COS(=O)(=O)c1ccc(C)cc1]

The product of Example 32 (2.6 g, 9 mmol) was dissolved in dichloromethane, triethylamine (1.9 ml, 13.5 mmol) was added therein, and the mixture was cooled in an ice-water bath, then p-toluenesulfonyl chloride (1.9 g, 10 mmol) was slowly added dropwise, after the addition was complete, the reaction was continued for 1 hour and then quenched by adding water. After the reaction solution was separated, the aqueous phase was extracted with dichloromethane three times, and the organic phases were combined, washed with saturated brine, dried over anhydrous sodium sulfate, and concentrated to give the target compound 3.0 g, yield: 91%.
$^1$HNMR (300 MHz, CDCl$_3$): δ 7.7 (4H, m), 7.5-7.4 (5H, m), 7.4-7.3 (4H, m), 7.2 (1H, t, J=7.6, 15.3), 6.7-6.9 (3H, m), 5.0 (2H, s), 3.4 (1H, m), 3.5 (1H, m), 3.1 (3H, s), 2.8 (1H: m), 2.7 (1H, m), 1.7-1.8 (1H, m), 1.5-1.6 (1H, m), 1.1 (3H, d, 6.8), 0.9 (3H, t, J=7.3, 14.5). ESI-MS: 337.5 (M−H).

Example 41

(βR,γR)-γ-ethyl-N,N,β-trimethyl-3-(phenylmethoxy)benzenepropanamine

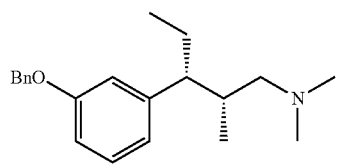 [SMILES: CC[C@@H](c1cccc(OCc2ccccc2)c1)[C@@H](C)CN(C)C]

The product of Example 40 (3.7 g, 8 mmol) was dissolved in dichloromethane, triethylamine (4.6 ml, 20 mmol) and dimethylamine hydrochloride (1.3 g, 16 mmol) were added therein, and it was reacted at room temperature for 8 hours, then water was added for separating, the aqueous phase was extracted twice with dichloromethane, and the organic phases were combined, washed with saturated brine, dried over anhydrous sodium sulfate, concentrated, and separated through silica gel column chromatography to give target 2.2 g, yield: 90%.

Example 42

1-[(1R,2R)-3-chloro-1-ethyl-2-methylpropyl]-3-(phenylmethoxy)benzene

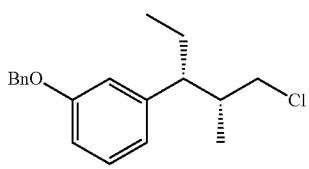 [SMILES: CC[C@@H](c1cccc(OCc2ccccc2)c1)[C@@H](C)CCl]

The product of Example 32 (2.6 g, 9 mmol) was dissolved in dichloromethane, the mixture was cooled in an ice-water bath, then N, N-dimethylformamide (2 drops) was added and thionyl chloride (0.64 mL, 10 mmol) was added dropwise, after the addition was complete, the reaction was conducted under reflux for 6 hours and quenched by adding water. After the reaction solution was separated, the aqueous phase was extracted with dichloromethane three times, and the organic phases were combined, washed with saturated brine, dried over anhydrous sodium sulfate, and concentrated to give the target compound 2.4 g, yield: 90%.
$^1$HNMR (300 MHz, CDCl$_3$): δ 7.3-7.5 (5H, m), 7.2 (1H, t, J=7.6, 15.3), 6.7-6.9 (3H, m), 5.0 (2H, s), 3.4 (1H, m), 3.3

(1H, m), 2.8 (1H, m), 2.7 (1H, m), 1.7-1.8 (1H, m), 1.5-1.6 (1H, m), 1.1 (3H, d, 6.8), 0.9 (3H, t, J=7.3, 14.5). ESI-MS: 301.2 (M−H).

Example 43

(βR,γR)-γ-ethyl-N,N,β-trimethyl-3-(phenylmethoxy)benzenepropanamine

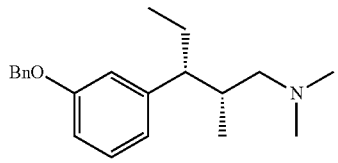 [SMILES: CC[C@@H](c1cccc(OCc2ccccc2)c1)[C@@H](C)CN(C)C]

The product of Example 42 (2.4 g, 8 mmol) was dissolved in N,N-dimethylformamide, potassium carbonate (2.7 g, 20 mmol) and dimethylamine hydrochloride (0.7 g, 8 mmol) were added therein, then it was reacted at room temperature for 12 hours. After that, the reaction solution was poured into water, the aqueous phase was extracted with dichloromethane twice, then the organic phases were combined, washed with saturated brine, dried over anhydrous sodium sulfate, concentrated, and separated through silica gel column chromatography to give target 2.2 g, yield: 90%.

Example 44

1-[(1R,2R)-3-bromo-1-ethyl-2-methylpropyl]-3-(phenylmethoxy)benzene

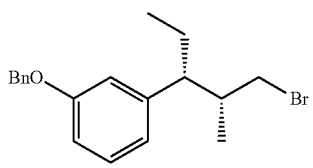 [SMILES: CC[C@@H](c1cccc(OCc2ccccc2)c1)[C@@H](C)CBr]

The product of Example 32 (2.6 g, 9 mmol) was dissolved in dichloromethane, and the mixture was cooled in an ice-water bath, then 48% hydrobromic acid (0.54 mL, 10 mmol) was added dropwise, after the addition was complete, it was reacted at room temperature for 16 hours. After that, water was added therein for separating, the aqueous phase was extracted with dichloromethane three times, then the organic phases were combined, washed with saturated brine, dried over anhydrous sodium sulfate, and concentrated to give the target compound 2.7 g, yield: 87%.

$^1$HNMR (300 MHz, CDCl$_3$): δ 7.3-7.5 (5H, m), 7.2 (1H, t, J=7.6, 15.3), 6.7-6.9 (3H, m), 5.0 (2H, s), 3.4 (1H, m), 3.2 (1H, m), 2.8 (1H, m), 2.7 (1H, m), 1.7-1.8 (1H, m), 1.5-1.6 (1H, m), 1.1 (3H, d, 6.8), 0.9 (3H, t, J=7.3, 14.5). ESI-MS: 346.2 (M−H).

Example 45

(βR,γR)-γ-ethyl-N,N,β-trimethyl-3-(phenylmethoxy)benzenepropanamine

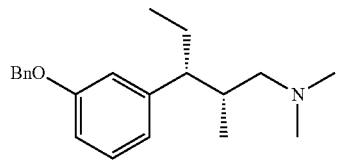 [SMILES: CC[C@@H](c1cccc(OCc2ccccc2)c1)[C@@H](C)CN(C)C]

The product of Example 44 (2.7 g, 8 mmol) was dissolved in N,N-dimethylformamide, potassium carbonate (2.7 g, 20 mmol) and dimethylamine hydrochloride (0.7 g, 8 mmol) were added therein, and it was reacted at room temperature for 12 hours. After the reaction solution was poured into water, the aqueous phase was extracted with dichloromethane twice, then the organic phases were combined, washed with saturated brine, dried over anhydrous sodium sulfate, concentrated, and separated through silica gel column chromatography to give target 2.1 g, yield: 89%.

What is claimed is:

1. A (2R,3R)-3-(3-substituted phenyl)-2-methyl n-pentanamide compound as shown in formula I (compound I),

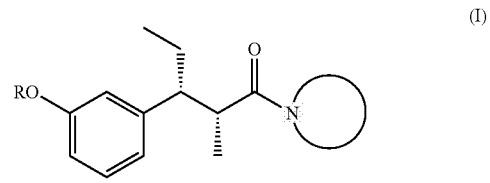

(I)

wherein R is a protecting group of a phenolic hydroxyl group;
wherein

is a chiral auxiliary residue, which is defined as follows:

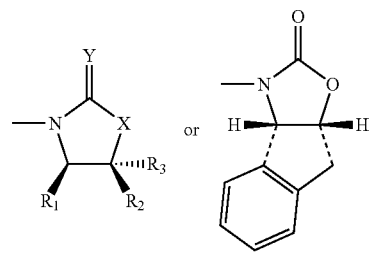

wherein X is O, S or NR$_7$, wherein R$_7$ is hydrogen, C1-C6 branched or linear alkyl;
wherein Y is O or S;
wherein R$_1$ is C1-C6 alkyl group, substituted or unsubstituted phenyl, substituted or unsubstituted naphthyl, substituted or unsubstituted benzyl, C1-C6 alkoxycarbonyl, wherein the substituent on phenyl, naphthyl or benzyl is 1 to 3 substituent(s) selected from hydroxy, halogen, C1-C6 alkyl and C1-C6 alkoxy;
wherein R$_2$ and R$_3$ are each independently selected from H; C1-C6 alkyl; phenyl; phenyl substituted with 1 to 3 substituent(s) selected from hydroxy, halogen, C1-C6 alkyl and C1-C6 alkoxy.

2. The (2R,3R)-3-(3-substituted phenyl)-2-methyl n-pentanamide compound according to claim 1, wherein R and the phenolic hydroxyl group form an ether group or an ester group; wherein R is selected from C1-C6 linear or branched alkyl, substituted or unsubstituted aryl, substituted or unsubstituted arylalkyl, alkylsilyl, C1-C6 alkoxymethyl, C1-C6 alkyloyl, substituted or unsubstituted aryloyl; wherein the substituent is hydroxy, halogen, C1-C6 alkyl or C1-C6 alkoxy; said aryl is phenyl or naphthyl;

wherein X is O; and Y is O;
wherein $R_1$ is C1-C6 alkyl group, substituted or unsubstituted phenyl, substituted or unsubstituted benzyl, wherein the substituent on phenyl or benzyl is 1 to 3 substituent(s) selected from hydroxy, halogen, C1-C6 alkyl and C1-C6 alkoxy;
wherein $R_2$ and $R_3$ are each independently selected from H, C1-C6 alkyl and phenyl.

3. The (2R,3R)-3-(3-substituted phenyl)-2-methyl n-pentanamide compound according to claim 2,
wherein R is benzyl, methyl, t-butyl, triphenylmethyl, methoxymethyl, trimethylsilyl, t-butyldimethylsilyl, acetyl or benzoyl;
wherein X is O; and Y is O;
wherein $R_1$ is phenyl; phenyl substituted with 1 to 3 substituent(s) selected from hydroxy, halogen, C1-C6 alkyl and C1-C6 alkoxy; benzyl;
wherein $R_2$ and $R_3$ are each independently selected from H, C1-C6 alkyl and phenyl.

4. The (2R,3R)-3-(3-substituted phenyl)-2-methyl n-pentanamide compound according to claim 3, said compound is selected from the group consisting of:

3-[(2R,3R)-2-methyl-1-oxo-3-[3-(phenylmethoxy)phenyl]pentyl]-4R-phenyl-2-Oxazolidinone

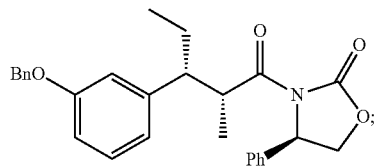

3-[(2R,3R)-2-methyl-1-oxo-3-[3-(phenylmethoxy)phenyl]pentyl]-4R,5S-diphenyl-2-Oxazolidinone

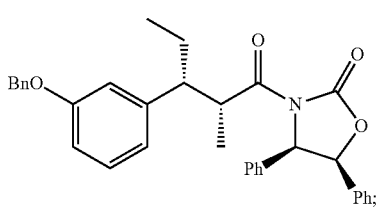 [SMILES: CC[C@@H](c1cccc(OCc2ccccc2)c1)[C@@H](C)C(=O)N1C(=O)O[C@@H](c2ccccc2)[C@H]1c1ccccc1]

3-[(2R,3R)-3-(3-methoxyphenyl)-2-methyl-1-oxopentyl]-4R,5S-diphenyl-2-Oxazolidinone

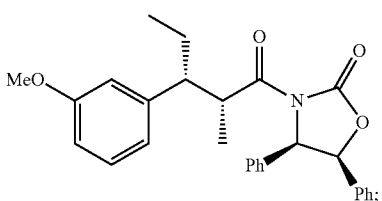

and
3-[(2R,3R)-3-(3-methoxyphenyl)-2-methyl-1-oxopentyl]-4R-phenyl-2-Oxazolidinone

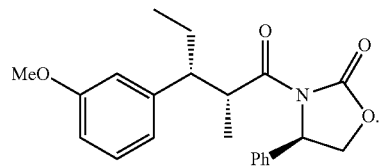 [SMILES: CC[C@@H](c1cccc(OC)c1)[C@@H](C)C(=O)N1C(=O)OC[C@H]1c1ccccc1]

5. A method for preparing the (2R,3R)-3-(3-substituted phenyl)-2-methyl n-pentanamide compound of claim 1, said method comprises:
reacting a compound of formula III (compound III) with a hydrocarbylation reagent in the presence of a strong base or a Lewis acid to produce said compound I through α-methylation reaction shown below

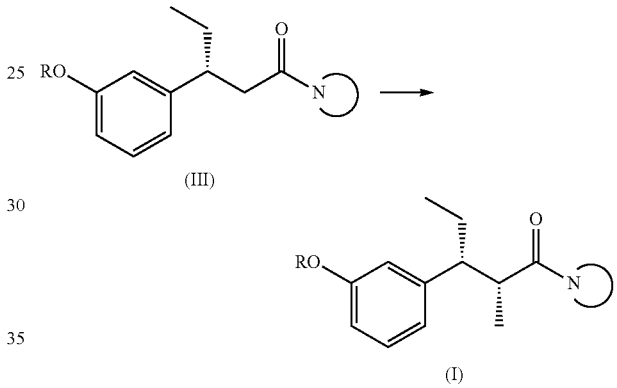

wherein R is a protecting group of a phenolic hydroxyl group;
wherein

is a chiral auxiliary residue, which is defined as follows:

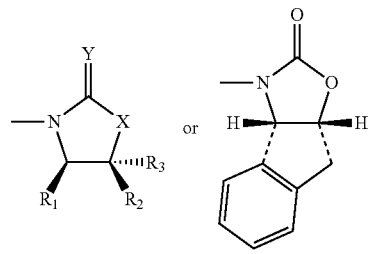

wherein X is O, S or $NR_S$, wherein $R_7$ is hydrogen, C1-C6 branched or linear alkyl;
wherein Y is O or S;
wherein $R_1$ is C1-C6 alkyl group, substituted or unsubstituted phenyl, substituted or unsubstituted naphthyl, substituted or unsubstituted benzyl, C1-C6 alkoxycarbonyl, wherein the substituent on phenyl, naphthyl or benzyl is 1 to 3 substituent(s) selected from hydroxy, halogen, C1-C6 alkyl and C1-C6 alkoxy;

wherein $R_2$ and $R_3$ are each independently selected from H; C1-C6 alkyl; phenyl; phenyl substituted with 1 to 3 substituent(s) selected from hydroxy, halogen, C1-C6 alkyl and C1-C6 alkoxy.

6. The method according to claim 5, wherein, said hydrocarbylation agent is any one of methyl iodide, methyl bromide, methyl chloride, methyl trifluoromethanesulfonate, methyl benzenesulfonate and methyl fluorosulfonate;

said strong base is any one of sodium hexamethyldisilylamide, lithium hexamethyldisilylamide, potassium hexamethyldisilylamide, lithium amide, sodium amide, potassium amide, lithium diisopropylamide and n-butyl lithium;

said Lewis acid is any one of titanium tetrachloride, aluminum trichloride, ferric trichloride, zinc chloride and antimony pentafluoride.

7. The method for preparing the (2R,3R)-3-(3-substituted phenyl)-2-methyl n-pentanamide compounds according to claim 5, wherein said compound III is prepared by the following steps:

a) reacting 3-(3-hydroxy protected phenyl) acrylic acid (Compound IV) with a chiral auxiliary

under the activation of a carboxylic acid activating agent in the presence of a strong base to produce a compound of formula V (compound V);

b) subjecting said compound V to an asymmetric Michael addition with ethyl magnesium halide under the condition of organic metal reagent in an inert solvent to produce said compound III;

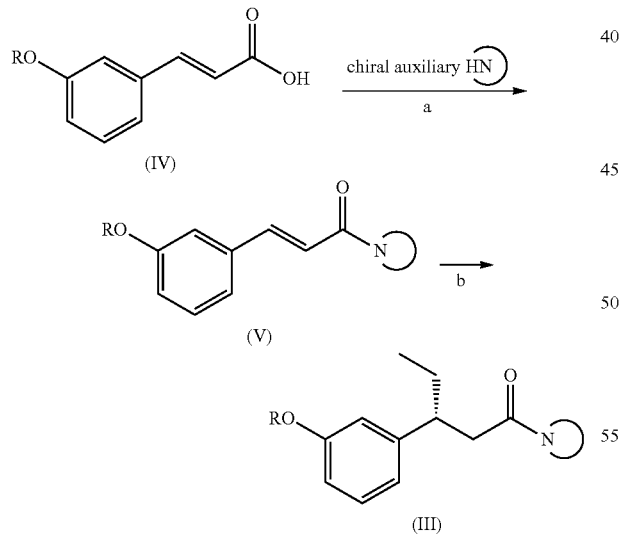

wherein R is a protecting group of a phenolic hydroxyl group;

wherein

is a chiral auxiliary residue, which is defined as follows:

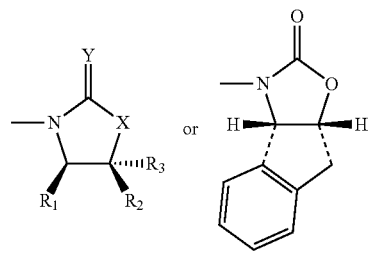

wherein X is O, S or $NR_S$, wherein $R_7$ is hydrogen, C1-C6 branched or linear alkyl;

wherein Y is O or S;

wherein $R_1$ is C1-C6 alkyl group, substituted or unsubstituted phenyl, substituted or unsubstituted naphthyl, substituted or unsubstituted benzyl, C1-C6 alkoxycarbonyl, wherein the substituent on phenyl, naphthyl or benzyl is 1 to 3 substituent(s) selected from hydroxy, halogen, C1-C6 alkyl and C1-C6 alkoxy;

wherein $R_2$ and $R_3$ are each independently selected from H; C1-C6 alkyl; phenyl; phenyl substituted with 1 to 3 substituent(s) selected from hydroxy, halogen, C1-C6 alkyl and C1-C6 alkoxy.

8. The method according to claim 7, wherein in the step a):

said carboxylic acid activating agent is any one of thionyl chloride, oxalyl chloride, pivaloyl chloride, chloroformate, carbodiimides, 4-dimethylaminopyridine and carbonyldiimidazole;

said base is any inorganic base or organic base selected from sodium hydride, potassium hydride, n-butyl lithium, t-butyl lithium, lithium amide, sodium amide, potassium amide, lithium diisopropylamide (LDA), lithium hexamethyldisilylamide (LiHMDS), sodium hexamethyldisilylamide (NaHMDS), sodium methoxide, sodium ethoxide, potassium tert-butoxide, sodium hydroxide, potassium hydroxide, calcium hydroxide, triethylamine, ethylenediamine, sodium carbonate, potassium carbonate, sodium bicarbonate and potassium bicarbonate;

wherein a solvent is used, said solvent is selected from the group consisting of benzene, xylene, toluene, dichloromethane, chloroform, tetrahydrofuran, diethyl ether, dipropyl ether, 1,4-dioxane, N,N-dimethylformamide, N,N-diethyl formamide, N,N-dimethylacetamide, acetonitrile and mixtures thereof;

wherein said step a) is carried out at a reaction temperature of from −100° C. to 50° C.;

in the step b):

said organic metal reagent is any one of cuprous bromide dimethylsulfide, cuprous bromide, cuprous chloride and cuprous iodide;

said ethyl magnesium halide is any one of ethyl magnesium bromide, ethyl magnesium iodide and ethyl magnesium chloride;

said inert solvent is C1-C4 halogenated hydrocarbon, C6-C8 aromatic hydrocarbon, C2-C6 ether or C2-C6 nitrile;

the amount of said ethyl magnesium halide is 1 to 10 times (molar ratio) that of said compound V;

the amount of said organic metal reagent is 0.1 to 5 times (molar ratio) that of said compound V;

wherein said step b) is carried out at a reaction temperature of from −50° C. to 50° C. and for a reaction time of from 2 to 10 hours.

9. The method for preparing the (2R,3R)-3-(3-substituted phenyl)-2-methyl n-pentanamide compounds according to claim 5, wherein said compound III is prepared by the following steps:

d) reacting trans-pent-2-enoic acid (compound VI) with a chiral auxiliary

under the activation of a carboxylic acid activating agent in the presence of a base to produce a compound of formula VII (compound VII);

e) subjecting said compound VII to an asymmetric Michael addition with 3-hydroxy protected phenyl magnesium halide under the condition of organic metal reagent in an inert solvent to produce a compound of formula VIII (compound VIII);

f) removing said chiral auxiliary

from said compound VIII to produce a compound of formula IX (compound IX);

g) reacting said compound IX with a chiral auxiliary

under the activation of a carboxylic acid activating agent in the presence of a base to produce said compound III;

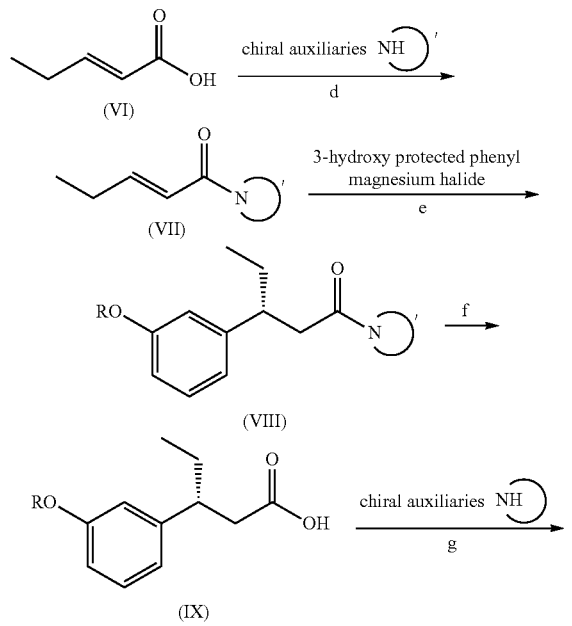

-continued

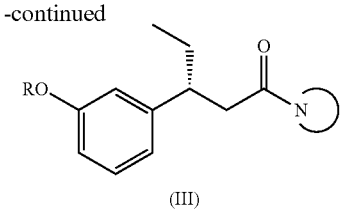

wherein R is a protecting group of a phenolic hydroxyl group;
wherein

is a chiral auxiliary residue, which is defined as follows:

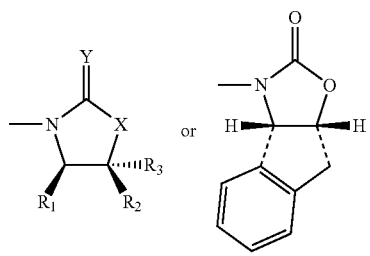

wherein X is O, S or NR$_S$, wherein R$_7$ is hydrogen, C1-C6 branched or linear alkyl;
wherein Y is O or S;
wherein R$_1$ is C1-C6 alkyl group, substituted or unsubstituted phenyl, substituted or unsubstituted naphthyl, substituted or unsubstituted benzyl, C1-C6 alkoxycarbonyl, wherein the substituent on phenyl, naphthyl or benzyl is 1 to 3 substituent(s) selected from hydroxy, halogen, C1-C6 alkyl and C1-C6 alkoxy;
wherein R$_2$ and R$_3$ are each independently selected from H; C1-C6 alkyl; phenyl; phenyl substituted with 1 to 3 substituent(s) selected from hydroxy, halogen, C1-C6 alkyl and C1-C6 alkoxy;
wherein

is a chiral auxiliary residue, which is defined as follows:

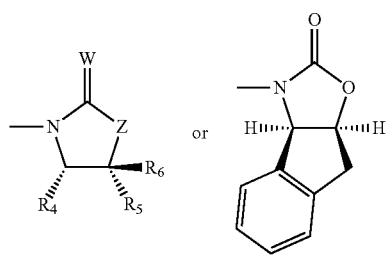

wherein, Z is O, S or NR$_8$, wherein R$_8$ is hydrogen, C1-C6 branched or linear alkyl;
wherein W is O or S;

wherein R₄ is C1-C6 alkyl group, substituted or unsubstituted phenyl, substituted or unsubstituted naphthyl, substituted or unsubstituted benzyl, C1-C6 alkoxycarbonyl, wherein the substituent on phenyl, naphthyl or benzyl is 1 to 3 substituent(s) selected from hydroxy, halogen, C1-C6 alkyl and C1-C6 alkoxy;

wherein R₅ and R₆ are each independently selected from H; C1-C6 alkyl; phenyl; phenyl substituted with 1 to 3 substituent(s) selected from hydroxy, halogen, C1-C6 alkyl and C1-C6 alkoxy.

10. The method according to claim 9, wherein in the step d), said carboxylic acid activating agent is any one of thionyl chloride, oxalyl chloride, pivaloyl chloride, chloroformate, carbodiimides, 4-dimethylaminopyridine and carbonyldiimidazole;

said base is any inorganic base or organic base selected from the group consisting of sodium hydride, potassium hydride, n-butyl lithium, t-butyl lithium, lithium amide, sodium amide, potassium amide, lithium diisopropylamide (LDA), lithium hexamethyldisilylamide (LiHMDS), sodium hexamethyldisilylamide (NaHMDS), sodium methoxide, sodium ethoxide, potassium tert-butoxide, sodium hydroxide, potassium hydroxide, calcium hydroxide, triethylamine, ethylenediamine, sodium carbonate, potassium carbonate, sodium bicarbonate and potassium bicarbonate;

wherein an organic solvent is used, said organic solvent comprises a solvent selected from the group consisting of benzene, xylene, toluene, dichloromethane, chloroform, tetrahydrofuran, diethyl ether, dipropyl ether, 1,4-dioxane, N,N-dimethylformamide, N,N-diethyl formamide, N,N-dimethylacetamide, acetonitrile and the mixtures thereof;

wherein said step d) is carried out at a reaction temperature of from −100° C. to 50° C.;

in the step e), said organic metal reagent is any one of cuprous bromide dimethylsulfide, cuprous bromide, cuprous chloride and cuprous iodide;

the 3-hydroxy protected phenyl magnesium halide is any one selected from 3-hydroxy protected phenyl magnesium bromide, 3-hydroxy protected phenyl magnesium iodide and 3-hydroxy protected phenyl magnesium chloride;

said inert solvent is C1-C4 halogenated hydrocarbon, C6-C8 aromatic hydrocarbon, C2-C6 ether or C2-C6 nitrile;

the amount of said 3-hydroxy protected phenyl magnesium halide is 1 to 10 times (molar ratio) that of said compound VII;

the amount of said organic metal reagent is 0.1 to 5 times (molar ratio) that of said compound VII;

wherein said step e) is carried out at a reaction temperature of from −50° C. to 50° C. and for a reaction time of from 2 to 10 hours;

in the step f), said chiral auxiliary residue

is removed from said compound VIII in the presence of hydrogen peroxide and an alkali metal hydroxide, said alkali metal hydroxide is any one selected from lithium hydroxide, sodium hydroxide and potassium hydroxide;

in the step g), said carboxylic acid activating agent is any one of thionyl chloride, oxalyl chloride, pivaloyl chloride, chloroformate, carbodiimides, 4-dimethylaminopyridine and caarbonyldiimidazole;

said base is any inorganic base or organic base selected from sodium hydride, potassium hydride, n-butyl lithium, t-butyl lithium, lithium amide, sodium amide, potassium amide, lithium diisopropylamide (LDA), lithium hexamethyldisilylamide (LiHMDS), sodium hexamethyldisilylamide (NaHMDS), sodium methoxide, sodium ethoxide, potassium tert-butoxide, sodium hydroxide, potassium hydroxide, calcium hydroxide, triethylamine, ethylenediamine, sodium carbonate, potassium carbonate, sodium bicarbonate and potassium bicarbonate;

wherein an organic solvent is used, said organic solvent comprises a solvent selected from the group consisting of benzene, xylene, toluene, dichloromethane, chloroform, tetrahydrofuran, diethyl ether, dipropyl ether, 1,4-dioxane, N,N-dimethylformamide, N,N-diethylformamide, N,N-dimethylacetamide, acetonitrile and mixtures thereof;

wherein said step g) is carried out at a reaction temperature of from −100° C. to 50° C.

11. A method for preparation of tapentadol or a pharmaceutical acceptable salt of tapentadol using the (2R,3R)-3-(3-substituted phenyl)-2-methyl n-pentanamide compound of claim 1, comprising the following steps:

1) removing said chiral auxiliary residue of said compound I to generate a compound of formula X (compound X);

2) subjecting said compound X to an amidation reaction with dimethylamine or its salt under the activation of a carboxylic acid activating agent to produce a compound of formula XI (compound XI);

3) reducing said compound XI using a reducing agent to produce a compound of formula XII (compound XII);

4) removing said protection group of phenolic hydroxy group in said compound XII to produce tapentadol II;

5) dissolving said tapentadol II in a solvent, and then adding an acid HA to produce a pharmaceutically acceptable salt of tapentadol; or after removing said protection group of said phenolic hydroxy group, without separation, directly adding an acid HA to produce a pharmaceutically acceptable salt of tapentadol;

-continued

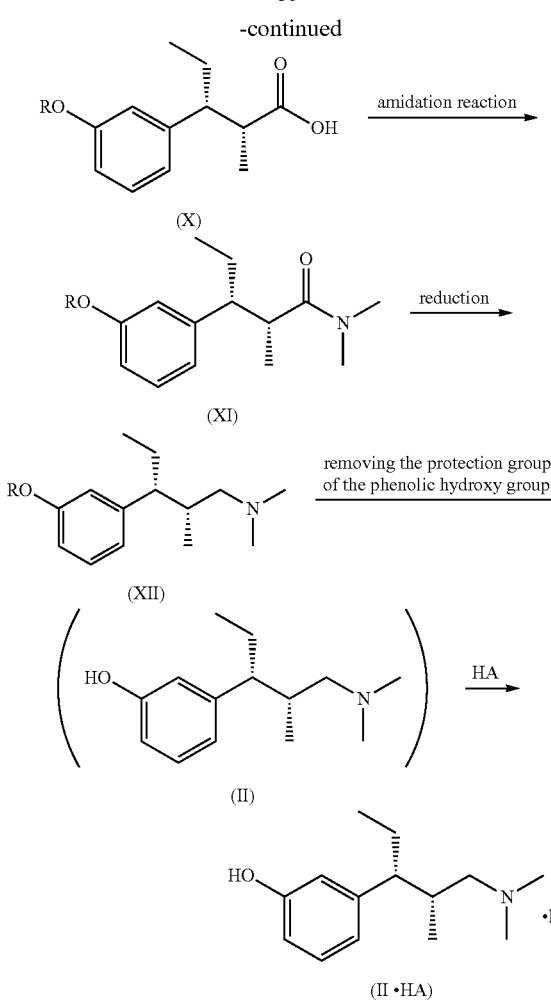

wherein R is a protecting group of a phenolic hydroxyl group;
wherein

is a chiral auxiliary residue, which is defined as follows:

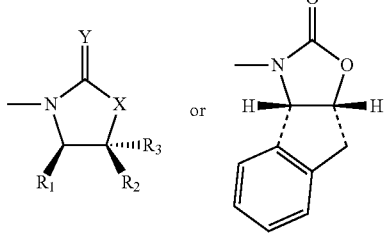

wherein X is O, S or $NR_S$, wherein $R_7$ is hydrogen, C1-C6 branched or linear alkyl;
wherein Y is O or S;
wherein $R_1$ is C1-C6 alkyl group, substituted or unsubstituted phenyl, substituted or unsubstituted naphthyl, substituted or unsubstituted benzyl, C1-C6 alkoxy-carbonyl, wherein the substituent on phenyl, naphthyl or benzyl is 1 to 3 substituent(s) selected from hydroxy, halogen, C1-C6 alkyl and C1-C6 alkoxy;
wherein $R_2$ and $R_3$ are each independently selected from H; C1-C6 alkyl; phenyl; phenyl substituted with 1 to 3 substituent(s) selected from hydroxy, halogen, C1-C6 alkyl and C1-C6 alkoxy.

12. The method according to claim 11, wherein,
in step 1), said chiral auxiliary residue is removed from said compound I in the presence of hydrogen peroxide and an alkali metal hydroxide, said alkali metal hydroxide is any one selected from lithium hydroxide, sodium hydroxide and potassium hydroxide;
in step 2), said carboxylic acid activating agent is any one of thionyl chloride, oxalyl chloride, pivaloyl chloride, chloroformate, carbodiimides, 4-dimethylaminopyridine and carbonyldiimidazole;
in step 3), said reducing agent is any one of lithium aluminum tetrahydride, sodium borohydride/cobaltic chloride, boron trifluoride diethyl ether and zinc chloride;
in step 4), the reaction condition for removing the protecting group of phenolic hydroxy group is one selected from the follows: hydrochloric acid; hydrobromic acid; boron tribromide; palladium on carbon, formic acid and ammonium formate; palladium on carbon/hydrogen; Raney nickel/hydrogen and platinum dioxide/hydrogen;
in step 5), said acid HA is an inorganic acid selected from the group consisting of hydrochloric acid, nitric acid, phosphoric acid, sulfuric acid, hydrobromic acid and hydroiodic acid; or an organic acid selected from formic acid, acetic acid, propionic acid, butyric acid, malic acid, tartaric acid, amino acid, methanesulfonic acid, benzenesulfonic acid, p-toluenesulfonic acid, naphthalenesulfonic acid, camphorsulfonic acid, taurine, fumaric acid, maleic acid, citric acid, succinic acid, cholic acid and deoxycholic acid.

13. A method for preparation of tapentadol or a pharmaceutically acceptable salt of tapentadol using the (2R,3R)-3-(3-substituted phenyl)-2-methyl n-pentanamide compound of claim 1, comprising the following steps:
1) removing said chiral auxiliary residue

of said compound I to produce compound X;
2) subjecting said compound X to an amidation reaction with dimethylamine or its salt under the activation of a carboxylic acid activating agent to produce compound XI;
3) removing the protection group of the phenolic hydroxy group from said compound XI to produce compound XIII;
4) reducing said compound XIII using a reducing agent to produce tapentadol II;
5) dissolving said tapentadol II in a solvent, and then adding an acid HA therein to produce a pharmaceutically acceptable salt of tapentadol; or after the carbonyl group is reduced, without separation, directly adding an acid HA to produce a pharmaceutically acceptable salt of tapentadol;

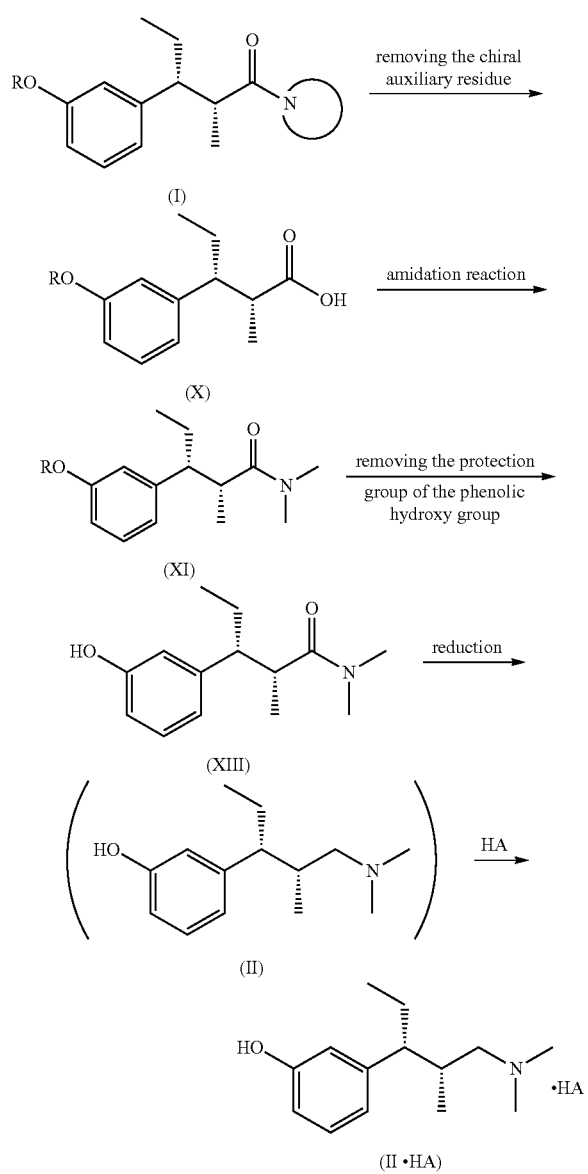

wherein R is a protecting group of a phenolic hydroxyl group;
wherein

is a chiral auxiliary residue, which is defined as follows:

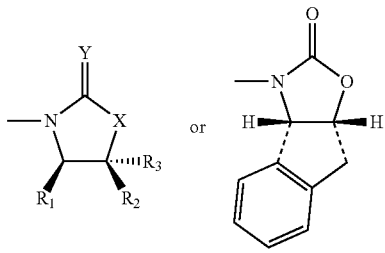

wherein X is O, S or NR$_7$, wherein R$_7$ is hydrogen, C1-C6 branched or linear alkyl;

wherein Y is O or S;

wherein R$_1$ is C1-C6 alkyl group, substituted or unsubstituted phenyl, substituted or unsubstituted naphthyl, substituted or unsubstituted benzyl, C1-C6 alkoxycarbonyl, wherein the substituent on phenyl, naphthyl or benzyl is 1 to 3 substituent(s) selected from hydroxy, halogen, C1-C6 alkyl and C1-C6 alkoxy;

wherein R$_2$ and R$_3$ are each independently selected from H; C1-C6 alkyl; phenyl; phenyl substituted with 1 to 3 substituent(s) selected from hydroxy, halogen, C1-C6 alkyl and C1-C6 alkoxy.

14. The method according to claim 13, wherein, in step 1), said chiral auxiliary residue is removed from said compound I in the presence of hydrogen peroxide and an alkali metal hydroxide, said alkali metal hydroxide is any one selected from lithium hydroxide, sodium hydroxide and potassium hydroxide;

in step 2), said carboxylic acid activating agent is any one of thionyl chloride, oxalyl chloride, pivaloyl chloride, chloroformate, carbodiimides, 4-dimethylaminopyridine and carbonyldiimidazole;

in step 3), the reaction condition for removing the said protecting group of phenolic hydroxy group is one selected from the follows: hydrochloric acid; hydrobromic acid; boron tribromide; palladium on carbon, formic acid and ammonium formate; palladium on carbon/hydrogen; Raney nickel/hydrogen and platinum dioxide/hydrogen;

in step 4), said reducing agent is any one of lithium aluminum tetrahydride, sodium borohydride/cobaltic chloride, boron trifluoride diethyl ether and zinc chloride;

in step 5), said acid HA is an inorganic acid selected from hydrochloric acid, nitric acid, phosphoric acid, sulfuric acid, hydrobromic acid and hydroiodic acid; or an organic acid selected from formic acid, acetic acid, propionic acid, butyric acid, malic acid, tartaric acid, amino acid, methanesulfonic acid, benzenesulfonic acid, p-toluenesulfonic acid, naphthalenesulfonic acid, camphorsulfonic acid, taurine, fumaric acid, maleic acid, citric acid, succinic acid, cholic acid and deoxycholic acid.

15. A method for preparation of tapentadol or a pharmaceutically acceptable salt of tapentadol using the (2R,3R)-3-(3-substituted phenyl)-2-methyl n-pentanamide compound of claim 1, comprising the following steps:

1) reducing said compound I to produce a compound of formula XIX (compound XIX);

2) converting a hydroxy group of said compound XIX to a leaving group LV to produce a compound of formula XX (compound XX);

3) reacting said compound XX with dimethylamine or its salt to produce a compound of formula XII (compound XII);

4) removing the protection group of the phenolic hydroxy group from said compound XII to produce tapentadol of formula II;

5) dissolving said tapentadol in a solvent, and then adding an acid HA therein to produce a pharmaceutically acceptable salt of tapentadol; or after removing the protection group of the phenolic hydroxy group, without separation, directly adding an acid HA to produce a pharmaceutically acceptable salt of tapentadol;

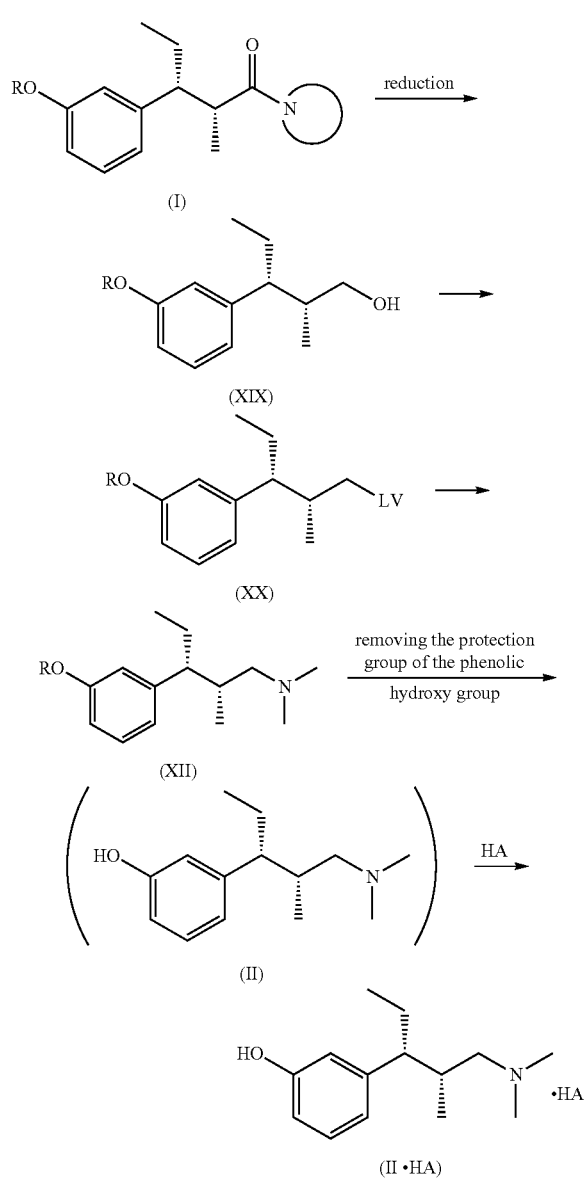

wherein LV is a leaving group selected from halogen, mesyl, phenylsulfonyl and substituted phenylsulfonyl;
wherein R is a protecting group of a phenolic hydroxyl group;
wherein

is a chiral auxiliary residue, which is defined as follows:

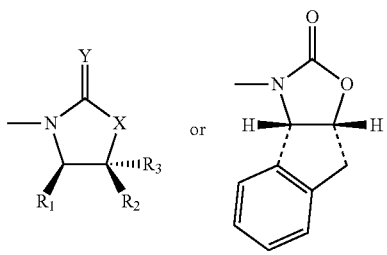

wherein X is O, S or $NR_5$, wherein $R_7$ is hydrogen, C1-C6 branched or linear alkyl;
wherein Y is O or S;
wherein $R_1$ is C1-C6 alkyl group, substituted or unsubstituted phenyl, substituted or unsubstituted naphthyl, substituted or unsubstituted benzyl, C1-C6 alkoxycarbonyl, wherein the substituent on phenyl, naphthyl or benzyl is 1 to 3 substituent(s) selected from hydroxy, halogen, C1-C6 alkyl and C1-C6 alkoxy;
wherein $R_2$ and $R_3$ are each independently selected from H; C1-C6 alkyl; phenyl; phenyl substituted with 1 to 3 substituent(s) selected from hydroxy, halogen, C1-C6 alkyl and C1-C6 alkoxy.

16. The method according to claim 15, wherein,
in step 1), said reducing is carried out in the presence of any one of lithium aluminum tetrahydride, sodium borohydride/cobaltic chloride, boron trifluoride diethyl ether and zinc chloride;
In step 2), a hydroxy group of said compound XIX is converted to a leaving group LV using a halogenated reagent or sulfonyl chloride;
in step 3), said compound XX is reacted with dimethylamine or its salt under an alkaline condition to produce said compound XII;
in step 4), the reaction condition for removing the protecting group of phenolic hydroxy group is one selected from the follows: hydrochloric acid; hydrobromic acid; boron tribromide; palladium on carbon, formic acid and ammonium formate; palladium on carbon/hydrogen; Raney nickel/hydrogen and platinum dioxide/hydrogen;
in step 5), said acid HA is an inorganic acid selected from the group consisting of hydrochloric acid, nitric acid, phosphoric acid, sulfuric acid, hydrobromic acid and hydroiodic acid; or an organic acid selected from formic acid, acetic acid, propionic acid, butyric acid, malic acid, tartaric acid, amino acid, methanesulfonic acid, benzenesulfonic acid, p-toluenesulfonic acid, naphthalenesulfonic acid, camphorsulfonic acid, taurine, fumaric acid, maleic acid, citric acid, succinic acid, cholic acid and deoxycholic acid.

17. A method for preparation of tapentadol or a pharmaceutically acceptable salt of tapentadol using the (2R,3R)-3-(3-substituted phenyl)-2-methyl n-pentanamide compound of claim 1,

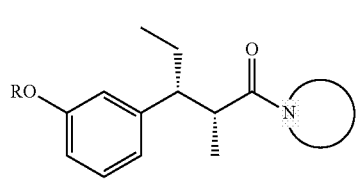

wherein R is a protecting group of a phenolic hydroxyl group;
in case of

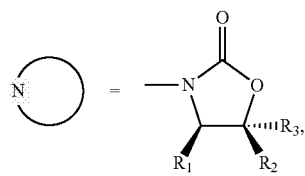

wherein R₁ is C1-C6 alkyl group, substituted or unsubstituted phenyl, substituted or unsubstituted naphthyl, substituted or unsubstituted benzyl, C1-C6 alkoxycarbonyl, wherein the substituent on phenyl, naphthyl or benzyl is 1 to 3 substituent(s) selected from hydroxy, halogen, C1-C6 alkyl and C1-C6 alkoxy;

wherein R₂ and R₃ are each independently selected from H; C1-C6 alkyl; phenyl; phenyl substituted with 1 to 3 substituent(s) selected from hydroxy, halogen, C1-C6 alkyl and C1-C6 alkoxy;

said method comprises the following steps:

1) hydrolyzing the lactone in chiral auxiliary residue of the compound of formula I to produce a compound of formula XIV (compound XIV);
2) reducing carbonyl group of said compound XIV to produce a compound of formula XV (compound XV);
3) removing the protection group on phenolic hydroxy group and the substituents on the amino group of said compound XV to produce a primary amine compound of formula XVI (compound XVI);
4) methylating said compound XVI to produce tapentadol of formula II;
5) dissolving said tapentadol in a solvent, and then adding an acid HA therein to produce a pharmaceutically acceptable salt of tapentadol; or after methylation reaction, without separation, directly adding an acid HA to produce a pharmaceutically acceptable salt of tapentadol;

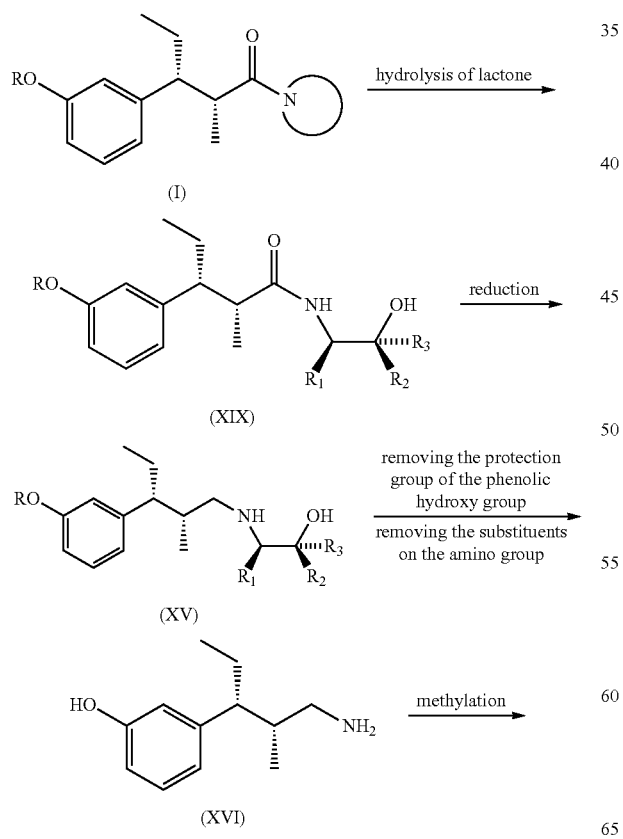

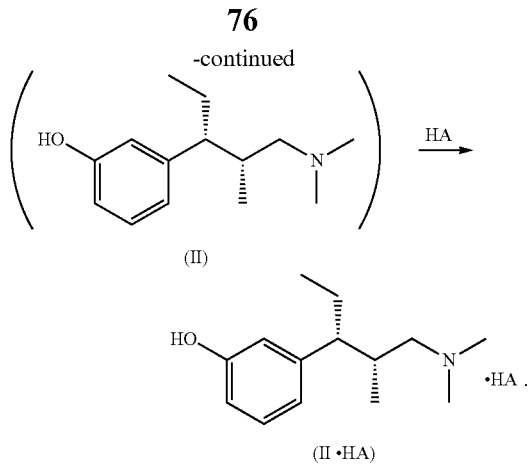

18. The method according to claim 17, wherein,
in step 1), the hydrolysis of lactone is carried out under an alkaline condition in the presence of an inorganic base selected from the group consisting of lithium hydroxide, potassium hydroxide and sodium hydroxide, or in the presence of an organic base selected from the group consisting of sodium methoxide and sodium ethoxide;
in step 2), said reducing is carried out in the presence of any one of lithium aluminum tetrahydride, sodium borohydride/cobaltic chloride, boron trifluoride diethyl ether and zinc chloride;
in step 3), the reaction condition for removing the said protecting group of phenolic hydroxy group is one selected from the follows: hydrochloric acid; hydrobromic acid; boron tribromide; palladium on carbon, formic acid and ammonium formate; palladium on carbon/hydrogen; Raney nickel/hydrogen and platinum dioxide/hydrogen; the reaction condition for removing the substituent on the amino group is one selected from the follows: palladium on carbon/hydrogen; Raney nickel/hydrogen and platinum dioxide/hydrogen;
in step 4), the methylation of said compound XVI is conducted in the presence of formaldehyde and formic acid;
in step 5), said acid HA is an inorganic acid selected from the group consisting of hydrochloric acid, nitric acid, phosphoric acid, sulfuric acid, hydrobromic acid and hydroiodic acid; or an organic acid selected from formic acid, acetic acid, propionic acid, butyric acid, malic acid, tartaric acid, amino acid, methanesulfonic acid, benzenesulfonic acid, p-toluenesulfonic acid, naphthalenesulfonic acid, camphorsulfonic acid, taurine, fumaric acid, maleic acid, citric acid, succinic acid, cholic acid and deoxycholic acid.

19. A method for preparation of tapentadol or a pharmaceutically acceptable salt of tapendadil using the (2R,3R)-3-(3-substituted phenyl)-2-methyl n-pentanamide compound of claim 1,

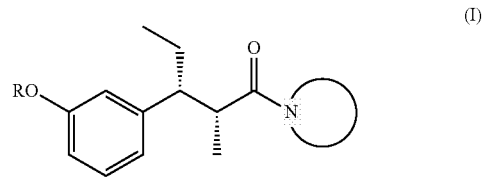

wherein R is a protecting group of a phenolic hydroxyl group;

in case of

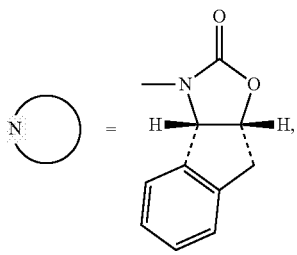

said method comprises the following steps:
1) hydrolyzing the lactone in chiral auxiliary residue of the compound of formula I to produce a compound of formula XVII (compound XVII);
2) reducing carbonyl group of said compound XVII to produce a compound of formula XVIII (compound XVIII);
3) removing the protection group on phenolic hydroxy group and the substituents on the amino group of said compound XVIII to produce a primary amine compound of formula XVI (compound XVI);
4) methylating said compound XVI to produce tapentadol of formula II;
5) dissolving said tapentadol in a solvent, and then adding an acid HA to produce a pharmaceutically acceptable salt of tapentadol; or after methylation reaction, without separation, directly adding an acid HA to produce a pharmaceutically acceptable salt of tapentadol;

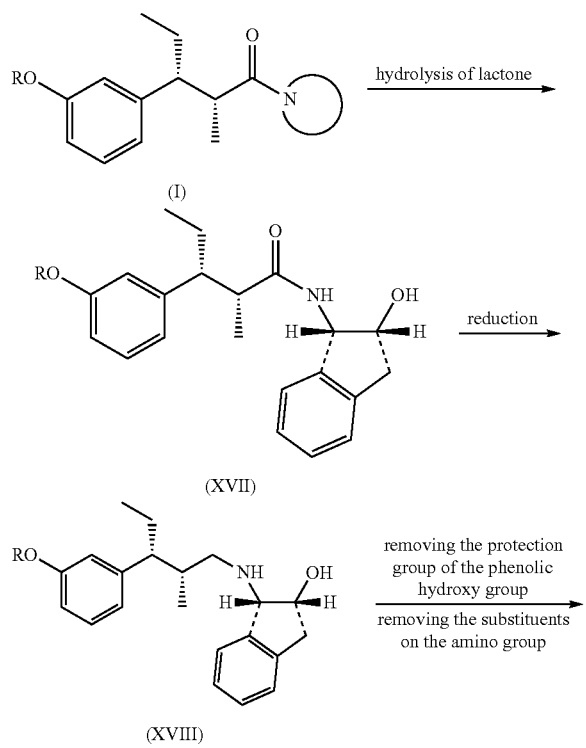

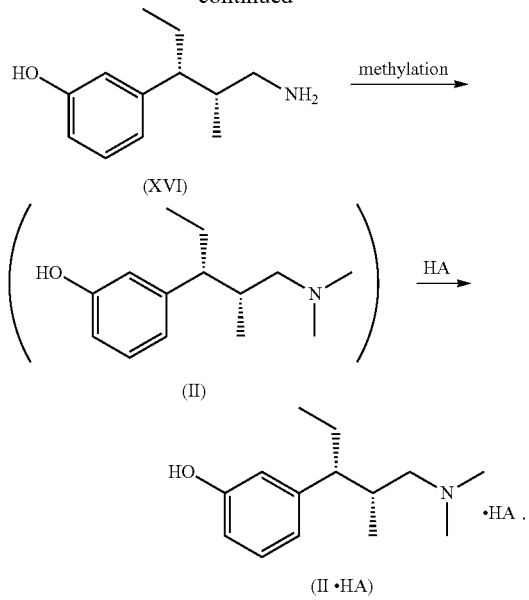

20. The method according to claim 19, wherein,
in step 1), the hydrolysis of lactone is carried out under an alkaline condition in the presence of an inorganic base selected from the group consisting of lithium hydroxide, potassium hydroxide and sodium hydroxide, or in the presence of an organic base selected from the group consisting of sodium methoxide or sodium ethoxide;
in step 2), said reducing is carried out in the presence of any one of lithium aluminum tetrahydride, sodium borohydride/cobaltic chloride, boron trifluoride diethyl ether and zinc chloride;
in step 3), the reaction condition for removing the protecting group of phenolic hydroxy group is one selected from the follows: hydrochloric acid; hydrobromic acid; boron tribromide; palladium on carbon, formic acid and ammonium formate; palladium on carbon/hydrogen; Raney nickel/hydrogen and platinum dioxide/hydrogen; the reaction condition for removing the substituent on the amino group is one selected from the follows: palladium on carbon/hydrogen; Raney nickel/hydrogen and platinum dioxide/hydrogen;
in step 4), the methylation of said compound XVI is conducted in the presence of formaldehyde and formic acid;
in step 5), said acid HA is an inorganic acid selected from hydrochloric acid, nitric acid, phosphoric acid, sulfuric acid, hydrobromic acid and hydroiodic acid; or an organic acid selected from formic acid, acetic acid, propionic acid, butyric acid, malic acid, tartaric acid, amino acid, methanesulfonic acid, benzenesulfonic acid, p-toluenesulfonic acid, naphthalenesulfonic acid, camphorsulfonic acid, taurine, fumaric acid, maleic acid, citric acid, succinic acid, cholic acid and deoxycholic acid.

21. The method of claim 11, wherein R is benzyl or methyl.
22. The method of claim 13, wherein R is benzyl or methyl.
23. The method of claim 15, wherein R is benzyl or methyl.
24. The method of claim 17, wherein R is benzyl or methyl.
25. The method of claim 19, wherein R is benzyl or methyl.

* * * * *